(12) United States Patent
Schaller et al.

(10) Patent No.: US 12,115,104 B2
(45) Date of Patent: Oct. 15, 2024

(54) DEVICES AND METHODS FOR OCULAR SURGERY

(71) Applicant: Carl Zeiss Meditec Cataract Technology Inc., Reno, NV (US)

(72) Inventors: Michael Schaller, Reno, NV (US); Peter Bentley, Reno, NV (US); Luke W. Clauson, Reno, NV (US); Maria Tsontcheva Guguchkova, Reno, NV (US); Matthew Newell, Reno, NV (US); Adam Larson, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 808 days.

(21) Appl. No.: 17/177,017

(22) Filed: Feb. 16, 2021

(65) Prior Publication Data

US 2021/0161712 A1 Jun. 3, 2021

Related U.S. Application Data

(63) Continuation of application No. 16/221,239, filed on Dec. 14, 2018, now Pat. No. 10,932,951.

(60) Provisional application No. 62/696,769, filed on Jul. 11, 2018, provisional application No. 62/598,857, filed on Dec. 14, 2017.

(51) Int. Cl.
*A61F 9/007* (2006.01)
*A61F 9/008* (2006.01)
*A61F 9/013* (2006.01)

(52) U.S. Cl.
CPC ...... *A61F 9/00754* (2013.01); *A61F 9/00736* (2013.01); *A61F 9/00781* (2013.01); *A61F 9/008* (2013.01); *A61F 9/013* (2013.01); *A61F 9/00745* (2013.01); *A61F 2009/0087* (2013.01); *A61F 2009/00889* (2013.01)

(58) Field of Classification Search
CPC ............... A61F 9/0008; A61F 9/00736; A61F 9/00745; A61F 9/00754; A61F 9/00781; A61F 9/008; A61F 9/013; A61F 2009/0087; A61F 2009/00889; A61B 17/221; A61B 17/32002; A61B 17/320016; A61B 17/320052; A61B 17/32056; A61B 17/320725; A61B 2017/2212
See application file for complete search history.

(56) References Cited

U.S. PATENT DOCUMENTS

| | | |
|---|---|---|
| 1,891,054 A | 12/1932 | Pitman |
| 3,882,872 A | 5/1975 | Douvas et al. |
| 3,903,892 A | 9/1975 | Komiya |

(Continued)

FOREIGN PATENT DOCUMENTS

| | | |
|---|---|---|
| CN | 2192307 Y | 3/1995 |
| CN | 101495063 A | 7/2009 |

(Continued)

OTHER PUBLICATIONS

U.S. Appl. No. 15/970,439, filed May 3, 2018, US 2018-0318132.

(Continued)

*Primary Examiner* — Robert A Lynch
(74) *Attorney, Agent, or Firm* — Mintz Levin Cohn Ferris Glovsky and Popeo, P.C.

(57) ABSTRACT

A surgical device for cutting a lens within a capsular bag of an eye. Related methods, systems, and devices are also provided.

19 Claims, 46 Drawing Sheets

(56) References Cited

U.S. PATENT DOCUMENTS

| | | |
|---|---|---|
| 3,908,661 A | 9/1975 | Kramer |
| 3,973,568 A | 8/1976 | Iglesias |
| 4,367,744 A | 1/1983 | Sole |
| 4,538,611 A | 9/1985 | Kelman |
| 4,693,245 A | 9/1987 | Pao |
| 4,732,150 A | 3/1988 | Keener, Jr. |
| 4,766,897 A | 8/1988 | Smirmaul |
| 4,791,924 A | 12/1988 | Kelman |
| 4,869,716 A | 9/1989 | Smirmaul |
| 4,888,015 A | 12/1989 | Domino |
| 4,950,272 A | 8/1990 | Smirmaul |
| 4,955,887 A | 9/1990 | Zirm |
| 4,960,418 A | 10/1990 | Tennant |
| 5,123,906 A | 6/1992 | Kelman |
| 5,147,369 A | 9/1992 | Wagner |
| 5,156,607 A | 10/1992 | Kansas |
| 5,171,314 A | 12/1992 | Dulebohn |
| 5,201,741 A | 4/1993 | Dulebohn |
| 5,222,959 A | 6/1993 | Anis |
| 5,222,960 A | 6/1993 | Poley |
| 5,242,449 A | 9/1993 | Zaleski |
| 5,437,678 A | 8/1995 | Sorensen |
| 5,728,117 A | 3/1998 | Lash |
| 6,117,149 A | 9/2000 | Sorensen et al. |
| 6,120,496 A | 9/2000 | Whayne et al. |
| 6,379,370 B1 | 4/2002 | Feinsod |
| 6,551,326 B1 | 4/2003 | Van Heugten et al. |
| 6,554,843 B1 | 4/2003 | Ou |
| 6,743,228 B2 | 6/2004 | Lee et al. |
| 7,632,294 B2 | 12/2009 | Milbodker et al. |
| 7,867,163 B2 | 1/2011 | Chin et al. |
| 8,157,797 B2 | 4/2012 | Boukhny et al. |
| 8,814,854 B2 | 8/2014 | Jia et al. |
| 9,119,927 B1 * | 9/2015 | Ratterree ........... A61M 16/0447 |
| 9,381,033 B2 | 7/2016 | Guo |
| 9,629,747 B2 | 4/2017 | Clauson et al. |
| 9,775,743 B2 | 10/2017 | Clauson et al. |
| 10,292,862 B1 | 5/2019 | Mackool |
| 10,932,951 B2 * | 3/2021 | Schaller ................. A61F 9/013 |
| 2002/0019594 A1 | 2/2002 | McClellan et al. |
| 2003/0074008 A1 | 4/2003 | Ou |
| 2004/0092982 A1 | 5/2004 | Sheffer |
| 2004/0116950 A1 | 6/2004 | Eibschitz-Tsimhoni |
| 2004/0199159 A1 | 10/2004 | Lee et al. |
| 2004/0220564 A1 | 11/2004 | Ho et al. |
| 2004/0220604 A1 | 11/2004 | Fogarty et al. |
| 2004/0243142 A1 | 12/2004 | Siepser |
| 2008/0086148 A1 | 4/2008 | Baker et al. |
| 2008/0215000 A1 * | 9/2008 | Barere ................... A61M 5/502 |
| | | 604/110 |
| 2009/0054904 A1 | 2/2009 | Holmen |
| 2009/0204135 A1 | 8/2009 | Cote |
| 2009/0216225 A1 * | 8/2009 | Ben-Nun ............ A61F 9/00754 |
| | | 606/45 |
| 2010/0094278 A1 | 4/2010 | Jia et al. |
| 2010/0312232 A1 | 12/2010 | Jia et al. |
| 2010/0312252 A1 | 12/2010 | Jia et al. |
| 2011/0282335 A1 | 11/2011 | Jia et al. |
| 2012/0080502 A1 | 4/2012 | Morgan et al. |
| 2012/0172905 A1 | 7/2012 | Lee Shee et al. |
| 2013/0018385 A1 | 1/2013 | Keene et al. |
| 2013/0023894 A1 | 1/2013 | Saleh |
| 2014/0074011 A1 | 3/2014 | Charles |
| 2014/0114335 A1 | 4/2014 | Banko |
| 2014/0180396 A1 | 6/2014 | Pike et al. |
| 2014/0378988 A1 | 12/2014 | Raybin et al. |
| 2015/0005578 A1 | 1/2015 | Jorgensen et al. |
| 2015/0257927 A1 | 9/2015 | Olson |
| 2015/0297407 A1 | 10/2015 | Saimovici |
| 2015/0305934 A1 | 10/2015 | Joo et al. |
| 2015/0335393 A1 | 11/2015 | Ciulla et al. |
| 2016/0022489 A1 | 1/2016 | Hartstra |
| 2016/0030241 A1 | 2/2016 | Siepser |
| 2016/0067091 A1 | 3/2016 | Wells et al. |
| 2016/0074220 A1 | 3/2016 | Ianchulev et al. |
| 2016/0166432 A1 | 6/2016 | Kahook et al. |
| 2016/0346121 A1 * | 12/2016 | Ianchulev ........... A61F 9/00763 |
| 2017/0143341 A1 | 5/2017 | Belson et al. |
| 2017/0231647 A1 | 8/2017 | Saunders et al. |
| 2017/0312125 A1 | 11/2017 | Clauson et al. |
| 2017/0333252 A1 | 11/2017 | Biancalana et al. |
| 2018/0036171 A1 | 2/2018 | Clauson et al. |
| 2018/0064578 A1 | 3/2018 | Clauson et al. |
| 2018/0132998 A1 | 5/2018 | Page |
| 2018/0318132 A1 | 11/2018 | Clauson et al. |
| 2018/0318133 A1 | 11/2018 | Clauson et al. |
| 2019/0133825 A1 | 5/2019 | Clauson et al. |
| 2019/0151149 A1 | 5/2019 | Clauson et al. |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0321223 A1 | 10/2019 | Chamness et al. |
| 2019/0336337 A1 | 11/2019 | Mackool |
| 2019/0336338 A1 | 11/2019 | Mackool |
| 2019/0365567 A1 | 12/2019 | Balkenbush et al. |
| 2019/0388272 A1 | 12/2019 | Clauson et al. |
| 2020/0022841 A1 | 1/2020 | Chamness et al. |
| 2020/0060875 A1 | 2/2020 | Clauson et al. |
| 2020/0197222 A1 | 6/2020 | Clauson et al. |
| 2020/0306083 A1 | 10/2020 | Clauson et al. |

FOREIGN PATENT DOCUMENTS

| | | |
|---|---|---|
| CN | 201500225 U | 6/2010 |
| CN | 102271633 A | 12/2011 |
| CN | 102365058 A | 2/2012 |
| CN | 102512284 A | 6/2012 |
| CN | 202665790 U | 1/2013 |
| CN | 103025281 A | 4/2013 |
| CN | 103732172 A | 4/2014 |
| CN | 104736076 A | 6/2015 |
| EP | 0 994 281 A2 | 4/2000 |
| EP | 0870486 B1 | 11/2005 |
| FR | 2655836 A1 | 6/1991 |
| GB | 2536365 A | 9/2016 |
| GB | 2532596 B | 5/2017 |
| JP | 3069723 U | 6/2000 |
| JP | 2007014510 A | 1/2007 |
| RU | 2068251 C1 | 10/1996 |
| RU | 2143253 C1 | 12/1999 |
| RU | 31105 U1 | 7/2003 |
| RU | 2014124946 A | 12/2015 |
| WO | WO-99/59510 A1 | 11/1999 |
| WO | WO-2006/068650 A1 | 6/2006 |
| WO | WO-2007/011302 A1 | 1/2007 |
| WO | WO-2012/048348 A1 | 4/2012 |
| WO | WO-2016/036406 A1 | 3/2016 |
| WO | WO-2017/143272 A2 | 8/2017 |
| WO | WO-2018/081295 A1 | 5/2018 |
| WO | WO-2018/217579 A1 | 11/2018 |

OTHER PUBLICATIONS

U.S. Appl. No. 16/257,533, filed Jan. 25, 2019, US 2019-0151149.
U.S. Appl. No. 16/345,182, filed Apr. 25, 2019, US 2019-0282402.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.
U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/778,755, filed Jan. 31, 2020, US 2020-0289319.
U.S. Appl. No. 16/811,786, filed Mar. 6, 2020, US 2020-0306083.
U.S. Appl. No. 16/875,421, filed May 15, 2020, US 2020-0383833.
U.S. Appl. No. 16/875,426, filed May 15, 2020, US 2020-0360185.
PCT/US2020/16155, Jan. 31, 2020, WO 2020/160434.
PCT/US2020/33141, May 15, 2020, WO 2020/236593.
PCT/US2020/33142, May 15, 2020, WO 2020/247165.
U.S. Appl. No. 17/570,094, filed Jan. 6, 2022, US 2022-0233353.
"General Catalog for Inami Surgical Instrument." Inami & Co., Ltd. (1998) 2 pages. [English language translation].

(56) References Cited

OTHER PUBLICATIONS

"General Catalog for Inami Surgical Instrument." Inami & Co., Ltd. (1998) 2 pages. [Japanese language].
"Phaco-Section by Wire Snare—A New Technique of Non-Phaco Stitchless Surgery for Suprahard Cataracts." Basak, Samar K. (Jan. 30, 2013 published). URL: https://www.youtube.com/watch?v=CP8jrVb8qrg Retreived from YouTube.com. May 28, 2019. 1 page.
Bhattacharya, Debasish. (2009) "Nuclear management in manual small incision cataract surgery by snare technique." Indian J Ophthalmol. Jan.-Feb. 2009; 57 (1): 27-29.
Blumenthal, Michael et al. (1992) "Small-Incision Manual Extracapsular Cataract Extraction Using Selective Hydrodissection." Ophthalmic Surg., Oct. 1992; 23(10):699-701.

* cited by examiner

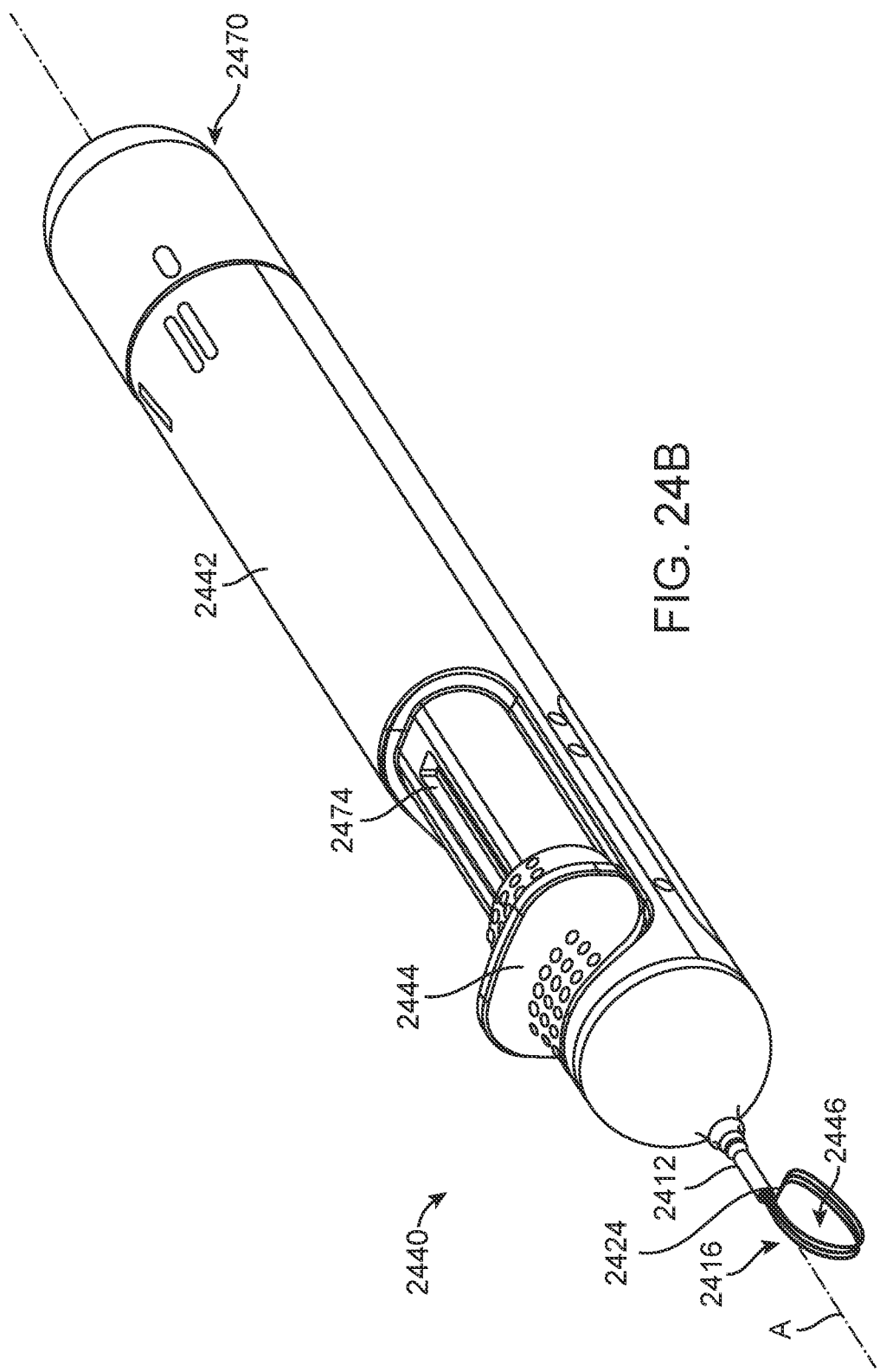

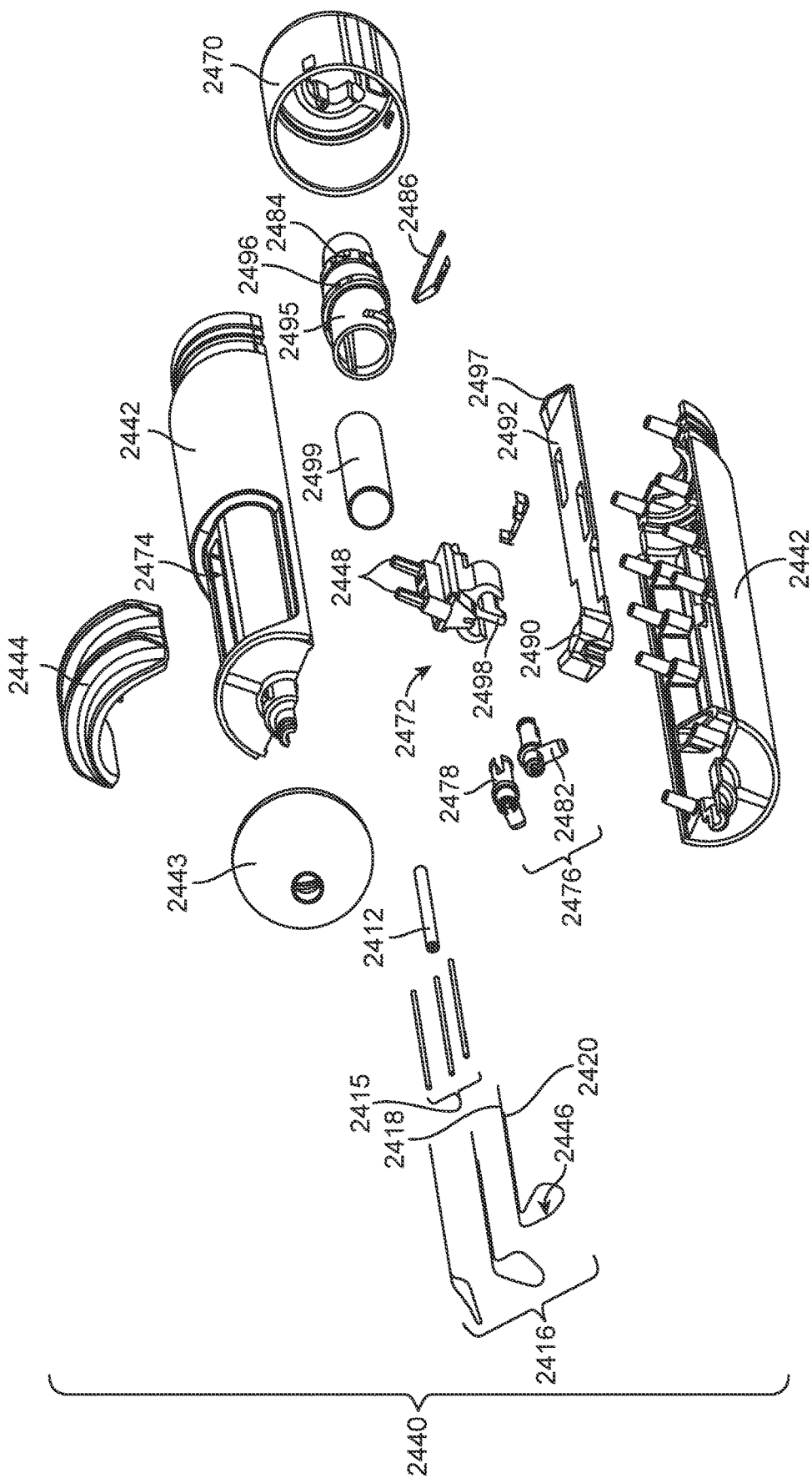

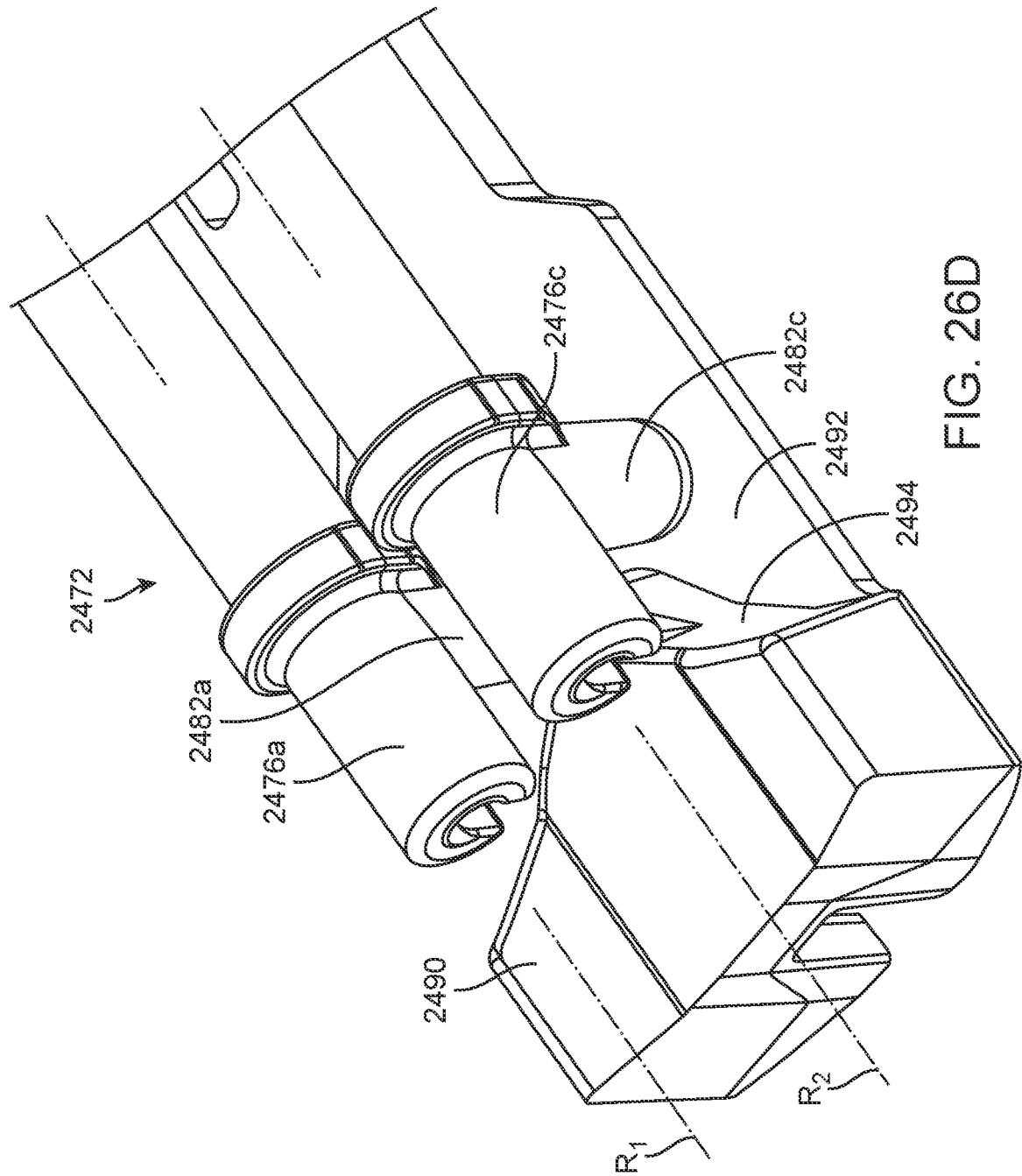

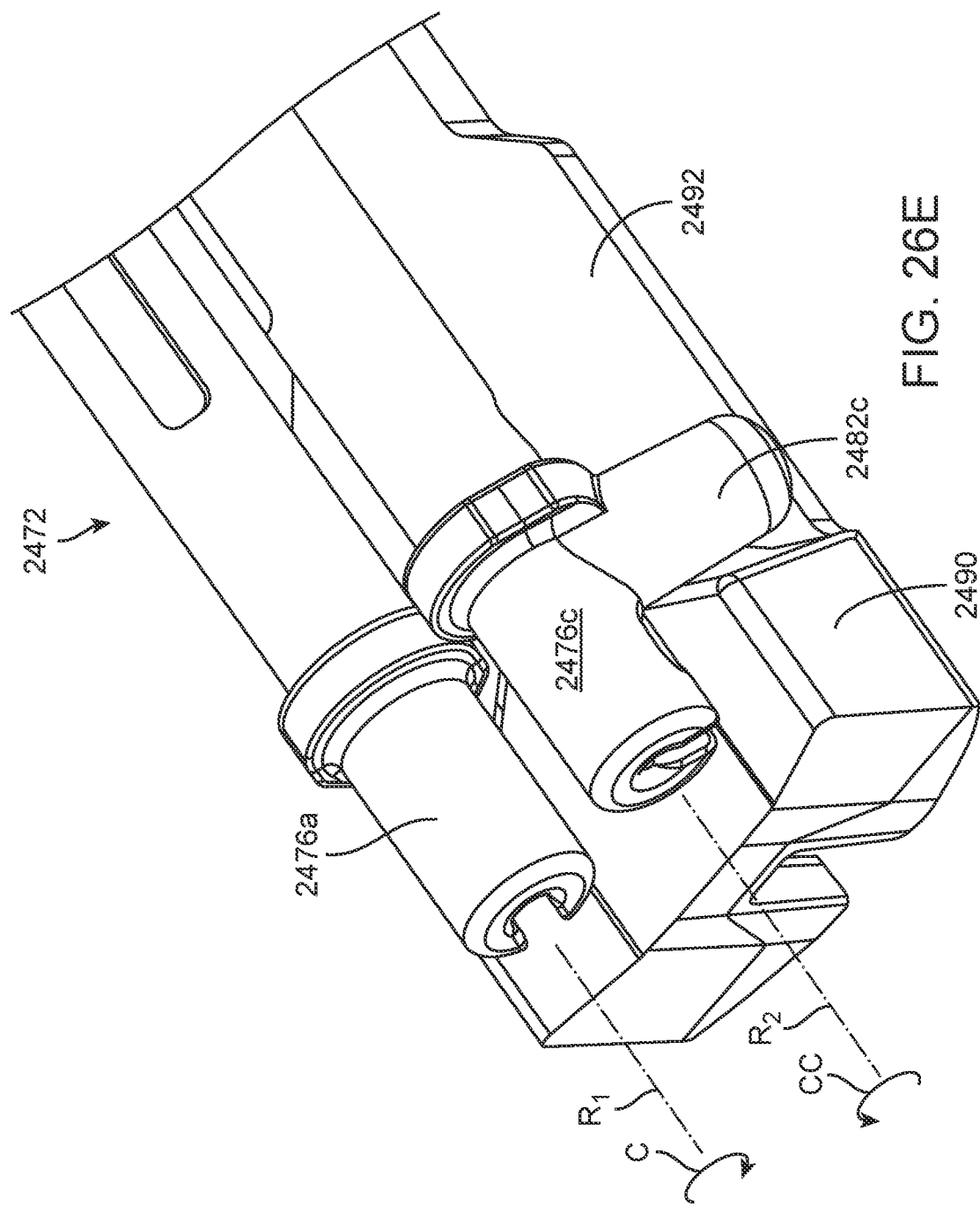

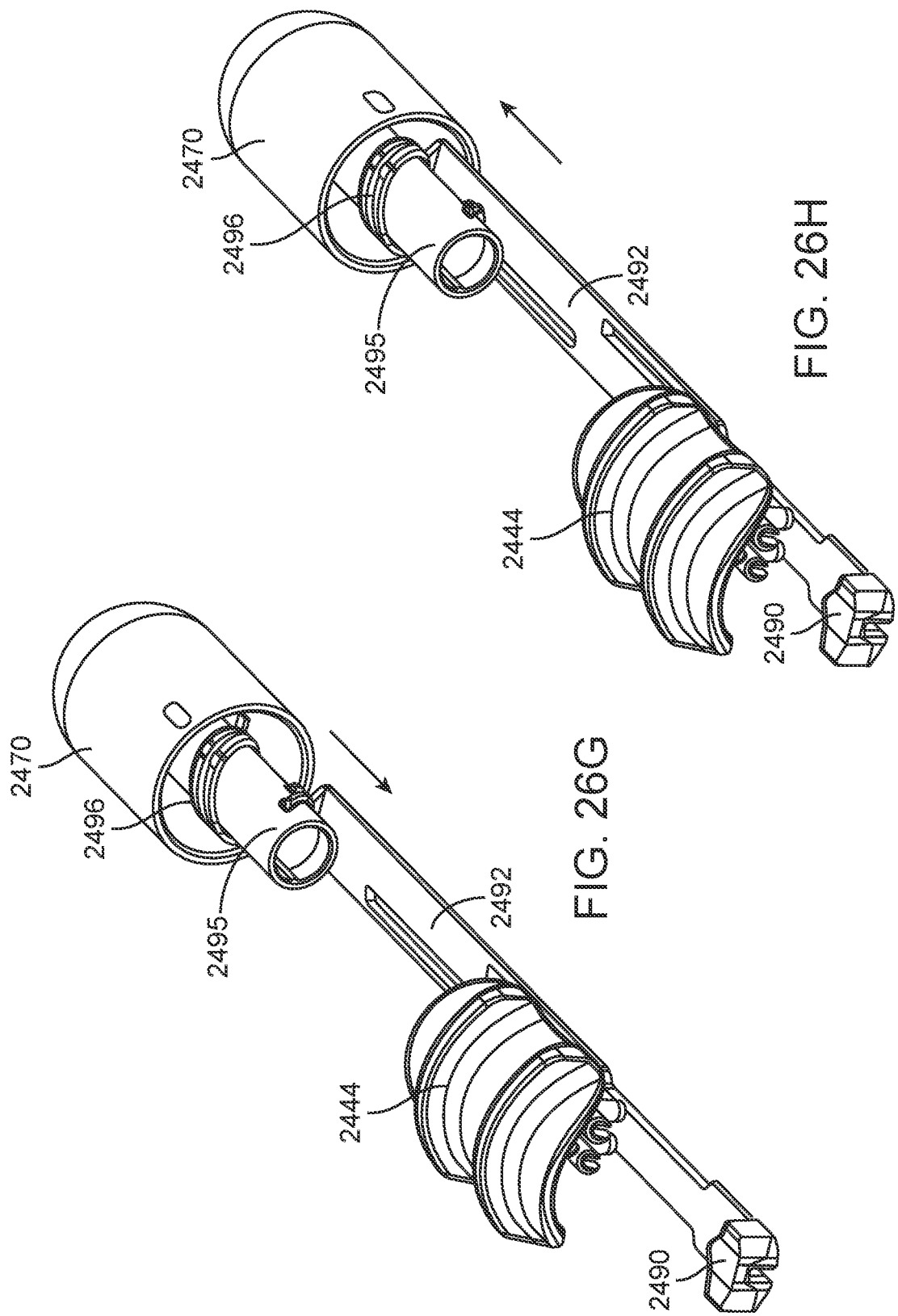

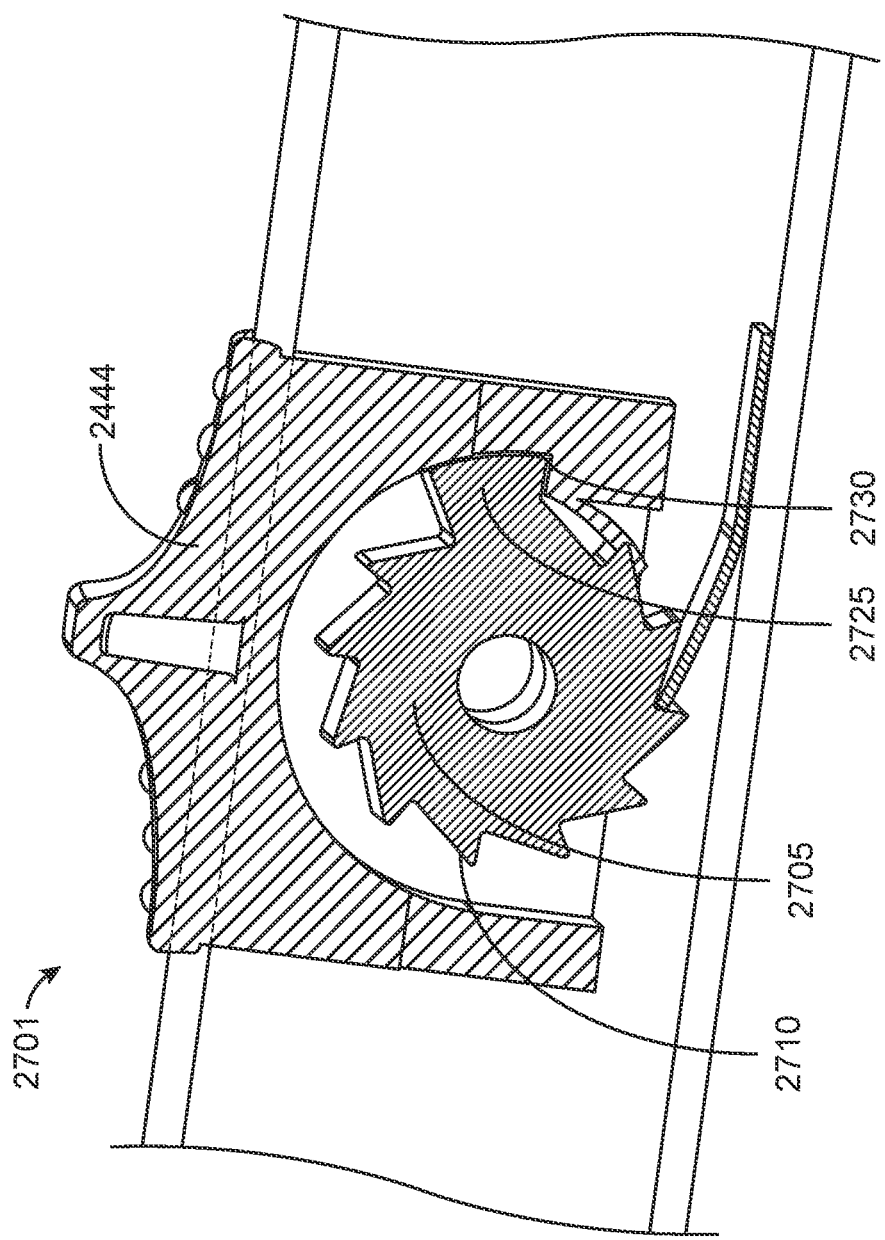

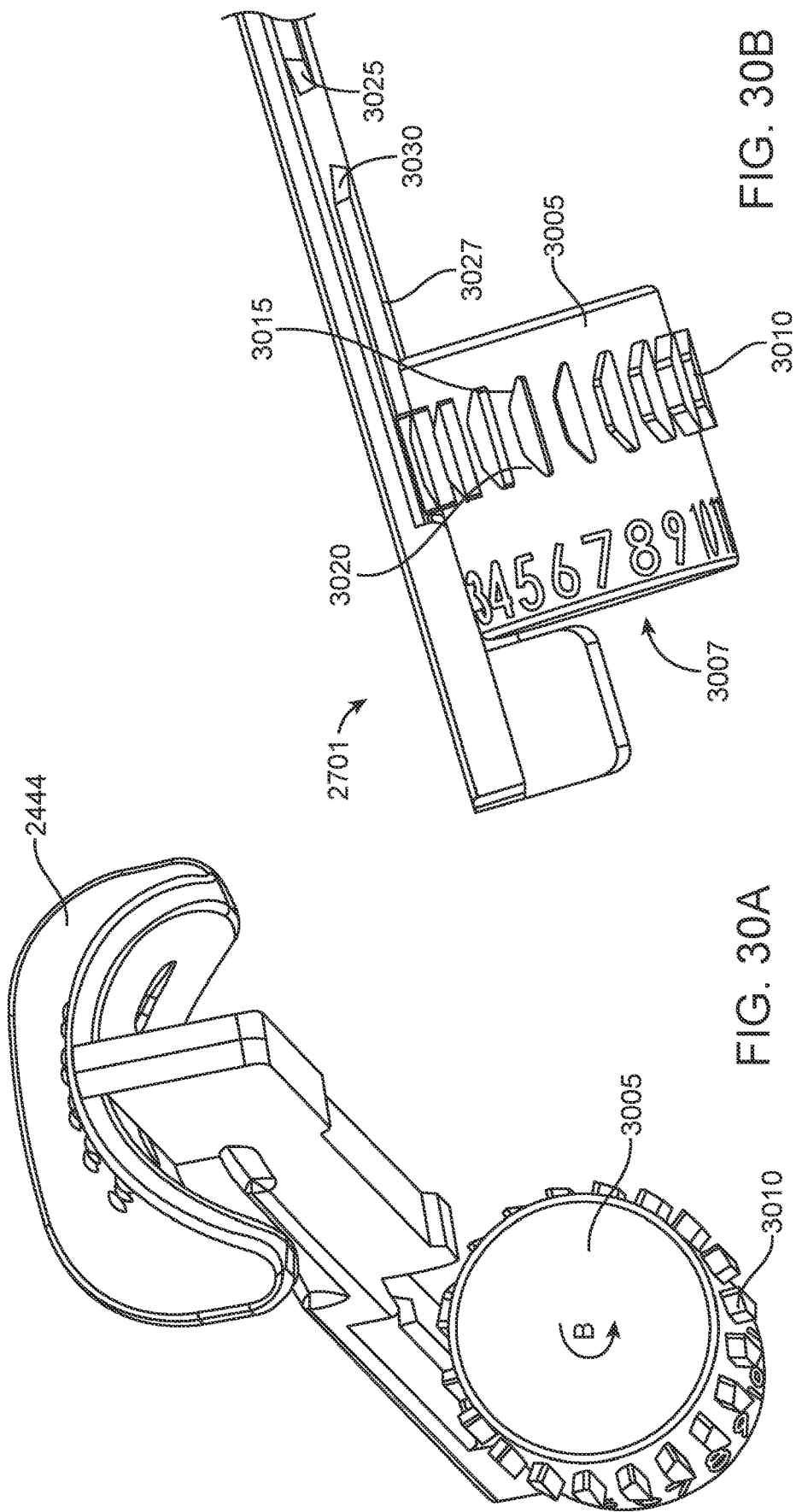

DEVICES AND METHODS FOR OCULAR SURGERY

CROSS-REFERENCE TO RELATED APPLICATIONS

This application is a continuation of co-pending U.S. application Ser. No. 16/221,239, filed Dec. 14, 2018, which claims priority to U.S. Provisional Patent Application Ser. Nos. 62/598,857, filed Dec. 14, 2017, entitled "Devices and Methods for Ocular Surgery", and 62/696,769, filed Jul. 11, 2018, entitled "Devices and Methods for Ocular Surgery," the disclosures of which are hereby incorporated by reference in their entireties for all purposes.

FIELD

The present technology relates generally to devices and methods for ocular surgery with one such procedure being removal of a lens from a human eye. More specifically, the technology relates to capturing, fragmenting and extracting of lenticular or other tissue in ophthalmic surgery.

BACKGROUND

Certain types of conventional ophthalmic surgery require breaking up lenticular tissue and solid intraocular objects, such as the intraocular lens into pieces so that it can be extracted from the eye. For example, extraction of lenses for cataract surgery is one of the most common outpatient surgical fields with more than 3 million cases performed annually in the United States alone. During cataract surgery a commonly used method for lens extraction is phacoemulsification, which incorporates using ultrasonic energy to break up the lens and then aspiration to remove the lens fragments through the instrument. Other methods of lens fragmentation and extraction may include the use of instruments such as hooks, knives, or laser to break up the lens into fragments and then extract through an incision in the cornea in an ab interno approach. Intraocular, ab interno fragmentation of the lenticular tissue is extremely important in cataract surgery in order to allow removal of cataracts from ocular incisions that are typically not exceeding 2.8-3.0 mm.

However, existing tools and techniques do not ensure full-thickness fragmentation of the lens. These techniques approach the lens from the anterior surface of the eye, and therefore the dissection forces exerted by mechanical instruments are limited such that they are often insufficient to accomplish a full-thickness segmentation. Further, due to the surgical approach through the incision at the edge of the cornea, a mechanical instrument is delivered at an angle substantially parallel to the plane defined by the capsulorhexis. As a result, a conventional surgical snare, loop or wire retrieval tool is not in an orientation in which that device could be looped around the lens to provide for fragmentation or extraction. Further, even if such a conventional tool could be looped around the lens, which it cannot, the wire of the snare would run the risk of applying excessive, damaging force to the capsular bag as it would be moved into position.

Energy-delivery instruments are limited in their ability to cut sections of the lens that are physically close to other delicate anatomical structures such as the capsular bag. For instance, a laser is generally not used to cut the posterior edge of the lens because it is in close proximity to the posterior edge of the capsular bag, leaving a lens that is not fully fragmented and must be fragmented carefully using secondary techniques.

For these reasons, phacoemulsification has become the most popular method of lens removal. However, phacoemulsification has its own drawbacks. As fluid and substances are aspirated from the capsular bag and the anterior chamber, other fluids such as saline are inspirated to maintain a constant volume or pressure. The flow of the fluids in the eye during inspiration and aspiration may create turbulent flow that may have a deleterious effect on the tissue within the eye, such as the corneal endothelium. The ultrasonic energy used in phacoemulsification can have its own negative consequences on ocular tissue. Further, phacoemulsification requires expensive and bulky capital equipment, limiting the locations in which phacoemulsification can be perform.

Additionally, certain aspiration and inspiration configurations require large pieces of capital equipment as in the case of phacoemulsification or may require certain resources such as wall vacuum that may not be available in all surgical settings, particularly in underdeveloped areas. A lower cost alternative with the same or better performance would also be desirable alternative such as one not requiring a costly control console and electronic control system.

SUMMARY

In an aspect, described is a surgical device for cutting a lens within a capsular bag of an eye. The device includes a shaft extending from a housing along a longitudinal axis of the device. The shaft has a lumen and a distal end. The device includes a cutting element movable through the lumen of the shaft. The cutting element includes a first sectioning element and a second sectioning element. Each of the first and second sectioning elements has a first end, a second end, and a distal loop formed between the first and second ends. The device includes an actuator operatively coupled to the cutting element. The cutting element is configured to transition from a first, retracted configuration towards a second, expanded configuration upon a first activation of the actuator. When in the second, expanded configuration, the distal loop of each of the first and second sectioning element defines an enlarged open area located outside the distal end of the shaft, the enlarged open area having a first leg advanced distally relative to the distal end of the shaft and a second leg positioned proximally to the distal end of the shaft.

When the cutting element is in the second, expanded configuration, the distal loops defining the enlarged open areas of each of the first and second sectioning elements can be aligned generally within a plane parallel to one another. A second activation of the actuator or a second, different actuator can cause the distal loop defining the enlarged open area of one of the first and second sectioning elements to move angularly relative to the plane transitioning the cutting element into a third, splayed configuration. A second activation of the actuator or a second, different actuator can cause the distal loop defining the enlarged open area of both of the first and second sectioning elements to move angularly away from one another transitioning the cutting element into a third, splayed configuration.

The device can further include an intermediate sectioning element positioned between the first and second sectioning elements. The intermediate sectioning element may also have a first end, a second end, and a distal loop formed between the first and second ends. When the cutting element is in the second, expanded configuration, the distal loop of the intermediate sectioning element can define an enlarged open area located outside the distal end of the shaft. The enlarged open area of the intermediate sectioning element can have a first leg advanced distally relative to the distal end of the shaft and a second leg positioned proximally to the distal end of the shaft. When the cutting element is in the second, expanded configuration, the distal loops defining the enlarged open areas of each of the first, second, and intermediate sectioning elements can be aligned generally within a plane parallel to one another. A second activation of the actuator or a second, different actuator can cause the distal loops defining the enlarged open areas of both the first and second sectioning elements to move angularly away from the intermediate sectioning element transitioning the cutting element into a third, splayed configuration. The first and second sectioning elements can move between about 15 degrees to about 45 degrees relative to the plane, the plane being a substantially vertical plane.

The first ends and the second ends of each of the first and second sectioning elements can be movable relative to the shaft. The first ends can be axially movable along the longitudinal axis of the device. The second ends can be angularly movable relative to the longitudinal axis of the device. The first ends of each of the first and second sectioning elements can be movable relative to the longitudinal axis of the device and the second ends of each of the first and second sectioning elements can be fixed relative to the longitudinal axis of the device. The first ends can be axially movable along the longitudinal axis of the device and angularly movable relative to the longitudinal axis of the device.

The actuator can be a slider movable along the longitudinal axis of the housing. The device can further include a sled positioned within the housing and coupled to move with the slider relative to the housing. The sled can include a first loop carrier coupled to the first sectioning element and a second loop carrier coupled to the second sectioning element. Movement of the slider a first distance in a distal direction relative to the housing can translate the sled distally causing the distal loops of the first and second sectioning elements to define the enlarged open areas and transition the cutting element towards the second, expanded configuration. Movement of the slider a second distance in the distal direction beyond the first distance can cause the distal loops defining the enlarged open areas of the first and second sectioning elements to move angularly away from one another transitioning the cutting element into a third, splayed configuration. The first loop carrier can be configured to rotate around a first axis of rotation in a first direction and the second loop carrier can be configured to rotate around a second axis of rotation in a second direction opposite the first direction. Rotation of the first loop carrier around the first axis of rotation can cause the distal loop of the first sectioning element to splay in the first direction and rotation of the second loop carrier around the second axis of rotation can cause the distal loop of the second sectioning element to splay in the second opposite direction. Movement of the slider a second distance in the distal direction beyond the first distance can rotate the first and second loop carriers around their axes of rotation transitioning the cutting element towards a third, splayed configuration. The device can further include a wedge positioned within a distal end region of the housing. Movement of the slider a second distance in the distal direction beyond the first distance can urge the first and second loop carriers against the wedge causing the first loop carrier to rotate around a first axis of rotation in a first direction and causing the second loop carrier to rotate around a second axis of rotation in a second, opposite direction resulting in the distal loops defining the enlarged open areas of the first and second sectioning elements to splay apart. The wedge can be immovable or can be movable in a proximal direction upon actuation of a second, different actuator. Movement of the wedge in a proximal direction can urge the wedge against the first and second loop carriers causing the first loop carrier to rotate around a first axis of rotation in a first direction and causing the second loop carrier to rotate around a second axis of rotation in a second, opposite direction resulting in the distal loops defining the enlarged open areas of the first and second sectioning elements to splay apart. The wedge can be movable in a proximal direction to cause splay of the first and second loop carriers independent of a relative location of the sled along the longitudinal axis of the device.

When the cutting element is in the second, enlarged configuration, the distal loops defining the enlarged open areas of the first and second sectioning element can be generally oval in shape and have a maximum width of about 4.0 mm to about 20 mm, and a maximum height of about 1.0 mm to about 15 mm. The distal loops defining the enlarged open areas of the first and second sectioning elements can be configured to splay angularly away from each other transitioning the cutting element into the third, splayed configuration independent of a size of the enlarged open areas. The size of the enlarged open areas of the first and second sectioning elements prior to splay can be selectable. The device can further include an adjustor configured to change a relative distance between the wedge and the sled. A shorter relative distance can achieve a smaller open area of the first and second sectioning elements in the second, expanded configuration prior to splay, and a longer relative distance can achieve a larger open area of the first and second sectioning elements prior to splay.

In an interrelated implementation, described is a surgical device for cutting a lens within a capsular bag of an eye that includes a shaft extending from a housing along a longitudinal axis of the device. The shaft has a lumen and a distal end. The device includes a cutting element movable through the lumen of the shaft. The cutting element includes at least a first sectioning element having a first end, a second end, and a distal loop formed between the first and second ends. The device includes a slider operatively coupled to the cutting element and movable along the longitudinal axis of the housing. The device includes a stroke counting mechanism coupled to the slider and contained within the housing. The cutting element is configured to transition from a first, retracted configuration towards a second, expanded configuration upon distal extension of the slider. When in the second, expanded configuration, the distal loop of the at least a first sectioning element defines an enlarged open area located outside the distal end of the shaft, the enlarged open area having a first leg advanced distally relative to the distal end of the shaft and a second leg positioned proximally to the distal end of the shaft. The stroke counting mechanism is configured to track distal extensions and/or proximal extensions of the slider.

The stroke counting mechanism can be configured to cause a lock-out event that prevents distal extension of the slider after the lock-out event. The stroke counting mechanism can include a cylindrical counting barrel having a plurality of ramp blocks; a hard stop; and a pair of slider ramps shaped and arranged to engage with the plurality of ramp blocks on the counting barrel causing the counting barrel to rotate around the longitudinal axis of the device. Each distal extension of the slider can turn the cylindrical counting barrel a fraction of a full revolution around the longitudinal axis of the device. The cylindrical counting barrel can be configured to turn up to about 24 fractions before the lock-out event occurs. The lock-out event can prevent distal extension of the slider and allows proximal retraction of the slider. The slider can be configured to extend about 3 to about 30 strokes in a distal direction before the lock-out event occurs and the slider is locked in a rearward position.

The device can include a lock-out warning feature. The lock-out warning feature can include a lock-out warning window extending through the housing providing a visible indication of a position of the counting barrel within the housing relative to the hard stop of the stroke counting mechanism. The counting barrel can be axially movable within the housing and have an outer surface having a color that contrasts with a color of the housing. When the counting barrel is positioned near the lock-out warning window, the color of the counting barrel can be visible through the lock-out warning window providing an indication of the distal extensions of the slider available before the lock-out event occurs. The counting barrel can have a series of markings on an outer surface and be fixed relative to the lock-out warning window. The series of markings can indicate a number of distal extensions performed by the slider.

The slider can further include a shutter window. When the slider is moved toward a distal end region of the housing, the shutter window of the slider and the lock-out warning window of the housing can align revealing the series of markings on the barrel. When the slider is moved proximally away from the distal end region of the housing, the shutter window of the slider and the lock-out warning window of the housing may not align and the series of markings on the barrel are not visible.

BRIEF DESCRIPTION OF THE DRAWINGS

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIG. 24B is a perspective view of the device of FIG. 24A in a second, expanded configuration.

FIG. 26A is an exploded view of the device of FIG. 24A include a two-phase deployment mechanism.

FIG. 26D is a partial, perspective view illustrating the loop carrier of the device of FIG. 24A prior to splay.

FIG. 26E is a partial, perspective view illustrating the loop carrier of the device of FIG. 24A after splay.

FIGS. 26G-26H illustrates an expansion adjustment mechanism of the device of FIG. 24A.

FIGS. 27A-27C illustrate an implementation of a stroke counting mechanism.

FIGS. 30A-30E illustrate another implementation of a stroke counting mechanism.

It should be appreciated that the drawings are for example only and are not meant to be to scale. It is to be understood that devices described herein my include features not necessarily depicted in each figure.

DETAILED DESCRIPTION

Described herein are methods and devices for intraocular fragmentation and removal of the lens and other tissues during intraocular surgery. The devices described herein allow for extracting tissue from the anterior chamber without damaging other ocular structures. In various implementations, an ocular surgical device is described that uses cutting strings, loops, filaments, snares, and the like that are designed to engage and fragment the lenticular tissue and aid in its removal from the eye in a minimally-invasive, ab interno approach. In one aspect, provided is a hand-held device that can also be powered (manually) by the user and does not require electronic control. The devices described herein are configured for fully adjustable and customizable deployment that can occur in a two-step manner (i.e. expansion and rotation or expansion and splay) or a three-step manner (i.e. expansion, rotation, and splay).

Figure 1:
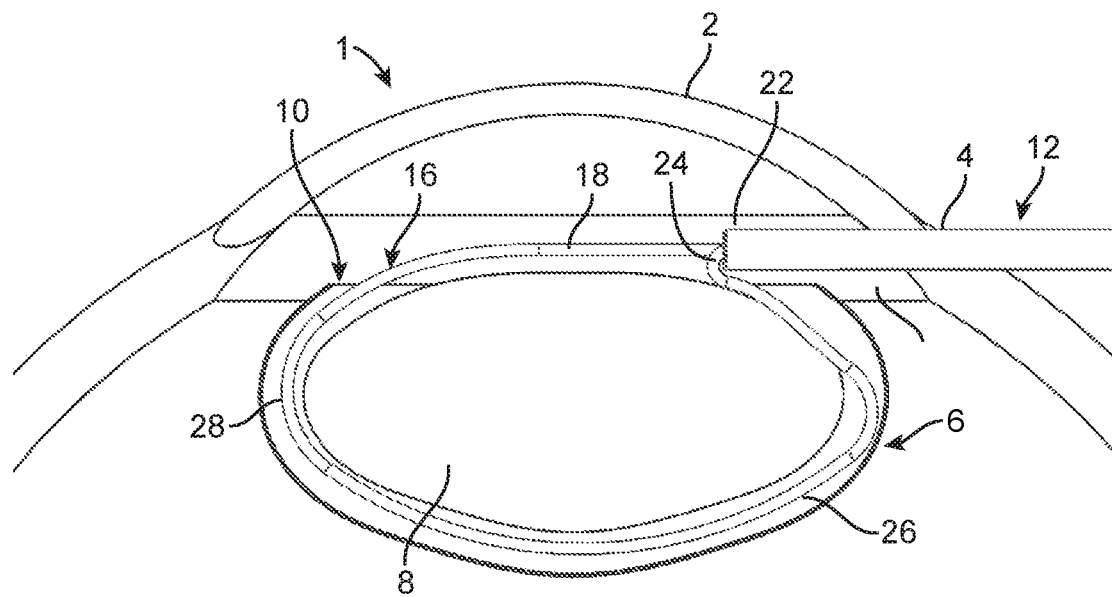
FIG. 1 is a side schematic view of the ocular anatomy, showing the insertion of a shaft and sectioning element through an incision in the side of the cornea.

Referring now to the figures, FIG. 1 shows the normal anatomy of the eye 1 including a cornea 2, capsular bag 6, and a lens 8 within the capsular bag 6. During a cataract procedure, an incision 4 can made in the edge of the cornea 2 to access the capsular bag 6. The surgeon forms a capsulorhexis 10 on the anterior surface of the capsular bag 6. The capsulorhexis 10 can be performed in any suitable manner, such as incising with a scalpel, applying energy with a femtosecond laser or other energy-based cutter, incising under robotic or automated control, or in any other suitable manner. The capsulorhexis 10 can be torn or cut in a diameter of approximately 2.0 mm to 8.0 mm. The capsulorhexis 10 may be made smaller in diameter than 2.0 mm, particularly where fragments of the lens 8 (as described in greater detail below) are small enough in size to be extracted through a smaller-diameter capsulorhexis 10. The capsulorhexis 10 can be made with a separate set of instruments such as micro-forceps, as is commonly done. It is desirable to maintain the size of the corneal incision to a minimum. For example, corneal incisions that are self-sealing and require no stitches for closure are optimal for minimally-invasive surgery with the least risk for complications. The devices described herein are designed to minimize the size of incision needed to perform lens fragmentation and removal.

Figure 3:
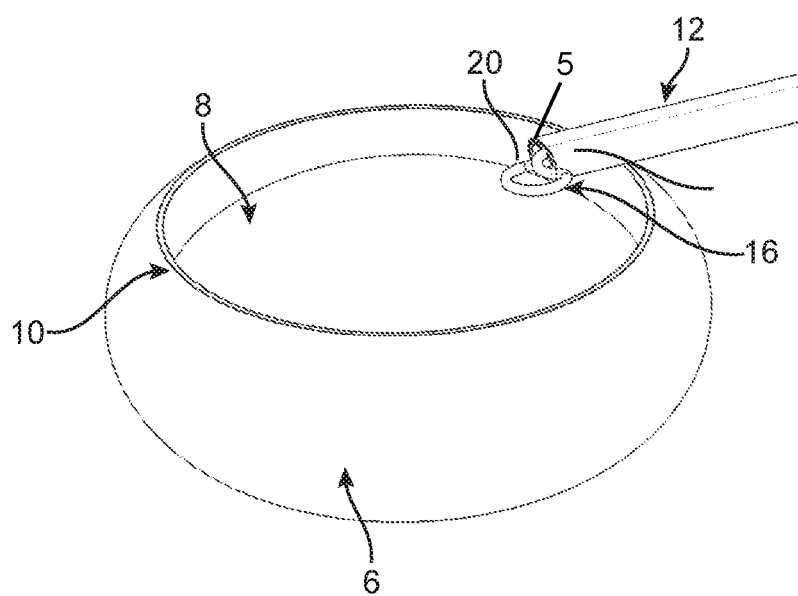
FIG. 3 is a perspective view of the capsular bag, with a completed capsulorhexis, with a sectioning element in a first, retracted configuration for insertion.

Referring also to FIG. 3, a shaft 12 is then inserted through the incision 4 in the cornea 2. As seen in FIG. 3, the distal end of the shaft 12 is positioned above (i.e., anterior to) the capsulorhexis 10, spaced apart from the capsulorhexis 10 but positioned within the circumference of the capsulorhexis 10 as viewed from outside the eye 1. As seen in FIG. 1, the shaft 12 is generally parallel to the plane defined by the edges of the capsulorhexis 10 upon its insertion through the incision 4 in the cornea 2. In some embodiments, the distal end of a sectioning element 16 extends out of an outlet 5 in a lumen 14 at the distal end of the shaft 12 in a first, retracted configuration. In such embodiments, the tight radius bend 24 may be positioned outside the shaft 12, already bent at least partially toward the proximal direction. In this way, even in embodiments where the sectioning element 16 is fabricated from superelastic material, the angle through which portions of the sectioning element 16 are bent during transition from the first, retracted configuration to the second, expanded configuration is reduced. Further, less space is required within the lumen 14 of the shaft 12 to hold part of the sectioning element 16 than to hold all of it, allowing the shaft 12 to be made smaller in diameter. According to some embodiments, the shaft 12 is an ovular cross-section tube with a rounded tip. The ovular cross-section enhances the ability of the shaft 12 to be inserted into the eye 1 through the corneal incision 4. Additionally, in the event that there are multiple sectioning elements, they may be arranged side-by-side more easily in the lumen 14 of an ovular cross-section shaft 12. Alternately, the shaft 12 may have a circular cross-section or a cross-section of any other suitable shape. The proximal end of the sectioning element 16 extends through the lumen 14 of the shaft 12. Alternately, the entirety of the sectioning element 16 is positioned within the lumen 14 of the shaft 12 in the first, retracted configuration. Alternately, more than one sectioning element 16 is utilized, where each sectioning element 16 is initially in the first, retracted configuration. While a single sectioning element 16 is described with regard to this particular embodiment for clarity, it will be apparent in light of the further disclosure below that any suitable number of sectioning elements 16 may be provided and used in a single lens removal procedure, and that the devices and methods herein are not limited to the use of any particular number of sectioning elements 16. Related devices having sectioning elements as described herein are described in U.S. Pat. Nos. 9,775,743 and 9,629,747, which are each incorporated by reference herein in their entireties.

According to some embodiments, the sectioning element 16 includes a first end 18 and second end 20. As described in greater detail below with regard to FIGS. 16-22, one of the ends 18, 20 of the sectioning element 16 may be movable relative to the shaft 12, while the other of the ends 18, 20 of the sectioning element 16 may be fixed relative to the shaft 12. For example, the second end 20 of the sectioning element 16 may be fixed relative to the shaft 12 and the first end 18 of the sectioning element 16 may be slideable relative to the shaft 12. The second end 20 may be connected to the shaft 12 or to other structure by crimping, welding, adhesives, mechanical interlocks, or any other suitable structure or method. In some embodiments, the sectioning element 16 is a wire with a circular, oval or other atraumatic cross-section. In other embodiments, the sectioning element 16 is a strap. As used in this document, a strap is a structure that is wider than it is thick, as viewed longitudinally.

In the first, retracted configuration, where the distal end of the sectioning element 16 extends distally out of the shaft 12, the sectioning element 16 is sized and shaped to pass through a standard corneal incision 4 without damaging the eye 1. The corneal incision 4 is generally 3.5 mm or less in width and made with a small knife. Thus, the outer diameter of the shaft 12 advantageously is 3.5 mm or less. Where a differently-sized incision 4 is used, a different outer diameter of shaft 12 may be used, keeping in mind that it is most desirable to form the incision 4 as a line 5 mm or less in length. In other embodiments, the sectioning element 16 is positioned completely within the lumen 14 of the shaft 12 such that it is within the inner diameter of the shaft 12 as the shaft 12 is inserted through the incision 4, and is then extended out of the shaft 12 once in the eye. Alternatively, additional components may be used to sheathe the sectioning element 16 during insertion through the corneal incision 4. The device can include a thin-walled, retractable sleeve or sheath that restricts movement of the sectioning element 16 away from the longitudinal axis A of the device during certain times of use (i.e. during insertion, expansion and/or prior to splay of multiple sectioning elements relative to one another). In some implementations, a tapered piece may be positioned on the distal end of the shaft 12 that gradually tapers from the end of the shaft 12 down to a smaller cross section such that it can aid insertion through the corneal incision 4. The tapered piece can also cover the sectioning element 16 to constrain it during insertion. The tapered piece can further have a slit in the front that the sectioning element 16 can extend through or tear open once it has passed through the incision 4.

According to some embodiments, the sectioning element 16 is fabricated from of a flexible or superelastic material, such as nickel-titanium alloy, which allows the sectioning element 16 to bend and flex as it is inserted into the eye 1 through the corneal incision 4. The sectioning element 16 can also be formed from other materials such as a polymer rather than metal. In these embodiments, the constricted shape of the sectioning element 16 may be larger in one or more dimensions than the corneal incision 4, and flexes to pass through the incision 4 as the shaft 12 moves toward the capsulorhexis 10. Alternatively, the sectioning element 16 may not have a first, retracted configuration, and may be inserted through the incision 4 in the same configuration that is later utilized to engage the lens 8. In such embodiments, the sectioning element 16 compresses as it passes through the corneal incision 4 and then re-expands once it enters the eye 1. In still other embodiments, the sectioning element 16 may not have a first, retracted configuration, and may be inserted through the incision 4 in a larger configuration than is later utilized to engage the lens 8. In still other embodiments, the sectioning element 16 may be hooked, rotated, or otherwise inserted through the corneal incision 4 in any number of methods.

Figure 4:
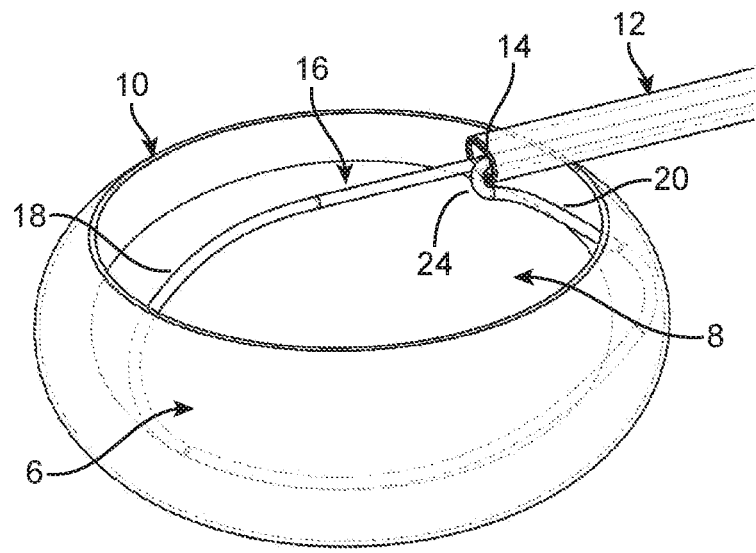
FIG. 4 is a perspective view of the capsular bag, with a completed capsulorhexis, with a sectioning element in a second, expanded configuration for capture.

Referring to FIG. 4, the sectioning element 16 or elements are pushed distally relative to the lumen 14 of the shaft 12. As set forth above, one end 20 of the sectioning element 16 may be fixed, such that the other end 18 of the section element 16 is pushed distally relative to the lumen 14 of the shaft 12. As a result, the sectioning element 16 moves from a first, retracted configuration to a second, capture configuration.

The sectioning element 16 may be fabricated from any suitable material. For example, as discussed above, shape memory materials such as nickel-titanium alloy may be used to allow the sectioning element 16 to move to its predefined shape in the second, expanded configuration, with a high amount of elasticity. In one embodiment, the nickel-titanium alloy may be used in its superelastic condition, where the nickel-titanium alloy transforms its crystal structure to move from the first, retracted configuration to the second, expanded configuration. In other embodiments, the sectioning element 16 is fabricated from nickel-titanium alloy that is shape set to move from the first, retracted configuration to the second, capture configuration upon reaching a transition temperature that is above room temperature but below body temperature. The sectioning element 16 fabricated from nickel-titanium alloy thus may enter the eye at room temperature below its transition temperature such that it will hold a constricted shape. As the sectioning element 16 is placed into the eye 1 and allowed to warm to body temperature, the nickel-titanium alloy may become warmer than its transition temperature and begin to return to its predefined second, expanded configuration. This shape change may happen over a period of time that allows the surgeon to place the sectioning element into the capsular bag 6 and orient it while the shape changes such that the loop can define a sectioning plane through the lens. Alternatively, any other number of biocompatible materials may be considered such as stainless steel or non-metal polymer materials. In some embodiments, the nickel-titanium alloy may be warmed actively by the surgical device 40, in which case the transition temperature of the sectioning element 16 may be selected to be greater than room temperature but less than a temperature that would damage the tissue of the capsular bag 6 or other tissue of the eye 1. Other shape memory materials such as shape memory plastics may be utilized instead of nickel-titanium alloy. Alternatively, any other number of biocompatible materials may be considered such as stainless steel, titanium, silicone, polyimide, PEBAX® polyether block amide, nylon, polycarbonate, or any other suitable material. Furthermore, multiple materials joined end to end or in laminated layers or concentric tubes of material may be used.

Referring also to FIGS. 1 and 4, in the second, expanded configuration, the sectioning element 16 is specifically shaped for lens capture. According to some embodiments, the second, expanded configuration is a preset shape of the sectioning element 16, such as through the use of elastic or superelastic materials to fabricate the sectioning element.

As seen most clearly in FIG. 4, in the second, expanded configuration, the sectioning element 16 approximates an irregular loop that is generally shaped like the cross-section of a lens 8, and that is shaped and sized to surround the lens 8 within the capsular bag 6. As set forth above, in some embodiments, the sectioning element 16 is fabricated from a length of round wire. The second, expanded configuration of the sectioning element 16 has a merging point 22 where the first end 18 and second end 20 of the sectioning element 16 merge back together, forming a shape with a perimeter so that the device 40 approximates a closed loop 21. The "merging" refers to placing the first end 18 and second end 20 of the sectioning element 16 into proximity with one another. The merging point 22 may be located at or in proximity to the distal end of the shaft 12. In the second, expanded configuration, the sectioning element includes a distal portion 28 that extends distal to the merging point 22 and a proximal portion 26 that extends proximally to the merging point 22. The merging point 22 in this exemplary embodiment is at a point above the surface of the lens and within the circle defined by the capsulorhexis 10 at the top of the capsular bag 6. In some embodiments, the proximal portion 26 of the sectioning element 16 may include a tight radius bend 24 as shown in FIG. 1. The tight radius bend 24 bends the second end 20 of the sectioning element 16 proximally such that the second end 20 extends proximally from the merging point 22. Alternatively, the sectioning element 16 may take a different path to achieve this path transition without such a sharp radius bend. For example, paths that are outside of the normal plane of FIG. 1 such as curves or oscillations may be incorporated to reduce the overall bend radius of the proximal portion 26 of the sectioning element 16. This may improve the ability of the sectioning element 16 to change shape into other smaller constricted configurations as will be discussed below.

The first end 18 and/or second end 20 is pushed out of the lumen 14 of the shaft 12, while the other end is fixed relative to the shaft 12, as described above. Alternatively, both ends 18, 20 of the sectioning element 16 are movable relative to the shaft 12 and configured to slide relative to the lumen 14 of the shaft 12. Alternatively, the shaft 12 may be the sliding component while the sectioning element 16 remains stationary. As the end or ends 18, 20 (sometimes referred to as "legs") are pushed outward from the lumen 14, the sectioning element 16 transitions to the second, expanded configuration. As the sectioning element 16 transitions, the tight radius bend 24 allows the proximal section of the sectioning element to extend proximally from the distal end of the shaft 12, at a location spaced from and to one side of (i.e. off-set from) the longitudinal centerline of the lumen 12 in the direction toward the capsular bag 6. In this way, the sectioning element 16 is able to extend downward through the capsulorhexis 10 and expand to a length within the capsular bag 6 that is greater than the diameter of the capsulorhexis 10, as seen in FIG. 1. According to some embodiments, the tight radius bend 24 results in the second end 20 having an angle of at least 120 degrees relative to the longitudinal centerline of the shaft 12, and relative to the distal direction, as seen in FIG. 1. Both the distal portion 28 and the proximal portion 26 of the sectioning element 16 in the second, expanded configuration are gently curved and generally approximate the size and shape of the lateral sides of the capsular bag 6, in order to enter the capsular bag 6 without causing damage (e.g., such as a capsular tear or hole, over-stretching the capsular bag, or damaging the inner surface of the capsular bag tissue).

Figure 2:
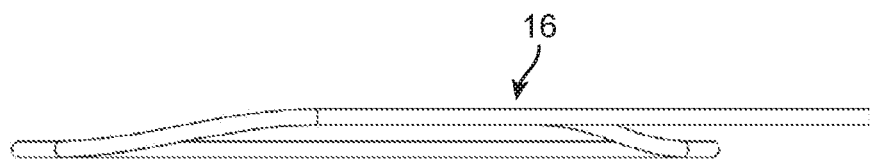
FIG. 2 is a top view of the sectioning element in a deployed position.

Referring also to FIG. 2, the shape of the sectioning element 16 in the second, expanded configuration forms a plane that is generally flat or horizontal with respect to the top lens surface, according to some embodiments. Referring back to FIGS. 1 and 3, with the correct orientation, the sectioning element 16 is held such that it opens through the capsulorhexis 10 into the capsular bag 6. As the sectioning element 16 continues to expand, the plane formed by the sectioning element 16 can be rotated so that the sectioning element traverses a space between the capsular bag and the lens. The plane includes the longitudinal axis of the lumen 14 of the shaft 12. Alternately, the shape of the sectioning element 16 in the second, expanded configuration is a more three-dimensional shape that does not lie in a single plane. For example, the sectioning element 16 may oscillate in and out of a flat plane, or may be substantially curved out of a flat plane in one direction or another. The rotation may be accomplished by manual rotation of the shaft 12 of surgical device 40 by the user, or may be accomplished by integrated mechanisms within the surgical device 40, as described in greater detail below. Referring also to FIG. 4, the sectioning element 16 has proceeded most of the way from the first, retracted configuration to the second, expanded configuration, and has been rotated partially relative to the lens 8. The sectioning element 16 may be rotated such that the shape plane is primarily vertical or to any number of other angles. Mechanisms and methods for producing such rotation are described in greater detail below. Additionally, multiple sectioning elements 16 may be used that rotate to a variety of angles. In other embodiments, the rotation does not occur until the sectioning element 16 transitions to the second, expanded configuration. According to some embodiments, rotation begins while the sectioning element 16 transitions to the second, expanded configuration. For example, rotation may begin once an open area 46 of the loop and within the sectioning element 16 expands to a size in which a 5-6 mm chord extends across the open area 46 between two points on the proximal portion 26 and the distal portion 28. As another example, rotation may begin when the chord is longer than, or shorter than 5-6 mm.

The second, expanded configuration of the sectioning element 16 may be generally ovular in shape, referring to FIG. 1, with a width 7.0 mm-15 mm and a height of 3.0-10 mm, according to some embodiments. According to other embodiments, the width of the sectioning element 16 may be 4.0-20 mm with a height of 1.0-15 mm. In some embodiments the size of the second, expanded configuration of the sectioning element 16 may be intentionally smaller than the size of the lens at certain areas or along the entire profile. This may improve the ability of the sectioning element 16 to remain close to the lens 8 and reduce interaction with the capsular bag 6. For example, the second, expanded configuration of the sectioning element 16 may be 12 mm wide and 4.0 mm high. This may allow clearance between the sectioning element 16 and the lens 8 at the width of the oval while maintaining interference along the height of the oval that may reduce the likelihood of damaging the posterior surface of the capsular bag 6. That is, by configuring the second, expanded configuration of the sectioning element 16 to engage a portion of lens 8, rather than move to a position in which it encircles the thickest part of the lens 8, the sectioning element 16 is sized smaller, and engages less of the capsular bag 6, than a configuration in which the second, expanded configuration of the sectioning element 16 is able to encircle the thickest part of the lens 8. In other embodiments, the second, expanded configuration of the sectioning element 16 is predefined to have a generally specific clearance around the lens 8. According to some embodiments, the second, expanded configuration of the sectioning element 16 has a different shape than generally oval.

The sectioning element 16 may have features or geometry that further prevents the element from damaging the capsular bag. For example, the sectioning element 16 is a round wire of sufficient diameter to reduce the likelihood of tearing or damaging the capsular bag 6, according to some embodiments. The diameter of that round wire may be 0.004"-0.012" but may also be any size that prevents excessive stress from being placed on the capsular bag 6, such as 0.001"-0.030" diameter. Alternatively, the profile of the sectioning element 16 may be ovular with a larger width or height, or may be a strap, to further distribute the force of the sectioning element 16 on the capsular bag 6 over a larger surface area, thereby reducing or eliminating areas of high pressure exerted on the capsular bag 6 by the sectioning element.

In some embodiments, portions of the outer surface of the sectioning element 16 may be coated to improve certain aspects of the device. For example, as discussed in greater detail below, the sectioning element 16 traverses a space between the capsular bag 6 and the lens 8. As the sectioning element 16 moves between these anatomical structures it may be advantageous to have a more hydrophilic or hydrophobic surface so the sectioning element 16 rotates and moves more freely. In one embodiment, the sectioning element 16 may be coated with a hydrophobic material such as a fluoropolymer; for example, PTFE. A coating can be added through dip coating, plasma vapor deposition process, heat shrink sleeves, or any other suitable method. The coating can reduce the friction between the sectioning element 16, and the lens 8 and/or capsular bag 6, to allow the sectioning element 16 to move more freely. Other methods of reducing the friction may include using mechanical abrasion, plasma treatments, or any other suitable method. Alternatively, the sectioning element 16 may be coated with other materials such as active pharmaceutical agents that are configured to release into they during the procedure. For example, a steroid like triamcinolone may be added to the surface of the sectioning element 16 such that during the procedure it releases into the eye. Any other number of coatings and drugs may be contemplated.

The sectioning element 16 may be constructed with any other suitable geometries or materials. In an exemplary embodiment, the sectioning element 16 is a round wire. The wire is configured to bluntly traverse a space between the lens 8 and the capsular bag 6. The wire can have various sizes or diameters along the length of the sectioning element 16. Alternatively, the sectioning element 16 may be any number of other profiles. For example, the sectioning element 16 could be a tube, a ribbon, a strap, a wire with a hexagonal profile, or any other number of suitable shapes. In addition, the profile of the sectioning element 16 could change along its length. For example, the sectioning element 16 may include one or more padded areas along its profile where damage to the capsular bag 4 is of particular concern. The padded areas may include different materials, such as but not limited to soft elastomeric materials like silicone that are bonded or coated onto appropriate areas of the sectioning element 16. The padded areas may distribute the force over a larger area, and provide a softer and more atraumatic interface against the capsular bag 6. In other embodiments, the padded areas are geometry profile changes of the sectioning element in certain areas. For example, areas that are flared out or broadened, even if comprised of the same material, distribute the force over a larger area. Additionally, the stiffness or flexibility of the sectioning element may vary over the sectioning element 16 by changing the material thickness or wire diameter in certain areas. Alternatively, sleeves or other materials may be added to the sectioning element 16 to increase stiffness locally in certain areas. In still other embodiments, the sectioning element 16 may have cuts or ribs along its length that change its flexibility or stiffness in certain areas.

In other embodiments, the shape of the sectioning element 16 in the second, expanded configuration is not predetermined. Instead shape of the sectioning element 16 in the second, expanded configuration is defined by the material or geometric properties of the sectioning element 16, engaged with the lens 8. The sectioning element 16 may be sufficiently flexible, elastic, soft, or blunt along its length, while maintaining sufficient stiffness to allow for rotation to engage the lens 8, such that minimal force is applied to the capsular bag 6 even when the sectioning element 16 is within the capsular bag 4 and fully opened. In other embodiments, the sectioning element 16 may be a soft elastomer such as silicone that may be sufficiently soft and large enough in diameter so that the sectioning element 16 does not place excessive force onto the capsular bag 6. In still other embodiments, the sectioning element 16 may be sufficiently blunt along certain portions and edges such that the force applied to the capsular bag 6 is distributed over a larger area and therefore the tearing pressure may be reduced. In still other embodiments, the sectioning element 16 may be comprised of a linkage of multiple elements, for example a chain-like structure, allowing for flexible movement between the multiple elements. In still other embodiments, the sectioning element 16 may have slits along portions of its length that locally may increase its flexibility. For example, the sectioning element 16 may include a tube with cutouts along its length at areas where the capsular bag 6 may come in contact with the sectioning element 16 such that these areas are more flexible and therefore are less prone to putting excessive force onto the capsular bag 6. In still other embodiments, portions of the sectioning element 16 in the second, expanded configuration are not predetermined in shape, while other portions of the sectioning element 16 are predetermined in shape. For instance, a portion of the sectioning element 16 anterior to the lens may be fabricated from a shape memory round wire that is shape-set to a predefined shape that aids in guiding the sectioning element 16 into the eye. For example, such a portion can include the tight radius bend 24 of the proximal portion 26. A portion of the sectioning element 16 posterior to the lens 8 may be fabricated from a different, more-flexible material that more easily conforms to the shape of the eye. In this way, the portion of the sectioning element 16 in the second, expanded configuration that allows for insertion of the sectioning element through the capsulorhexis, including the tight radius bend, are anterior to the lens 8, and the portion of the sectioning element 16 in the second, expanded configuration that contacts the capsular bag 6 is composed of more-flexible material even less likely to damage the capsular bag 6.

According to some embodiments, additional guide tubes or components may align or direct the path of the sectioning element 16 through the capsulorhexis 10 and/or around the lens 8. For example, in embodiments where the sectioning element 16 in the second, expanded configuration does not have a predefined shape, a guiding element may exist along areas of the distal portion 28 or proximal portion 26 of the sectioning element 16 to constrain it into a particular shape. A tube may extend from the merging point 22 in the direction of the distal portion 28, and the tube may concentrically constrain the flexible sectioning element 16 such that it more or less follows a desired path during insertion into the capsular bag 6 and placement around the lens 8. The guiding tube may then be retracted, leaving the flexible sectioning element 16 in place around the lens 8.

In still other embodiments, the predefined shape of the sectioning element 16 in the second, expanded configuration may be created during any part of the surgical procedure. For example, the surgeon may use imaging techniques to measure anatomical features of the eye such as the lens 8 or capsular bag 6. The surgeon may then use this information to or change a shape of the sectioning element 16. Alternatively, a piece of equipment such as a forming die or an automated wire forming machined may be used in conjunction with the measured data to change the shape of the sectioning element 16 in the second, expanded configuration. In one embodiment, the surgeon uses an imaging modality such as OCT to perform a measurement of the lens 8, and then this information is provided to an automated wire forming station that creates a custom sectioning element 16 for the patient. In still other embodiments, the surgeon may add or change a shape of the sectioning element 16 while at least a portion of the sectioning element 16 is within the eye. For example, the surgeon may begin to place the sectioning element 16 into the capsular bag 6 and determine that its shape may be improved. The surgeon may then insert a separate tool such as forceps into the eye or use an integrated tool associated with the shaft 12 to add or change a shape of the sectioning element 16.

According to some embodiments, a fluid is introduced between the capsular bag 6 after the capsulorhexis 10 is made, such that a space is created between the lens 8 and capsular bag 6 in at least some areas. This may be referred to as fluid dissection, hydro dissection or space creation. According to some embodiments, the fluid creates a space for the sectioning element 16 in the second, expanded configuration to be rotated within the capsular bag 6 and surround the lens 8. In an exemplary embodiment, fluids such as viscoelastic hyaluronic acid or saline may be injected since these materials are commonly used during ocular surgery, well-tolerated within the eye, and readily available. One or more other or additional fluids may be introduced, such as dyed fluids, pharmaceutical liquids like steroids, drug loaded fluids, bio absorbable fluids, lubricants, hydro gels, microspheres, powdered substances, fluorescent contrast, liquid foams, or any other suitable fluid. Additionally, one or more gases additionally or instead may be introduced, such as air, oxygen, argon, nitrogen, or the like. Alternatively, in other embodiments a fluid space may not be required between the lens 8 and the capsular bag 6, and the sectioning element 16 may perform a mechanical dissection or blunt dissection of the lens 8 and capsular bag 6 as it is rotated about the lens 8. Fluid dissection and blunt dissection may be done in combination with one another or separately. The fluid may be injected through a cannula or a needle into the capsular bag 6 using a separate instrument. According to other embodiments, provisions for fluid dissection may be incorporated into elements of the surgical device 40, such as the sectioning element 16. For example, the sectioning element 16 may be fabricated as a flexible tube with a plurality of holes along its length that allow for the passage of fluid therethrough. In such an embodiment, fluid may be introduced into the lumen of the sectioning element 16 and then flow out of the plurality of holes. This may improve the ability of the sectioning element 16 to pass between the capsular bag 6 and the lens 8 because the fluid may be introduced through the sectioning element 16 continuously or at discrete points in time when dissection is needed. In still other embodiments, the fluid injection may be incorporated in other aspects of the surgical device 40. For example, fluid may be delivered via the lumen 14 of the shaft 12. Alternatively, a component separate from the shaft 12, such as a telescoping tube or other tube, may be connected to the shaft 12 to provide for fluid introduction. In some embodiments, the fluid that is infused through a component of the device, such as the shaft 12 or the sectioning element 16, may be used for other surgical purposes. For example, fluid may be infused through the shaft 12 to maintain the chamber of the eye 1 without the need for a separate cannula or without the need for a viscoelastic substance. Irrigation and aspiration may be accomplished through a single component or through multiple separate components. For example, fluids such as saline may be irrigated into the eye through a lumen of an embodiment of the sectioning element 16, as described above, and aspirated through the lumen of the shaft 12. Other irrigation or aspiration techniques may be performed, according to some embodiments.

Figure 5:
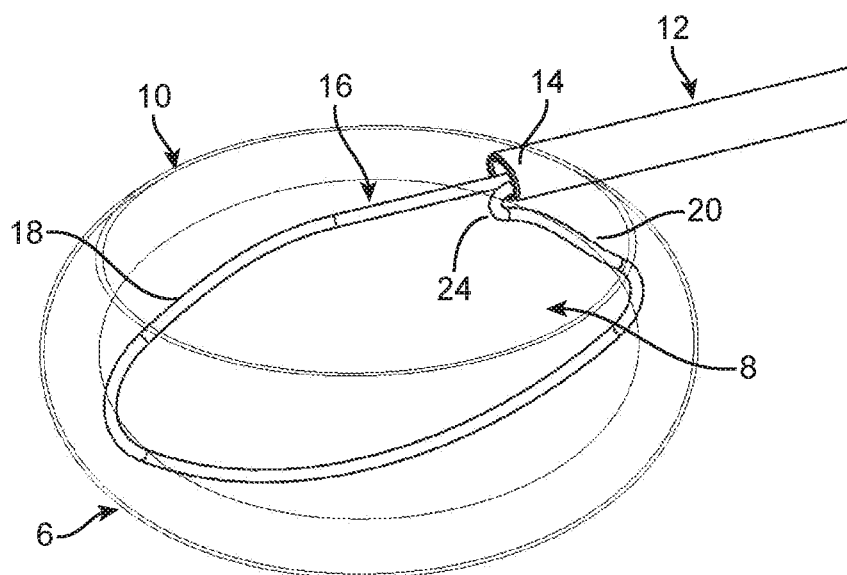
FIG. 5 is a perspective view of the capsular bag, with a completed capsulorhexis, with a sectioning element in a third, fragmentation position.
Figure 6:
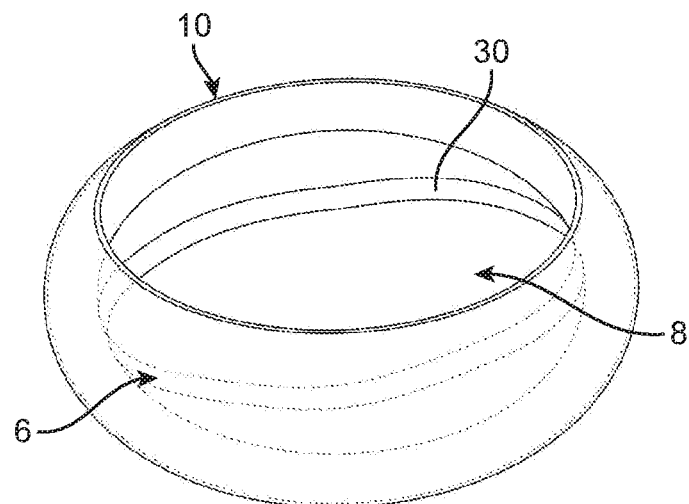
FIG. 6 is a perspective view of the lens of FIG. 5, with the sectioning element not shown for clarity.
Figure 7:
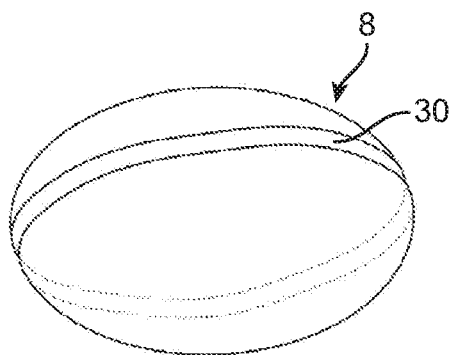
FIG. 7 is a perspective view of the lens of FIG. 5, with the sectioning element and capsular bag not shown for clarity.

Referring to FIG. 5, the sectioning element 16 has been fully extended to the second, expanded configuration, and has been rotated about the longitudinal axis of the shaft 12 and/or otherwise rotated or moved to an orientation within the capsular bag 6 in which the sectioning element 16 surrounds the lens 8 without exerting excessive force onto the capsular bag 6. The sectioning element 16 is then used to cut the lens 8 by tensioning one or both ends 18, 20 of the sectioning element 16, such as by retracting one or both ends 18, 20 through the lumen 14 of the shaft 12. The sectioning element 16 may be moved in the opposite manner as set forth above for expanding the sectioning element 16 from the first to the second configuration, in order to compress and cut the lens 8. As the sectioning element 16 is tensioned, it exerts an inward force on the lens 8 and begins cutting and/or fragmenting it due to the force applied to the lens 8 across the small surface area of the thin diameter sectioning element 16. The sectioning element 16 continues to be tensioned until the lens 8 is partially or fully sectioned. In some embodiments the sectioning element 16 is tensioned until the lens 8 is fully sectioned. In other embodiments, tensioning of the sectioning element 16 only partially fragments the lens 8, and the remainder of the lens 8 can be fragmented by repeating the use of the sectioning element, or with additional tools. Referring to FIG. 6, the fragmented lens 8 is shown within the capsular bag 6. The section plane is primarily vertical, but it should be appreciated that any number of angles and orientations may exist for the cutting path of the sectioning element 16. Referring to FIG. 7, the lens is shown with the capsular bag removed.

In some embodiments, the surgical device 40 may incorporate multiple sectioning elements 16, as described below, to create multiple lens fragments at one time. For example, the multiple sectioning elements 16 may form a mesh that is capable of cutting the lens 8 into a multitude of fragments; the sectioning elements 16 may be at oblique or acute angles relative to one another such that they form a crisscross pattern. In other embodiments, the surgical device 40 may be used successively on the lens 8. For example, after a single section is created the lens 8 (or the sectioning element 16) can be rotated 90 degrees such that the first section plane is now perpendicular to the delivery device plane. The sectioning element 16 can then be reinserted into the capsular bag 6 as described above, and used to create a new section across the two lens fragments that creates four fragments in total. The process may be repeated for as many times as necessary to create any number of lens fragments of any desired size. The final desired size of the lens fragments may depend on method of extraction from the eye 1. In some embodiments, phacoemulsification additionally may be used in the capsular bag 6 to remove the lens fragments. This may be particularly useful in difficult or hard cataracts, where full lens fragmentation increases the surface area and decreases the size of fragments that are to be emulsified by phacoemulsification. In other embodiments, the lens fragments may be extracted as described below.

In some embodiments, the lens fragments may be pushed out of the capsular bag 6 by introducing fluid into the capsular bag 6 under slight pressure. The fluid flow and/or pressure may move the lens fragments into the anterior chamber of the eye 1, such that other tools and methods for extracting the lens may be utilized. For example, forceps or grasping tools may be used to grab the lens fragments and pull them out of the eye 1 through the corneal incision 4. In some embodiments, the sectioning element 16 may be used to snare the lens fragments and pull them out of the eye 1. The sectioning element 16 may be returned to the second, expanded configuration and placed around a lens fragment. The sectioning element 16 may then be tensioned or otherwise closed until the lens 8 is held within of the sectioning element but the lens fragment is not cut. The lens fragment can then be pulled out of the eye 1 with the sectioning element 16. To ensure that the lens 8 is not cut by the sectioning element 16, additional components may be used such as pads, straps, or strips with a larger surface area that grip the lens fragment rather than cutting it. These components can be extended from the shaft 12, or may be separate components that are inserted into the eye 1 through the incision 4 and attached to the sectioning element 16.

Figure 8:
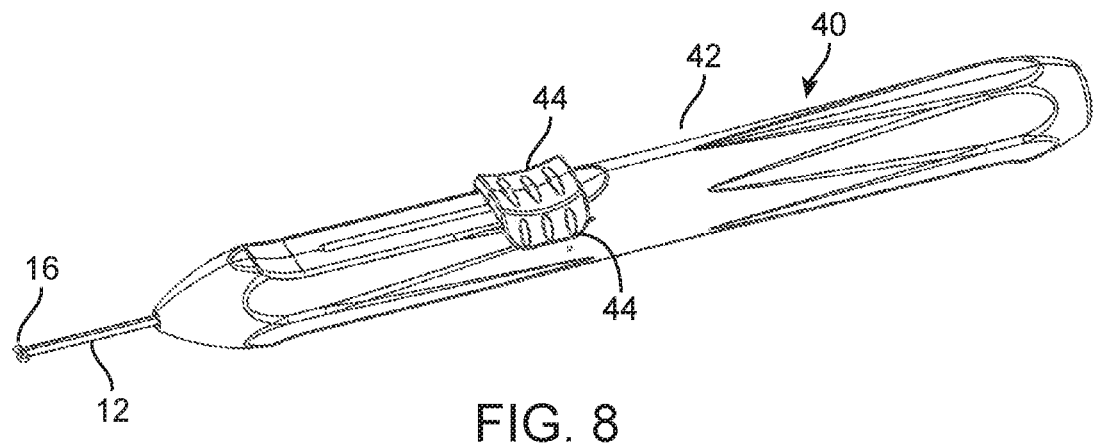
FIG. 8 is perspective view of a surgical device including a handle, shaft and multiple sectioning elements.
Figure 9:
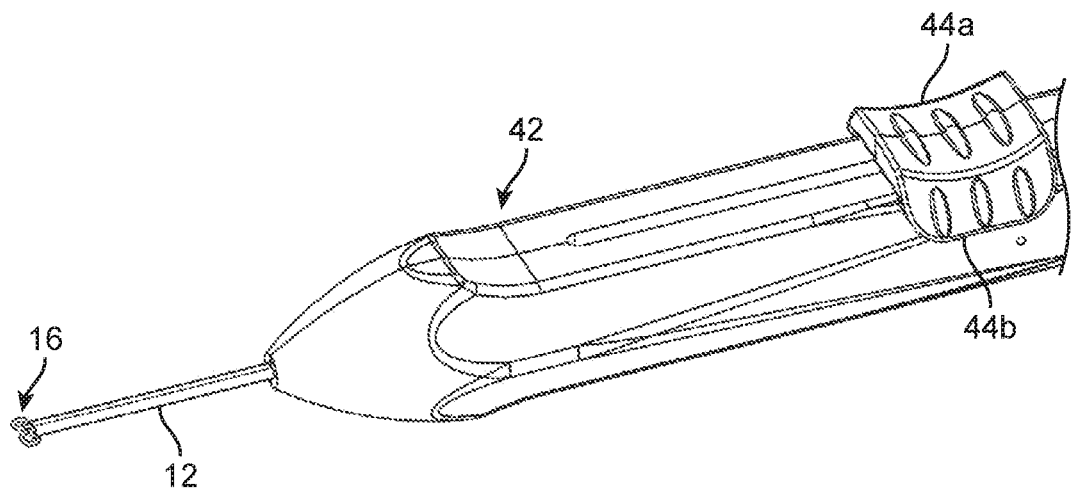
FIG. 9 is a perspective view of the surgical device of FIG. 8, with the sectioning elements in the first, retracted configuration.
Figure 15:
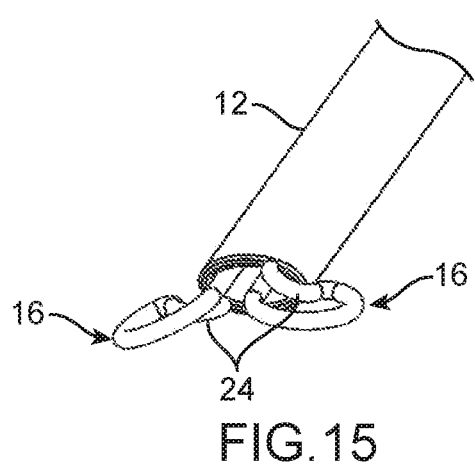
FIG. 15 is a detail perspective view of the distal end of the surgical device of FIG. 8.

Referring to FIGS. 8-9, one embodiment of the surgical device 40 includes two sectioning elements 16 extending from the distal end of a shaft 12, with a handle mechanism 42 attached to the proximal end of the shaft 12. Referring also to FIG. 15, two sectioning elements 16 are shown in the first, retracted configuration at the distal end of the shaft 12. The handle 42 has two sliders 44a, 44b slideable longitudinally, which are connected to the two sectioning elements 16 as described below. The sliders 44a, 44b in this initial configuration are in their retracted proximal location. The shaft 12 and sectioning elements 16 in the first, retracted configuration are inserted through an incision 4 in the cornea 2 toward a capsulorhexis 10, as described above. As used in this document, the term "handle" includes both handles configured for manual gripping and actuation by a surgeon, as well as a robotic handle that is coupled to a surgical robot and configured for robotic control and actuation.

Figure 16:
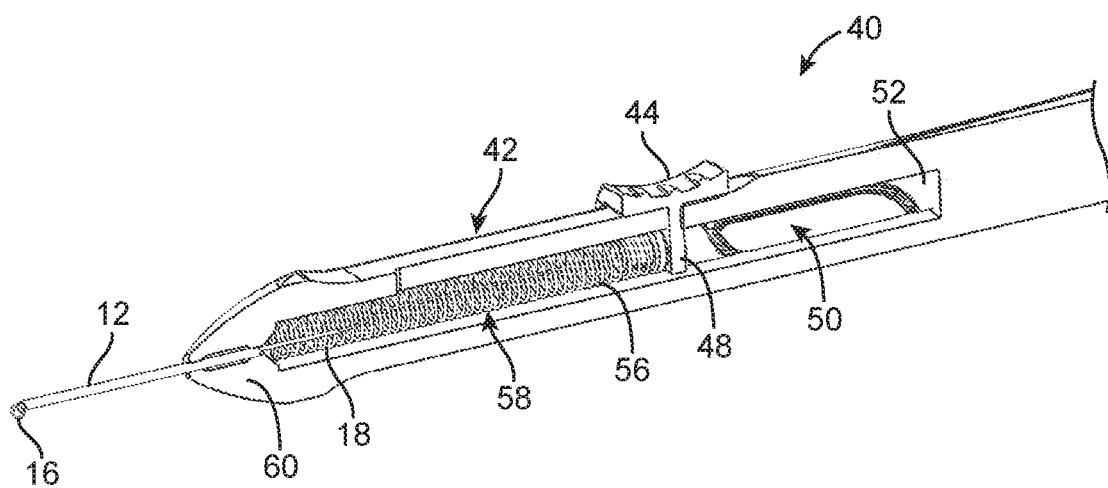
FIG. 16 is a cutaway perspective view of the handle, with the right slider in its initial position.
Figure 17:
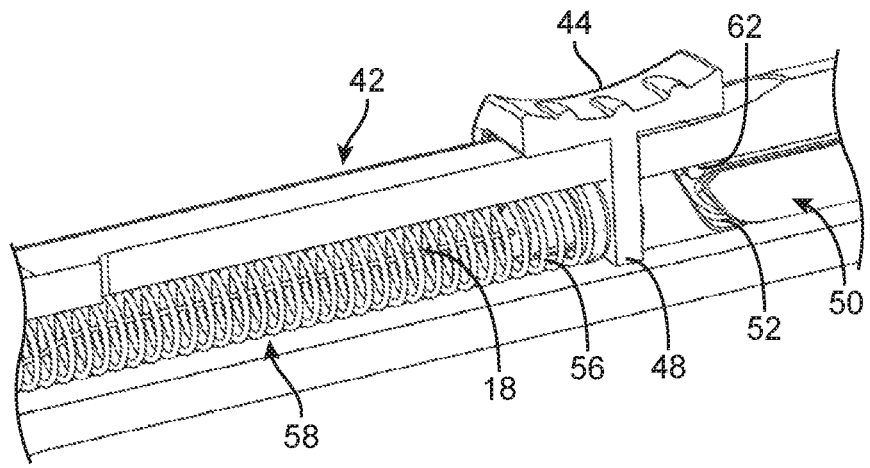
FIG. 17 is a detail perspective view of part of the handle of FIG. 16.

Referring also to FIGS. 16-17, one embodiment of a handle 42 of the surgical device 40 is shown in cutaway in a configuration corresponding to the first, retracted configuration of the sectioning elements 16. A slider 44 is slideable along the top surface of the handle 42. A finger 48 extends from the slider 44 into the handle 42 through a slot in the top surface of the handle 42. The finger 48 is coupled to a helical cam 50 or other cam structure, located proximal to the finger 48, that is longitudinally fixed to the finger 48 but that is free to rotate axially relative to the finger 48. This may be accomplished mechanically through an engagement pin, collar, or other suitable mechanism. A cam path 52 is defined in the surface of the helical cam 50. The helical cam 50 is confined within a chamber inside the handle 42 that allows the helical cam 50 to slide longitudinally but not move substantially radially. A nose 56 extends distally from the finger 48 and is rotatable relative to the finger 48. Advantageously the nose 56 is rotationally fixed to the helical cam 50. In some embodiments, the nose 56 is simply the distal end of the helical cam 50. A retraction spring 58 is positioned between the finger 48 and the front passage 60 out of the handle 42, acting to push the finger 48 toward the first, retracted configuration. The proximal end of the retraction spring 58 may be centered on and engage the nose 56. The proximal end of the first end 18 of the sectioning element 16 may be fixed to the nose 56 in any suitable manner, such as by wrapping around the nose, friction fitting, welding, soldering, or by pressure fitting. Alternately, the proximal end of the first end 18 may be fixed to the finger 48. A cam post 62 is defined in and/or fixed relative to the handle 42, and engages the cam path 52. As the helical cam 50 translates relative to a remainder of the handle 42, the cam post 62 remains in the same place on the handle 42. Where two sectioning elements 16 are used, two such assemblies as described above (the slider 44, finger 48, cam 50, nose 56, retraction spring 58 and connection to the first end 18 of the sectioning element 16) are utilized side-by-side within the handle 42. Such assemblies may be identical to one another, may be lateral mirror-images of one another, or may vary from one another in other ways that allow substantially the same assembly to operate two separate sectioning elements 16 in the manner described below. The description of the motion of the sliders 44a, 44b and the sectioning elements 16 are the same for both sliders 44 and sectioning elements 16 unless otherwise noted, and the descriptions of the two are interchangeable unless otherwise noted.

Figure 10:
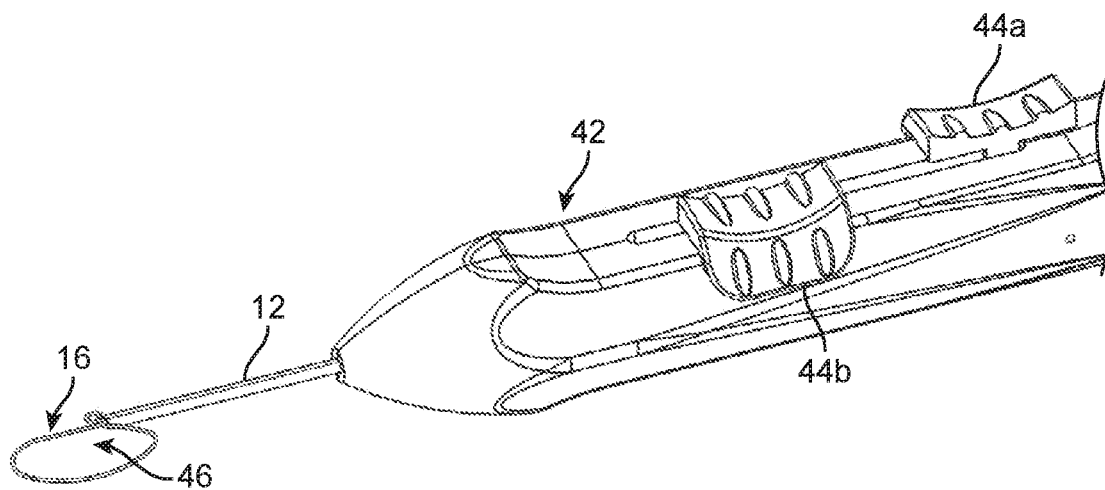
FIG. 10 is a perspective view of the surgical device of FIG. 8, with a left slider advanced to expand a left sectioning element toward the second, expanded configuration.
Figure 18:
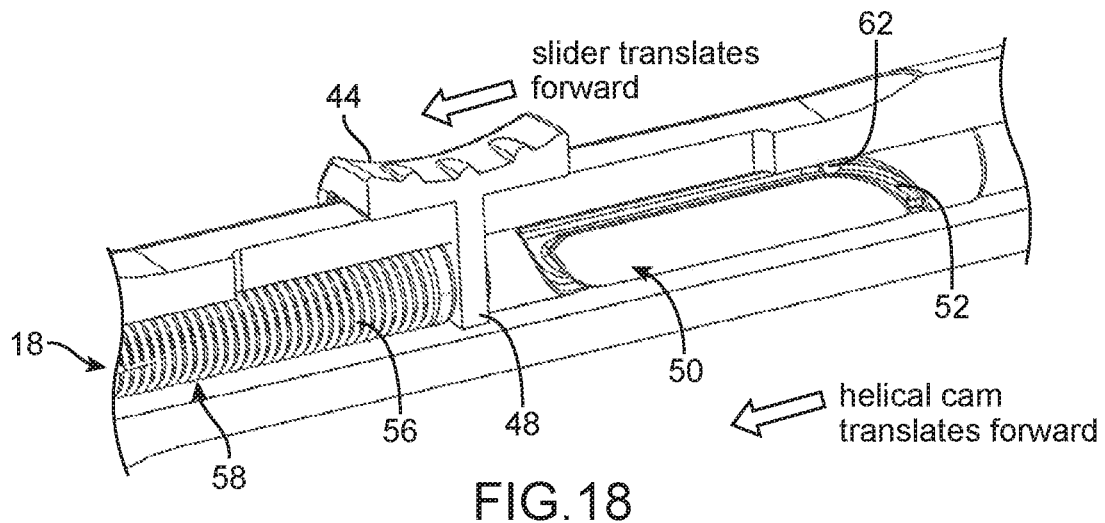
FIG. 18 is a detail perspective view of a different part of the handle of FIG. 16.

Referring to FIG. 10, one of the sectioning elements 16 is transitioned to the second, expanded configuration by sliding the corresponding slider 44b distally. One end 20 of the sectioning element 16 may be connected to the shaft 12, handle 42, or other structure fixed relative to the handle 42, and maintained in a fixed position while the first end 18 is configured to translate and rotate with the moving elements within the handle 42. As set forth above, the first end 18 is attached to the nose 56. Referring also to FIG. 18, as the slider 44 translates distally, the finger 48 compresses the retraction spring 58, moves the nose 56 distally, and pulls the helical cam 50 distally. The retraction spring 58 is compressed and imparts a proximal force on the finger 48. If the user releases the slider 44, the slider 44, finger 48, and mechanisms translationally fixed to the finger 48 are pushed distally toward the initial position of the slider 44. As the slider 44 advances distally, the helical cam 50 translates within the handle 42. The cam path 52 may be substantially longitudinal during this first segment of motion of the slider 44, such that engagement between the cam path 52 and cam post 62 does not cause rotation of the helical cam 50. Therefore, the sectioning element 16 remains in substantially the same rotational orientation relative to the longitudinal axis of the shaft 12. As the slider 44 advances distally, it pushes the first end 18 of the sectioning element 16 distally. As a result, the sectioning element 16 changes shape to the second, expanded configuration, in the same manner as described above with regard to FIGS. 1-4.

Figure 11:
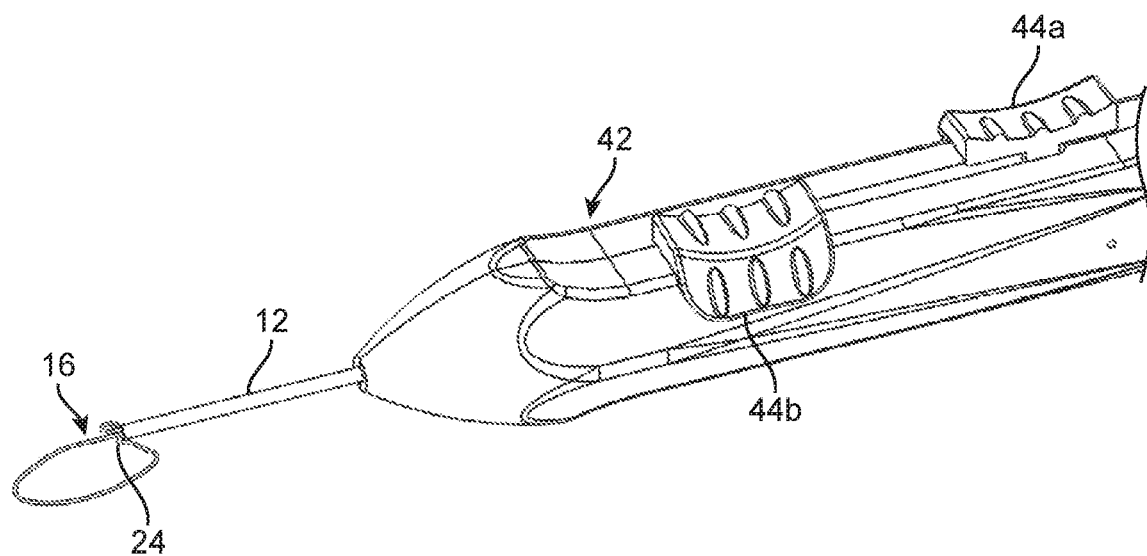
FIG. 11 is a perspective view of the surgical device of FIG. 8, with a left slider fully advanced to expand the left sectioning element to the second, expanded configuration.
Figure 19:
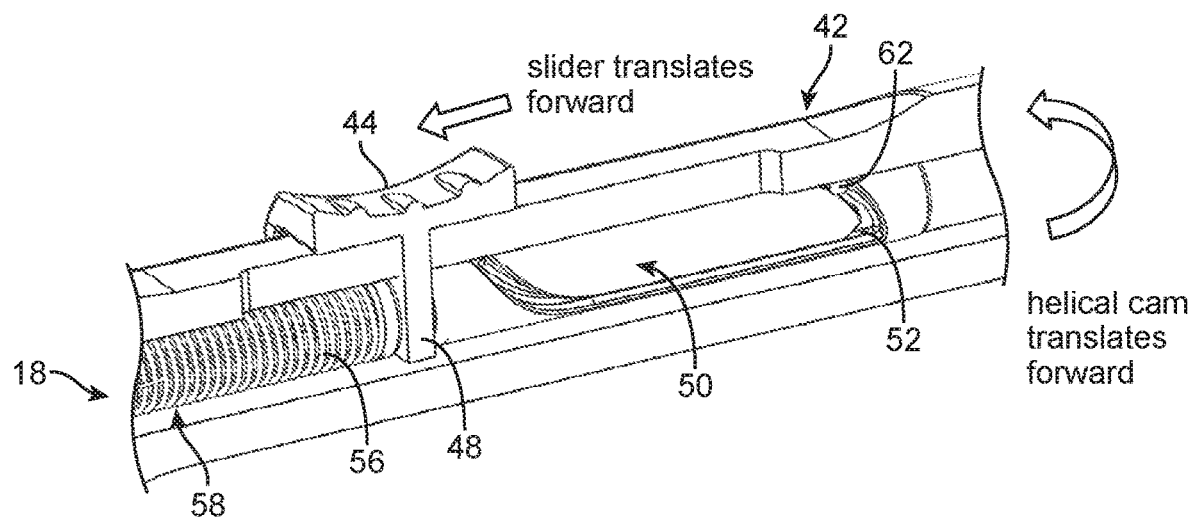
FIG. 19 is a detail perspective view of the handle of FIGS. 16-18, with the right slider partially advanced.
Figure 20:
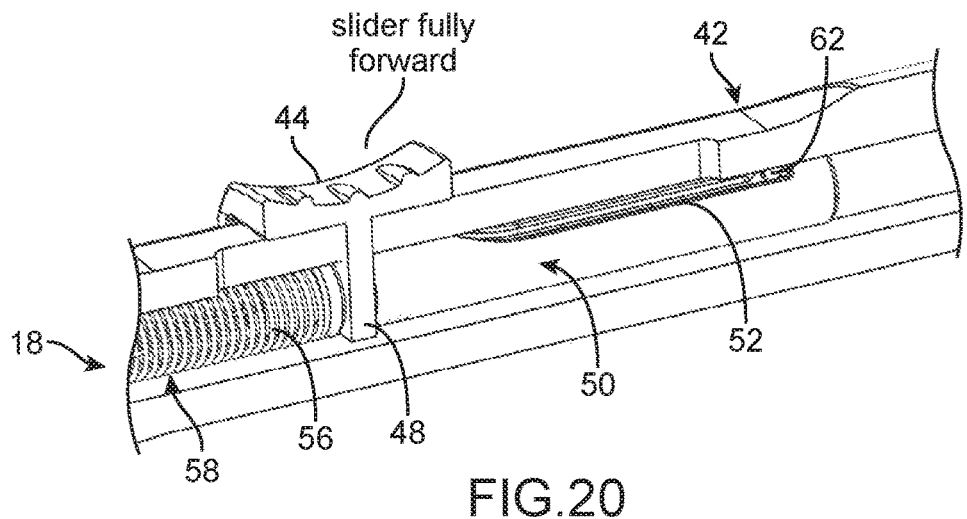
FIG. 20 is a detail perspective view of the handle of FIGS. 16-18, with the right slider advanced further distally than its position in FIG. 19.

Referring also to FIG. 11, the slider 44 may be further advanced distally after the sectioning element 16 changes shape to the second, expanded configuration. The cam path 52 engages the cam post 62 to rotate the helical cam 50, as seen in FIGS. 18-20. The amount of distal motion of the slider 44 controls the amount of rotation of the helical cam 50. In this way, linear motion of the slider 44 is converted to rotary motion of the sectioning element 16. Because the helical cam 50 and the nose 56 are rotationally fixed to one another, rotation of the helical cam 50 causes rotation of the nose 56, and thus rotation of the sectioning element 16 in the second, expanded configuration. The sectioning element 16 rotates, and the plane defined by the shape of the sectioning element 16 correspondingly rotates. The sectioning element 16 is rotated from its initial position, which may be substantially parallel to a plane defined by the edges of the capsulorhexis 10, to a position that is approximately within 0-40 degrees from a vertical orientation. During this rotation, the sectioning element 16 moves between the capsular bag 6 and the lens 8, capturing the lens 8 in the open area 46 within the perimeter of the sectioning element 16. The sectioning element 16 may not engage the capsular bag 6 and/or lens 8 substantially, or may be configured to engage either the lens 8 or the capsular bag 6. Alternately, the sectioning element 16 may cause a blunt dissection between the capsular bag 6 and the lens 8.

Referring also to FIG. 20, the slider 44 is moved fully forward and the rotation of the helical cam 50 and sectioning element 16 is complete. The sectioning element 16 surrounds the lens 8 within the capsular bag 6, and is configured to apply an inward cutting force relative to the lens 8, in the manner described above with regard to FIGS. 4-5.

Figure 12:
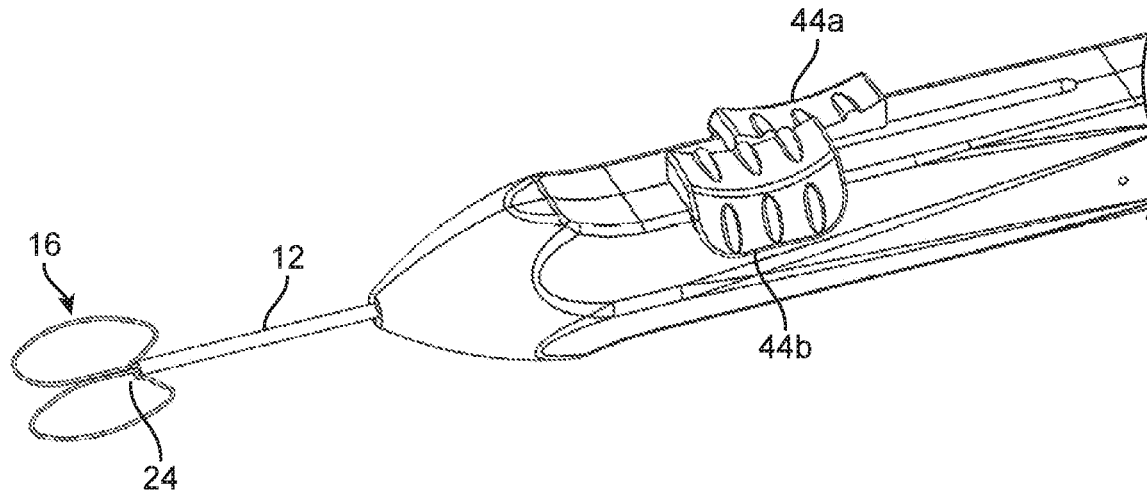
FIG. 12 is a perspective view of the surgical device of FIG. 8, with a right slider advanced to expand a right sectioning element toward the second, expanded configuration.
Figure 13:
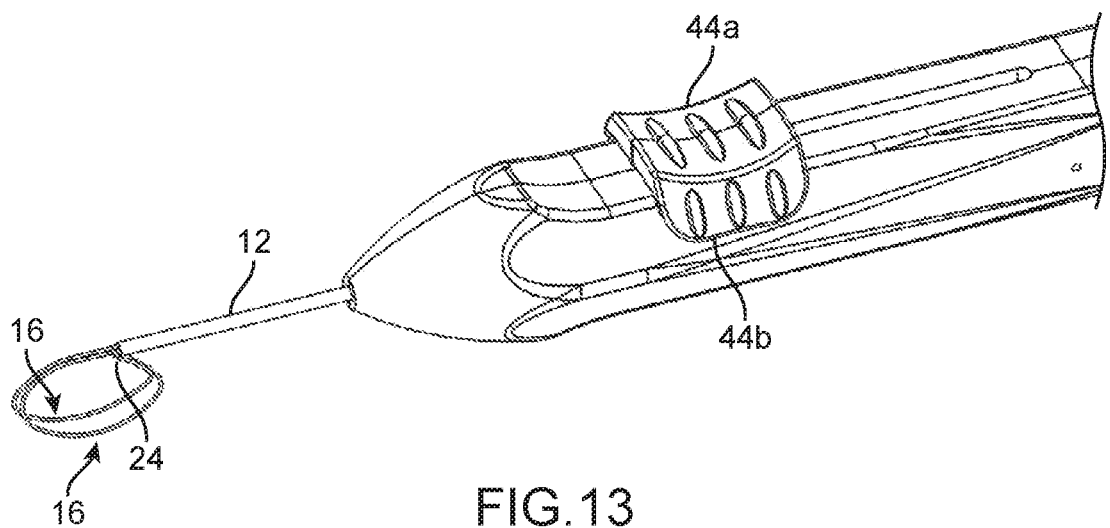
FIG. 13 is a perspective view of the surgical device of FIG. 8, with a right slider fully advanced to expand the right sectioning element to the second, expanded configuration.
Figure 14:
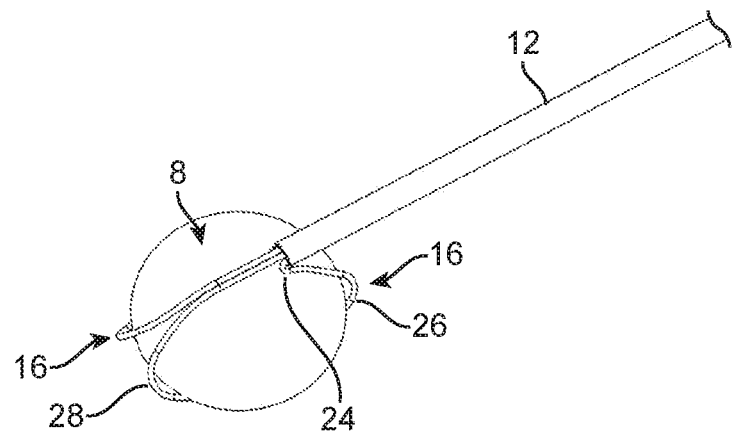
FIG. 14 is a perspective view of FIG. 13, showing the sectioning elements relative to the lens.
Figure 21:
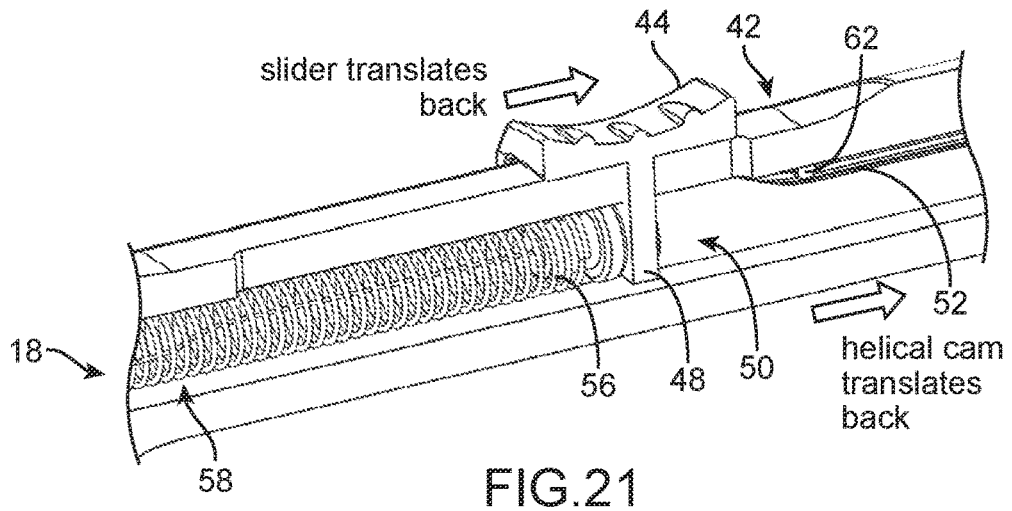
FIG. 21 is a detail perspective view of the handle of FIGS. 16-18, with the right slider returned toward its original position.

Referring also to FIGS. 12-13, a second sectioning element 16 then may be deployed to a second, expanded configuration, and rotated into position to surround the lens 8, in the same manner as described above with regard to FIGS. 9-11 and 16-20. Referring also to FIG. 14, both sectioning elements 16 engage the lens 8, such that when the sectioning elements 16 are tensioned or otherwise closed, the sectioning elements 16 will cut the lens 8 into three partially- or fully-separate fragments. Referring also to FIG. 21, the tensioning may be provided by sliding the sliders 44 proximally, thereby pulling the first end 18 of each sectioning element 16 proximally and tensioning it. In some embodiments, the proximal force exerted on the finger 48 by the retraction spring 58 may be sufficiently large to cut the lens 8 without the application of additional force by the user. In other embodiments, the user provides additional force that fragments the lens 8. This may be necessary especially for hard or difficult cataracts. Each sectioning element 16 engages the posterior surface of the lens 8 along a line spaced apart from the other sectioning element 16, and engages the anterior surface of the lens 8 along substantially the same line, according to some embodiments.

Figure 22:
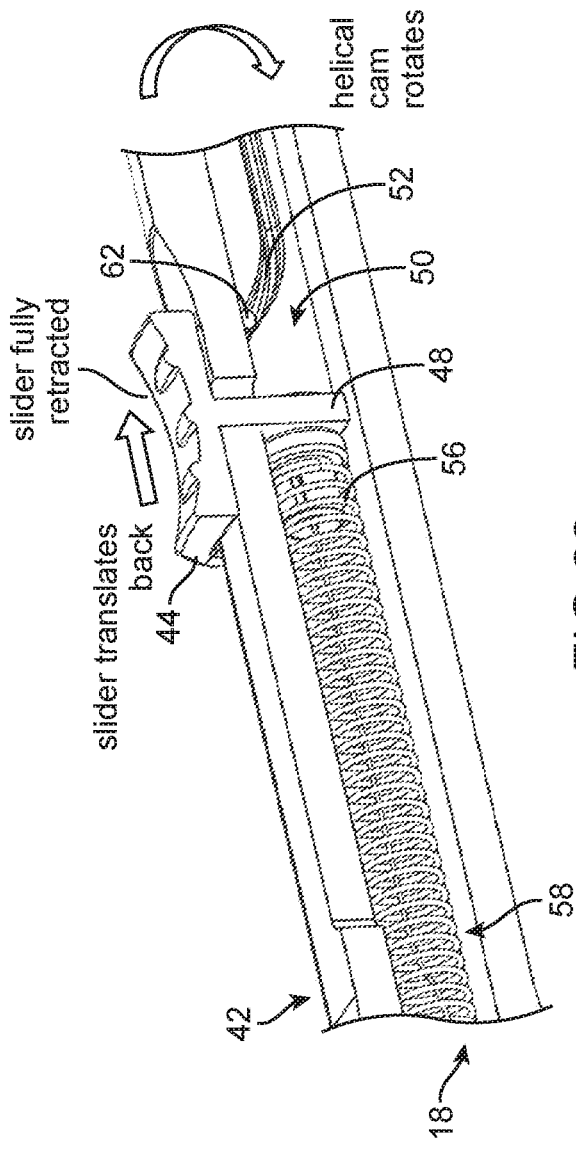
FIG. 22 is a detail perspective view of the handle of FIGS. 16-18, with the right slider returned to its original position.

In FIG. 22, the slider 44 is moved proximally to return to the original position. The sectioning element 16 is rotated back to its original plane of insertion, and then retracted toward the shaft 12. Referring also to FIG. 15, the sectioning elements 16 may return substantially to their initial configuration after sectioning the lens. The cam path 52 of the helical cam 50 may be a closed loop as shown. Alternately, the cam path 52 may be a one-way path wherein the slider 44 must be translated fully distally and then proximally to move it to the original position. In some embodiments, one-way latches or levers may be incorporated into the cam path 52 that prevent the helical cam 50 from rotating or moving in certain directions, and may be included at discrete positions of the cam path 52 or along the entire cam path 52.

According to some embodiments, the sectioning elements 16 may be configured to move synchronously with the actuation of a single slider 44, rather than each sectioning element 16 being coupled to a different slider 44a, 44b as described above. If so, the sectioning elements 16 may be configured to expand, open and/or rotate at the same time. Alternately, the rotation of the sectioning elements 16 may be staggered such that one sectioning element 16 opens first and rotates first before the other sectioning element 16. This may be accomplished by associating a different cam path 52 and cam post 62 with each sectioning element 16. In still other embodiments, two sliders 44a, 44b can be configured such that a left slider 44b will move both sliders 44 forward, but the right slider 44a will only move the right slider 44a forward (or vice versa). The right slider 44a may be configured to move both sliders 44a, 44b backward and the left slider to move only the left slider 44b backward. Thus, the user may decide whether to move the sliders 44a, 44b independently or synchronously.

According to some elements, the sectioning elements 16 are rotated in the same direction. For example, the first sectioning element 16 opens and is then rotated into the capsular bag 6 in a clockwise direction. The second sectioning element then opens and is also rotated into the capsular bag 6 in a clockwise direction. In this embodiment, the first sectioning element 16 may rotate to an angle 10-40 degree beyond a vertical plane, and the second sectioning element 16 may rotate to an angle 10-40 degree less than a vertical plane.

In still other embodiments, one or more additional or different mechanisms may be used to deploy the sectioning elements 16. For example, a scroll wheel advancing mechanism or other rotating mechanism could be used to deploy one or both sectioning elements 16. In some embodiments, the movement by the user is geared up or down to the movement of the sectioning element 16 such that moving a given amount of the user interface components moves the sectioning element 16 a greater or lesser amount through the use of gears, scaled pulleys or any other number of components. In some embodiments, certain parts of the surgical device 40 may be mechanically powered through components such as motors, linear motors, pneumatics, hydraulics, magnets, or the like. The surgical device 40 may be incorporated as a part of one or more larger robotic assemblies. For example, a robotic device that is configured to perform a cataract procedure may include an embodiment of the surgical device 40. This may allow surgeons to perform parts of the described method robotically. In some embodiments this may allow for alternate techniques and methods such as approaching the capsular bag 4 through the sclera. According to some embodiments, at least inserting a shaft 12 having a lumen 14 therethrough, through the corneal incision 4 toward the capsulorhexis 10, and extending a sectioning element 16 out of the distal end of the lumen 14, to cause the sectioning element 16 to bend away from the axis of the shaft 12 through the capsulorhexis 10, expand to a size greater than the capsulorhexis 10, and capture at least a part of the lens 8, are performed under robotic control.

In some embodiments, the sectioning element 16 need not approximate a loop initially as it is placed into the capsular bag 6. For example, the sectioning element 16 may be a single piece of round wire that is fed into the capsular bag 6 from the shaft 12, without doubling back on itself to form a loop. In such an embodiment, the distal tip of the sectioning element 16 is blunt to prevent puncture or damage to tissue within the eye 1. As the distal tip of the sectioning element 16 reaches the wall of the capsular bag 6, it may be configured to bend with either a predefined bend in its structure, or by tracking along the inner surface of the capsular bag 6. The sectioning element 16 may then traverse a space between the lens 8 and the capsular bag 6 such that it goes around a circumference of the lens 8. The sectioning element 16 may then come back into the view of the user into the top portion of the capsular bag 6 where the user can grab the sectioning element 16 with features on the handle 42 such as grippers, or with a separate tool entirely. At this point, the sectioning element 16 surrounds the lens 8 within the capsular bag 6 and approximates a loop. As one or both ends of the sectioning element 16 are tensioned and/or pulled, an inward cutting force is applied to the lens 8 such that it is fragmented. The sectioning element 16 of this embodiment may have a cross-section that allows it to bend preferentially in certain directions more easily than others, such that the sectioning element 16 can bend as necessary to track around the lens 8 but still follow a suitable path around the lens 8 without going off track into tissue. This may include the use of a preferred bending moment cross-section like an "I" beam that bends preferentially about certain planes. Alternatively, a tube with cutouts to allow bending may be configured to bend in certain planes by placing the cuts in this plane. Therefore, the sectioning element 16 may bend around the lens 8, primarily in a distal-to-proximal manner. This may improve the ability of the sectioning element 16 to traverse a desired general path relative to capsular bag 6 and lens 8. In some embodiments, the sectioning element 16 may be entirely flexible such that its distal tip is unconstrained to travel in any predefined path. The distal tip may be configured to include a magnet or electromagnetic components to which a force can be applied to with an external electromagnetic field. An external device may then be used to control the location of the distal tip of the sectioning element 16 such that it may be guided around the capsular bag 6 along a desired path. Any number of different paths or fragmentation planes may be contemplated with this embodiment. The surgical device 40 may incorporate various imaging modalities in order to create a desired path for the distal tip of the sectioning element 16 that does not damage the capsular bag 6.

In some embodiments, the sectioning element 16 may bifurcate into multiple portions and/or multiple loops. For example, in the initial configuration, the sectioning element 16 may have a shape and profile as described above. However, when transitioned to the second, expanded configuration, the sectioning element 16 may bifurcate along its length into two elements that may have the same or similar shapes, or different shapes, each surrounding the lens 8 in whole or in part. This may allow the sectioning element 16 to cut the lens 8 into multiple fragments without using two separate sectioning elements 16.

In some embodiments, one or both of the sectioning elements 16 may be configured to apply one or more types of energy to aid in the blunt dissection or fragmentation of the lens 8. For example, one or both of the sectioning elements 16 may include one or more portions configured to be heated through the use of electrically resistive wire that becomes hot as current is run through it. The increased temperature may improve the separation of the capsular bag 6 and the lens 8 as well as aid in sectioning the lens 8. Alternatively, any number of other modalities may be used such as radio frequency ablation, electric cautery, ultrasonic vibratory energy, or the like.

Ultraviolet (UV) energy can kill cells that can contribute to secondary opacification of the capsule after primary cataract surgery. Treating the capsule with UV energy while the lens is being separated and sectioned from the lens capsule can reduce the rate of incident secondary opacification. UV energy can be applied via one or more sectioning elements 16 of the device. In some implementations, the sectioning element 16 can be a non-metal filament that can be used to transmit UV light through the sectioning element 16. For example, the sectioning element 16 can be formed of a transparent, flexible polymer or other material that can transmit the UV light therethrough. Thus, the sectioning element 16 can act as a sort of light pipe to transmit the UV energy during capture and sectioning of the lens 8. In other implementations, the sectioning elements 16 can be formed of metal such as Nitinol wire and be sheathed in a transparent polymer material that can be used as a light pipe to allow the UV energy to be transmitted through the sheathe to treat the capsule.

In some embodiments, the handle 42 may incorporate fluid delivery features. For example, as described above, the sectioning element 16 or the shaft 12 may allow the injection of fluids through the respective components. The handle 42 may include fluid passageways and paths that connect these components to external fluid sources through tubes, integrated connectors, or the like. Alternatively, the handle 42 may include internal pressure injection systems that push fluid through the shaft 12. The fluid may be stored in a cylinder with a piston wherein the piston is pressed forward by actuation components in the handle 42. For example, a separate slider or button may be connected to the piston and arranged such that as the slider is moved by the user, the piston is translated and expels a fluid from the cylinder into the injection system. This may allow the user to control the delivery of fluid through the sectioning element 16, the shaft 12, or any other handle 42 component at certain times during the procedure such as creating space between the capsular bag 6 and the lens 8. Alternatively, the surgical device 40 may be configured such that the fluid is injected automatically by the surgical device 40 during certain periods within the normal actuation of the device. For example, a spring may be configured to place a force on the piston such that as the helical cam 50 moves through its path, the piston is configured to expel an amount of fluid.

Figure 23:
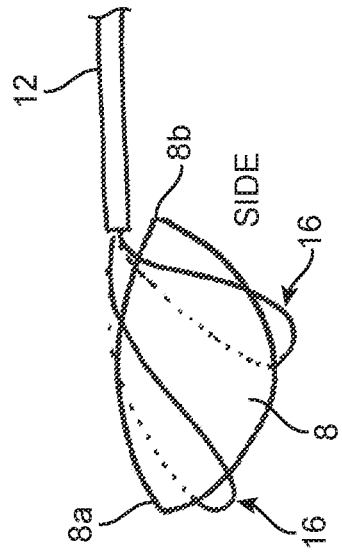
FIG. 23 is a side view of another embodiment of two sectioning elements extending from a shaft to encircle a lens.

Referring to FIG. 23, an alternate embodiment of sectioning elements 16 is shown as a side view. Two sectioning elements 16 extend from the distal end of the shaft 12. In this embodiment, the sectioning elements 16 are arranged to loop around the lens 8 starting at the distal end 8a of the lens 8, rather than around the sides of the lens 8 as described above. The sectioning elements 16 may be extended one at a time from the distal end of the shaft 12 distally toward the distal end 8a of the lens 8 and into the capsular bag. The sectioning element 16 may approximate a loop of wire that is configured to have a predefined shape and curves to allow it go around the lens 8 without placing excessive force on the capsular bag. This may include side-to-side bends as wells as forward-and-back curves that form various three-dimensional geometries as the sectioning element 16 is extended from the delivery device. In order to enter the capsular bag and capture the lens 8, the sectioning elements 16 are configured to be shaped differently as they expand. Rather than being planar, these sectioning elements 16 are curved downward from the shaft 12 in the second configuration, as seen in FIG. 23. Where multiple sectioning elements 16 are used, each may be configured to curve to a different degree than the other or others. One end of the sectioning element 16 may be extended while the other remains relatively fixed to the delivery device, or both ends may be extended at the same time, as described above. As described above, the sectioning element may have various profiles, materials, or flexibilities along its length.

One of the sectioning elements 16 may be extended to traverse the space between the capsular bag and the lens 8, and then may be moved downward and proximally around the lens 8. A second sectioning element 16 may be extended as shown, and any number of other sectioning elements 16 may be used. In some embodiments, a forward extending sectioning element 16 may be used in conjunction with a side extending sectioning element 16 as described above, in order to create intersecting fragmentation planes such that two sectioning elements 16 can slice the lens into 4 discrete pieces. Furthermore, the fragmentation planes can be at any number of angles to each other, and the sectioning elements 16 can extend around the lens 8 from any number of directions such as a combination of the forward extending and side extending embodiments.

FIGS. 24A-24E, FIGS. 25A-25C, FIGS. 26A-26N, FIGS. 27A-27C, FIGS. 28A-28B, FIGS. 29A-29B, FIGS. 30A-30E, FIGS. 31A-31F illustrate interrelated implementations of a device 2440 for fragmentation of a lens 8 within the capsular bag 6 and for removal of the lenticular tissue from the eye 1. The same or similar reference numbers may refer to the same or similar structures. Aspects described with respect to the same or similar structures may be equally applicable to the structures described elsewhere herein. Features, aspects, and methods of using each of the devices and methods described herein may be equally applicable to the implementations of devices and methods described below.

As with other implementations described elsewhere herein and as shown in FIGS. 24A-24E, the device 2440 can include a housing 2442 having a nose cone 2443. A distal shaft 2412 can extend from the housing 2442 along a longitudinal axis of the device, the shaft 2412 having a lumen and a distal end. The device can include a cutting element 2416 movable through the lumen of the shaft 2412. The cutting element and the shaft 2412 are configured to be inserted through an incision 4 in the cornea 2. For example, the distal shaft 2412 can have an outer diameter sized to extend through a self-sealing incision in a cornea 2. The shaft 2412 can have an outer diameter configured to insert within the anterior chamber that is between about 0.5 mm and about 2.5 mm. In some implementations, the shaft 2412 may have a uniform outer diameter along its length from the nose cone 2443 to the distal tip of the shaft 2412. The outer diameter of the shaft 2412 may also have a non-uniform outer diameter along its length. For example, in some implementations, the shaft 2412 may taper towards the distal outlet 2405 such that the outer diameter near the distal tip is smaller than an outer diameter near the nose cone 2443. In still further implementations, the shaft 2412 may have a beveled edge near the distal outlet 2405. A bellows 2445 (see FIG. 24E) can be coupled to a forward-facing, distal end of the housing 2442. The bellows 2445 can be cylindrical in shape and surround a proximal end of the distal shaft 2412 extending through nose cone 2443. The bellows 2445 can be a relatively soft element. A distal end of the bellows 2445 is configured to engage and seal with an outer surface of the eye surrounding the incision 4 upon insertion of the shaft 2412 through the incision 4. The bellows 2445 can provide a visual indication of depth of penetration. The shaft 2412 has reached a proper depth of penetration once the distal end of the bellows 2445 contacts an outer surface of the eye. The bellows 2445 can thereby additionally prevent over-insertion of the shaft 2412 in the eye beyond a certain desirable depth. In some implementations, a plurality of grooves 2447 can be formed in an outer surface of the bellows 2445 giving it a ringed appearance. The grooves 2447 allow for the bellows 2445 to compress along a longitudinal axis upon application of a force and to expand along the longitudinal axis to be longer upon release of the force.

The cutting element of the device 2440 includes one or more sectioning elements 2416 moveably extendable through a lumen of the distal shaft 2412. Each sectioning element 2416 can include a first end, a second end, and a distal loop formed between the first and second ends, as will be described in more detail below. At least a portion of each of the sectioning elements 2416 can be housed within corresponding one or more secondary tubular elements or sheaths or sleeves 2415 (see FIG. 24E or 26A) that are, in turn, housed within the lumen of the distal shaft 2412. The cutting element is configured to transition from a first, retracted configuration towards a second, expanded configuration upon activation of an actuator on the device 2440. When in the second, expanded configuration, the distal loop of each of the sectioning elements defines an enlarged open area. The enlarged open areas may be located outside the distal end of the shaft 2412 and have a first leg advanced distally relative to the distal end of the shaft and a second leg positioned proximally to the distal end of the shaft. The distal loops defining the enlarged open areas of each of the sectioning elements 2416 can be aligned generally parallel to one another within a plane (such as a vertical plane) when the cutting element is in the second, expanded configuration. A second activation of the actuator or a second, different actuator may cause the distal loops defining the enlarged open areas of at least one or more of the sectioning elements to move angularly relative to the plane thereby transitioning the cutting element into a third, splayed configuration. The second activation of the actuator or a second, different actuator may cause the distal loops of the enlarged open areas of each sectioning element to move angularly away from one another, for example, two sectioning elements moving angularly away from each other, thereby transitioning the cutting element into the third, splayed configuration.

The sectioning elements 2416 are configured to be deployed within the eye such that loops or open areas are enlarged at a distal end of the sectioning elements 2416 that are sized to surround at least a portion of a lens 8 positioned within a capsular bag 6. The open areas defined by the distal loops of the sectioning elements 2416 are configured to expand from the first, retracted configuration for insertion (FIG. 24A) to the second, expanded configuration (FIG. 24B) and to the third, splayed configuration (FIG. 24C). When moved from the collapsed position (FIG. 24A) toward the unbiased shape of the expanded position (FIG. 24B), each of the one or more sectioning elements 2416 can form a distal loop having an unbiased (unconstrained) shape that bounds an open area 2446 defined in an orientation that maximizes the open area 2446. It should be appreciated that use of the term "loop" when referring to the cutting end of the unbiased, unconstrained shape of the sectioning elements 2416 does not limit the open area 2446 to having a particular shape, such as a circle. The shape of the loop can be oval, elliptical, or another irregular, non-geometrical shape. The loop also need not be fully closed.

The devices are described as useful for cutting a whole lens within the capsular bag, but may be used for other purposes without departing from various aspects of the device and methods described. The sectioning elements described herein may be positioned and extended between the capsular bag and the anterior side of the lens due to natural expansion of the loops toward the expanded shape. When cutting the lens, the loops may extend around the posterior and anterior surfaces to form a full cut of the lens. The loops may also be moved between the posterior surface of the lens and the capsular bag to dissect the lens from the capsular bag before cutting the lens into fragments. The devices described herein are particularly useful in advancing atraumatically between the bag and lens while the lens is still whole.

Figure 24A:
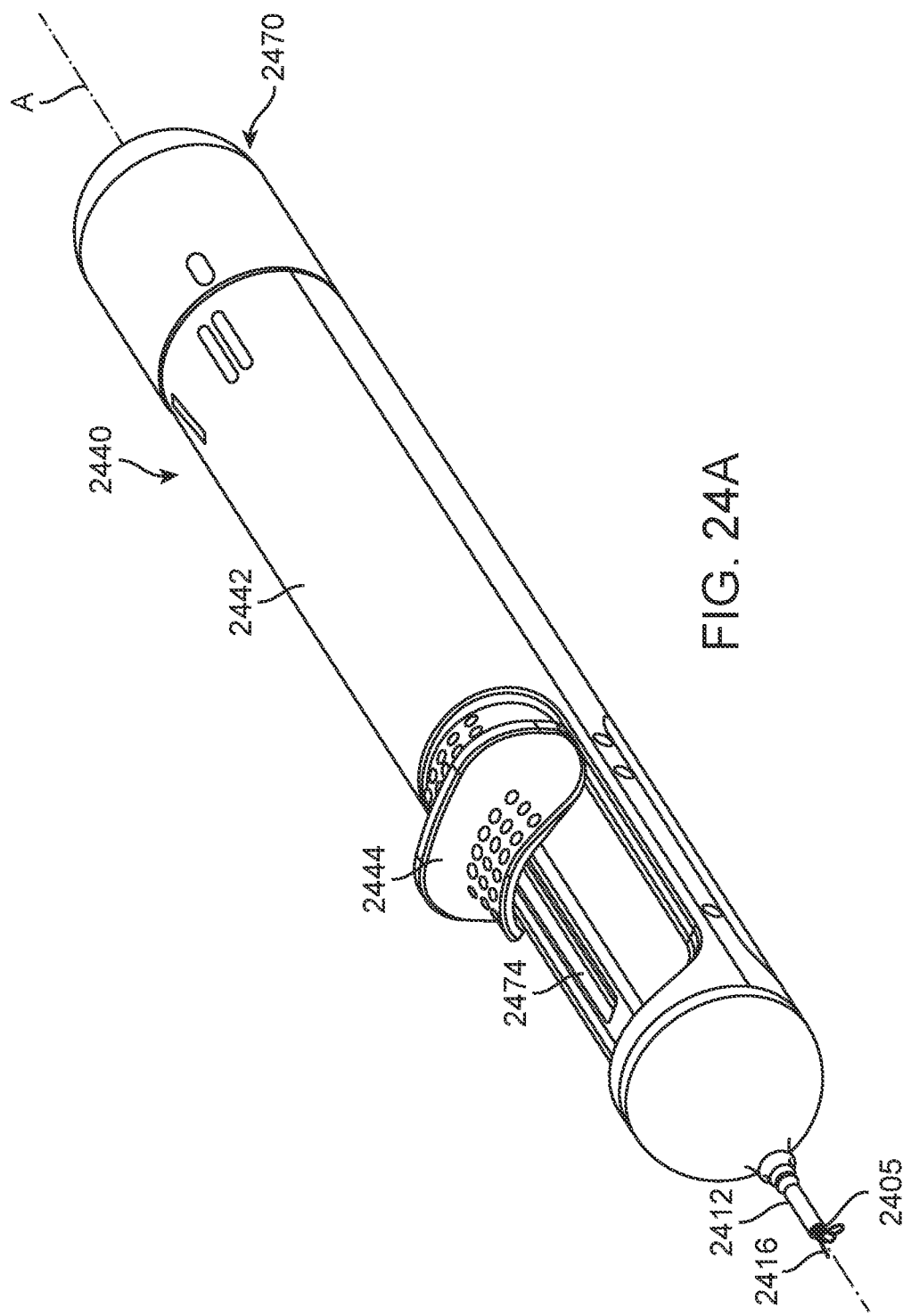
FIG. 24A is a perspective view of another implementation of a surgical device including a handle, shaft and multiple sectioning elements prior to deployment.
Figure 24C:
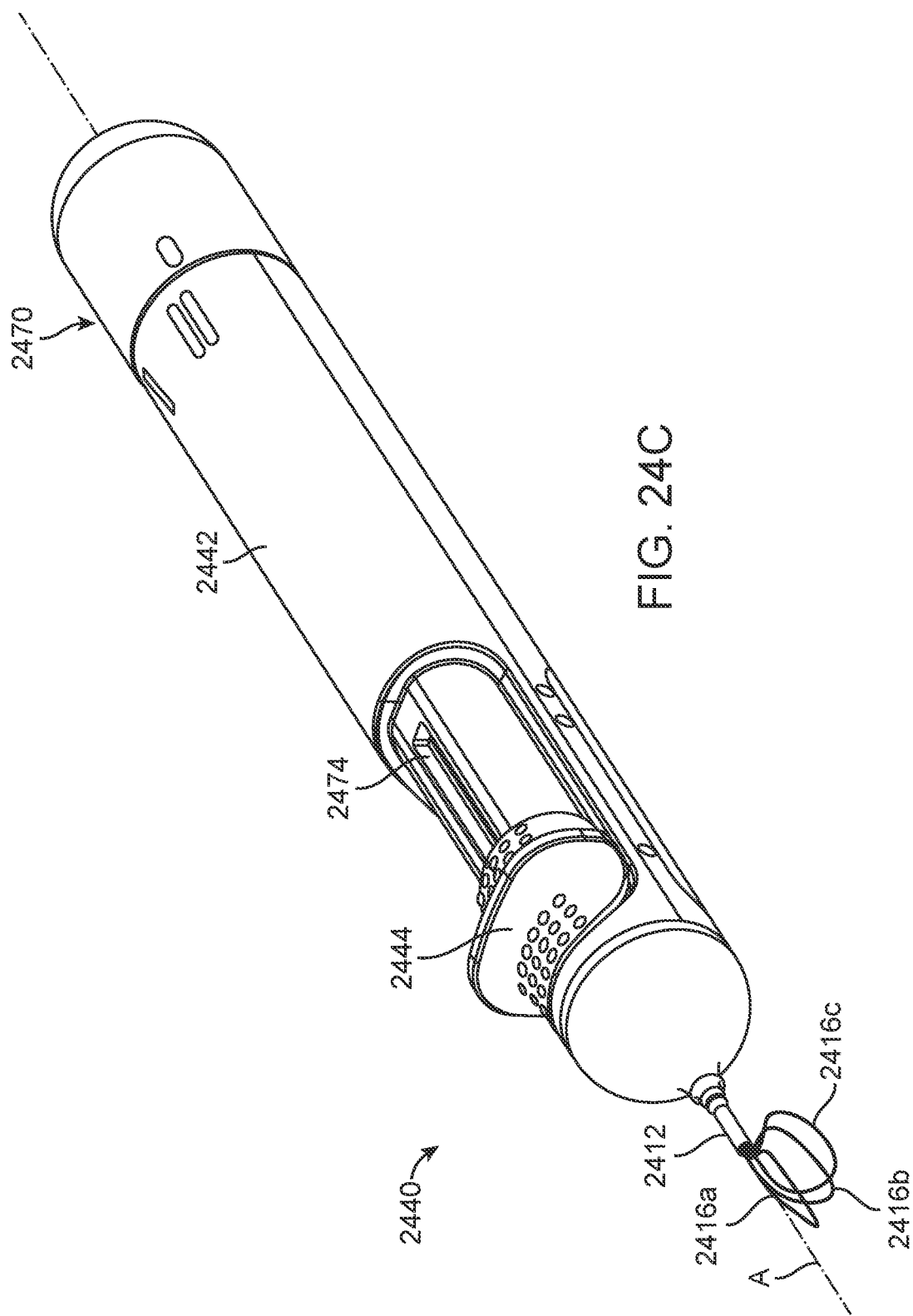
FIG. 24C is a perspective view of the device of FIG. 24B in a third, splayed configuration.
Figure 24D:
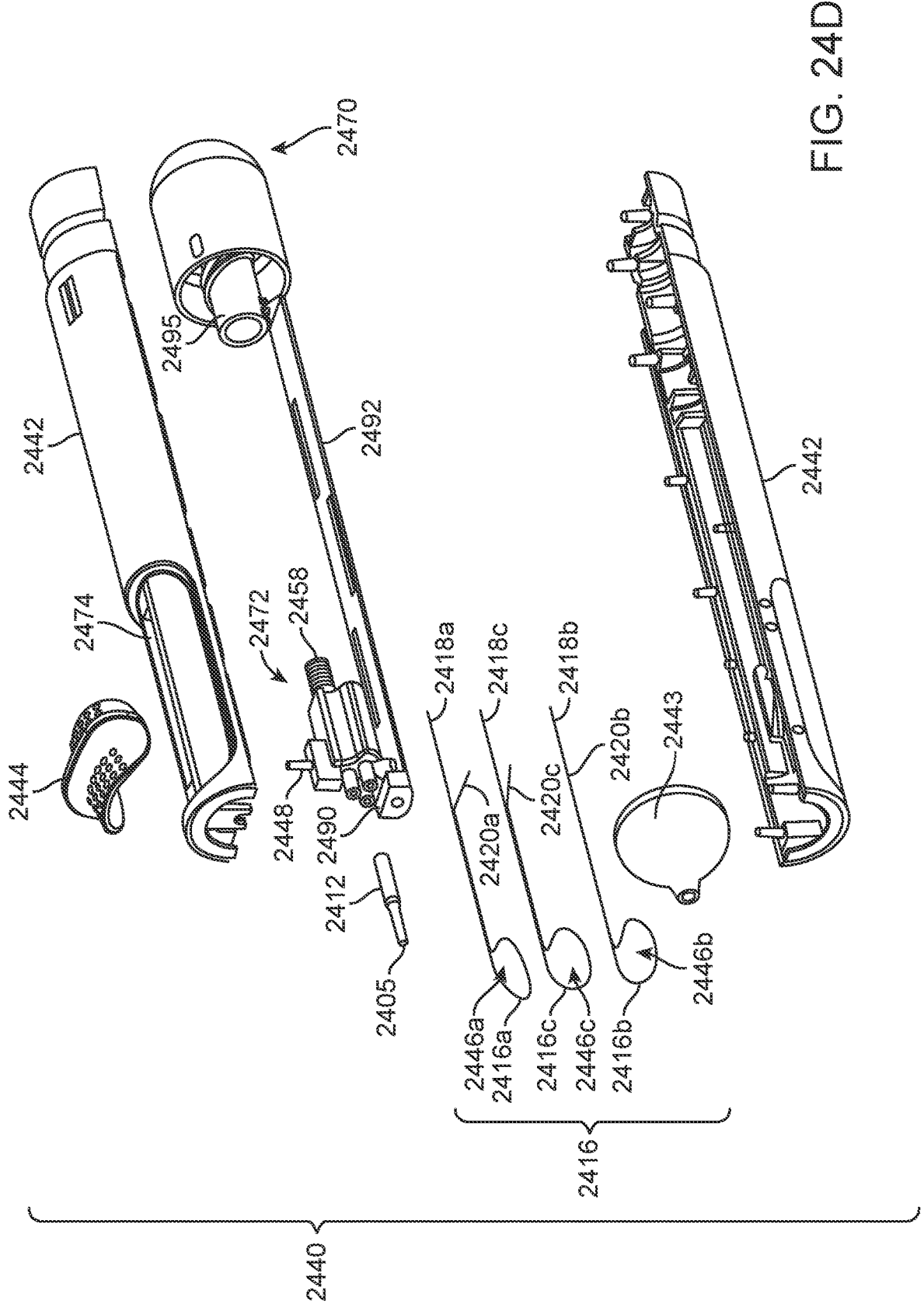
FIG. 24D is an exploded view of the device of FIG. 24A having three sectioning elements.

In an implementation, the sectioning element 2416 can include three sectioning elements 2416a, 2416b, 2416c in which an intermediate loop or sectioning element 2416b is positioned generally between the first and second sectioning elements 2416a, 2416c (see FIG. 24D). The intermediate sectioning element can likewise include a first end, a second, end, and a distal loop formed between the first and second ends. When the cutting element is transitioned towards the second, expanded configuration, the distal loop of the intermediate sectioning element may define an enlarged open area located outside the distal end of the shaft 2412. The enlarged open area may have a first leg advanced distally relative to the distal end of the shaft and a second leg positioned proximally to the distal end of the shaft. In this implementation, the sectioning elements 2416a, 2416b, 2416c are configured to expand from the first, retracted configuration (FIG. 24A) to the second, expanded configuration (FIG. 24B) and to the third, splayed configuration (FIG. 24C). The enlarged open areas of each of the first, second, and intermediate sectioning elements may be aligned generally parallel to one another within a plane when in the second, expanded configuration. In the third, splayed configuration the outer two sectioning elements 2416a, 2416c can be moved angularly away from the intermediate sectioning element 2416b. A second activation of an actuator or a second, different actuator may cause the enlarged open areas of both the first and second sectioning elements to move angularly away from the intermediate sectioning element transitioning the cutting element into a third, splayed configuration. The sectioning elements 2416a, 2416b, 2416c can be actuated to move from the collapsed position toward the unbiased shape of the expanded position, for example via a slider 2444 or other actuation mechanism positioned on the housing 2442. The sectioning elements 2416a, 2416b, 2416c can also be actuated to move toward the third, splayed configuration via the slider 2444 and/or another actuation mechanism positioned on the housing 2442. As will be described in more detail below, the device 2440 can include a two-phase deployment in which expansion of the loops to the second, expanded configuration can be performed independently of the splay in the third, splayed configuration.

As described elsewhere herein, the sectioning elements 2416 can be formed of a superelastic metal and/or polymer material. The housing 2442 of the device 2440 can be formed of a relatively rigid, lightweight material(s). The shaft 2412 coupled to a distal end region of the housing 2442 can have a lumen extending through it to a distal outlet 2405. The shaft 2412 can be oval in cross-section with a rounded tip. The oval cross-section enhances the ability of the shaft 2412 to be inserted into the eye 1 through the corneal incision 4. The oval cross-section also allows for a side-by-side arrangement of the plurality of sectioning elements 2416a, 2416b, 2416c within the lumen. Alternately, the shaft 2412 may have a circular cross-section or a cross-section of any other suitable shape.

The distal end of the sectioning elements 2416 can extend out of the outlet 2405 from the lumen when in the first, retracted configuration (see FIG. 24A). In such embodiments, the tight radius bend 2424 may be positioned outside the shaft 2412, already bent at least partially toward the proximal direction (see FIG. 24B). In this way, even in implementations where the sectioning element 2416 is fabricated from superelastic material, the angle through which a portion of the sectioning element 2416 is bent during transition from the first, retracted configuration to the second, expanded configuration is reduced. Further, less space may be required within the lumen of the shaft 2412 to hold part of the sectioning element 2416 than to hold all of it, allowing the shaft 2412 to be made smaller in diameter. Alternately, the entirety of the sectioning elements 2416 can be positioned within the lumen of the shaft 2412 when in the first, retracted configuration. The distal end of the sectioning element 2416, whether inside or outside the lumen in the first, retracted configuration, is sized and shaped to pass through a clear corneal incision 4 without damaging the eye 1. Generally, clear corneal incisions 4 are less than about 3.5 mm, although this size can vary. The maximum outer diameter of the distal end region of the shaft 2412 including the sectioning elements 2416 in the first, retracted configuration can be less than about 3.5 mm such that they may be inserted through a clear corneal incision, for example, between about 1.5 mm and 3.5 mm.

As described elsewhere herein and as shown in FIG. 26A, each of the sectioning elements 2416 can include a first end 2418 and a second end 2420, at least one of which is moveable relative to the shaft 2412. For example, one end (e.g. the first end 2418) of the sectioning elements 2416 may be fixed relative to the shaft 2412 and another end (e.g. the second end 2420) of the sectioning elements 2416 may be movable relative to the shaft 2412. When the movable end is pushed distally (i.e. axially along the longitudinal axis of the device), the sectioning elements 2416 translate from the first, retracted configuration toward the second, expanded configuration. When the movable end is withdrawn proximally, if allowed, the sectioning elements 2416 translate from the second, expanded configuration toward the first, retracted configuration. It should be appreciated that both ends 2418, 2420 can be movable relative to the shaft 2412 as described elsewhere herein and as will be described in more detail below. Use of the terms "first," "second," or "third" are not intended to be limiting and may be interchangeable herein, except where explicitly described as otherwise.

The sectioning elements 2416 upon extension out of the lumen of the shaft 2412 can have a distal end region or a distal loop that approximates or defines an open area generally in the shape of an irregular loop having a cross-section of a native lens 8. This allows the enlarged open area 2446 of the sectioning elements 2416 to surround the lens 8 within the capsular bag 6. As the end or ends 2418, 2420 are pushed distally out from the lumen, the sectioning elements 2416 transition to the second, expanded configuration. As the sectioning elements 2416 transition out of the shaft 2412, the tight radius bend 2424 allows the proximal section of the sectioning elements 2416 to extend proximally from the distal end of the shaft 2412, at a location spaced from and to one side of the longitudinal centerline of the lumen 2412 (i.e. longitudinal axis A of the device 2440) in the direction toward the capsular bag 6. In this way, the sectioning elements 2416 are able to extend downward through the capsulorhexis 10 and expand to a length within the capsular bag 6 that is greater than the diameter of the capsulorhexis 10. For example, the sectioning elements 2416 can be movable relative to the shaft 2412 from the first, retracted configuration toward a second, expanded configuration in which the larger portion of each sectioning element 2416 extends out of the distal end of the lumen 2450. At least a portion of the sectioning elements 2416 are positioned within the lumen when in the first, retracted configuration. It should be appreciated that some of the sectioning elements 2416 can extend outside the lumen, but that the sectioning elements 2416 and the shaft 2412 are still sized for insertion into an anterior chamber of an eye through a small corneal incision (e.g. a clear corneal incision). Motion from the first, retracted configuration toward the second, expanded configuration can cause at least one of the ends 2418, 2420 to advance distally relative to the distal end of the shaft 2412 to form the open area 2446, the open areas 2446 bounded by their respective sectioning elements 2416 and the distal end 2405 of the shaft 2412. At least a portion of the sectioning elements 2416 bounding the open area 2446 extends proximally relative to the distal end 2405 of the shaft 2412. The second, expanded configuration of the sectioning elements 2416 is sized and shaped to permit advancement of the sectioning elements 2416 between the capsular bag 6 and the lens 8 of the eye while the lens remains in the capsular bag 6 to capture a portion of the lens 8 within the open area 2446.

As the sectioning elements 2416 continue to expand, the plane formed by the sectioning elements 2416 can be rotated so that the sectioning elements traverse a space between the capsular bag 6 and the lens 8. The shape plane can be rotated to be primarily vertical or to any number of other angles relative to vertical. The rotation may be accomplished by manual rotation of the shaft 2412 of surgical device 2440 by the user. The rotation may be accomplished by integrated mechanisms within the surgical device 2440, as described elsewhere herein.

Figure 26B:
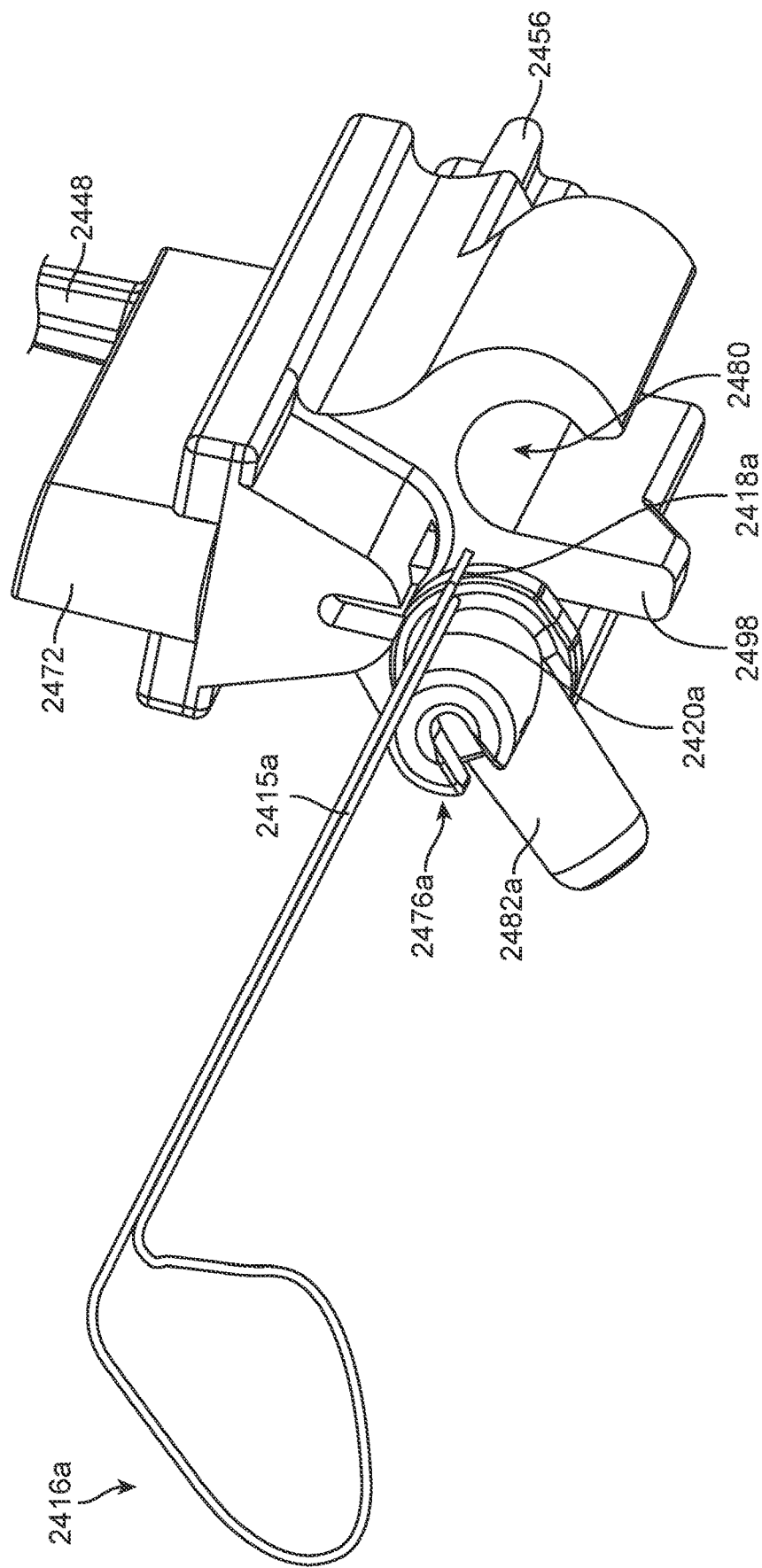
FIG. 26B is a partial, perspective view of the device of FIG. 24A illustrating the sled and loop carriers.
Figure 26C:
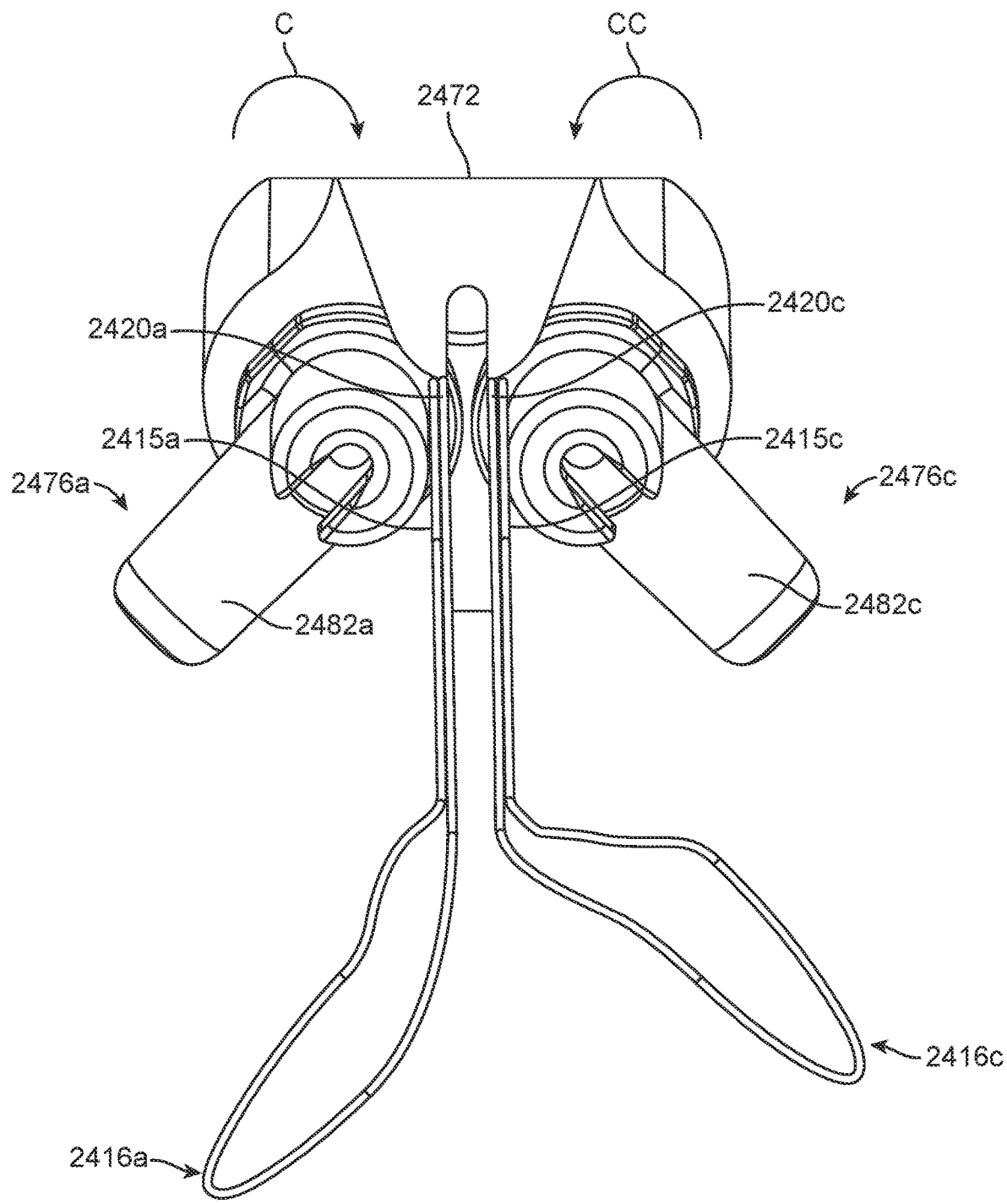
FIG. 26C is a partial, end view of the device of FIG. 24A.

As mentioned above, the device 2440 includes an actuator to tension the sectioning elements 2416 to reduce the size of the open areas 2446 and cut the lens 8. The actuator can be a slider 2444 movable relative to the housing 2442 such as along the longitudinal axis of the housing. The slider 2444 can be slideable along the top surface of the housing 2442. It should be appreciated that use of the term "slider" is not intended to be limiting and other configurations of actuator are considered here. For example, the actuation mechanism can be a button, switch, knob, or other interface element. As best shown in FIG. 26A-26C, the slider 2444 can be operatively coupled to a sled 2472 located within an interior of the housing 2442 via one or more fingers 2448 that extend upwards through a slot 2474 in the top surface of the housing 2442. The finger(s) 2448 can couple to an undersurface of the slider 2444. The slider 2444 and sled 2472 are movable within the interior of the housing 2442 along the longitudinal axis A of the housing 2442. As shown in FIG. 26A, a plurality of loop carriers 2476 can be coupled to the sled 2472 having an arm 2482 and a proximal post 2478. The arm 2482 can extend outward from the proximal post 2478. The proximal post 2478 can be generally cylindrical and configured to be received through a corresponding bore 2480 of the sled 2472 (see FIG. 26B) and configured to rotate around its respective axis of rotation within the bore 2480.

As mentioned, the proximal post 2478 is configured to rotate around its respective axis of rotation within its respective bore 2480. The sled 2472 can be coupled to first and second loop carriers 2476a, 2476c positioned on either side of the longitudinal axis A of the device 2440 (see FIG. 26C-26E). The rotation of the loop carriers 2476a, 2476c around their respective axes of rotation $R_1$, $R_2$ and thus, the rotational movement of the arms 2482a, 2482c can be mirror image. FIG. 26D illustrates the loop carriers 2476a, 2476c prior to splay. The arms 2482a, 2482c of the loop carriers 2476a, 2476c are positioned in a substantially vertical position such that they are arranged substantially parallel to one another. During splay, the loop carrier 2476a positioned on a first side of the longitudinal axis A rotates a first direction around its axis of rotation $R_1$ (e.g. clockwise) and the loop carrier 2476c positioned on the opposite side of the longitudinal axis A rotates a second direction around its axis of rotation $R_2$ (e.g. counter-clockwise). The arms 2482a, 2482c splay outward away from the substantially vertical starting position (e.g. orthogonal to the longitudinal axis A) to a substantially non-vertical position. The amount of rotation achieved by each of the arms 2482a, 2482c can vary, but is generally between about 15 degrees to about 45 degrees relative to the vertical starting position.

The rotation of the loop carriers 2476 causes a corresponding rotation in the distal loops defining the enlarged open areas 2446 of the sectioning elements 2416 and thereby transitions the cutting element into the splayed configuration. The splayed configuration of the cutting element can vary. As described throughout, the distal loops defining the enlarged open areas may move angularly away from one another transitioning the cutting element into the splayed configuration, the angular movement being relative to a plane of the longitudinal axis of the device (or the longitudinal axis of the shaft or the longitudinal axis of the lumen through which the cutting element extends). When the cutting element is in an expanded configuration such that the open areas defined by the distal loops are expanded or otherwise enlarged away from their initial insertion configuration (typically referred to herein as a retracted configuration), the distal loops defining the open areas can be arranged generally parallel to one another within a plane, such as a vertical plane, relative to the longitudinal axis of the shaft. It should be appreciated that when the distal loops and their enlarged opening areas are generally aligned with the plane parallel with each other one or more portions of that distal loop may extend outside the plane. Meaning, that the enlarged open areas defined by the distal loops may take on a shape that is not flat (see, e.g., sectioning element 16 shown in FIG. 2), but the enlarged open areas of the sectioning elements may be arranged substantially parallel to one another and substantially within a plane relative to the device when in the second, expanded configuration. It should also be appreciated that the enlarged open areas need not be fully enlarged in order to be splayed relative to one another. Thus, where the second, expanded configuration is referred to herein it need not require the distal loops be expanded to their maximally expanded configuration. The second, expanded configuration can include an enlarged configuration in which the enlarged open areas defined by the distal loops are expanded to less than a maximal expansion before they are splayed relative to one another. FIG. 24B shows sectioning elements 2416 having enlarged open areas 2446 that have expanded in generally two directions (i.e. along an X and Y axis) and are not yet splayed such that they are still generally compressed against each other (i.e. along the Z axis). FIG. 24C shows the sectioning elements 2416 in the splayed configuration where the one or more of the distal loops defining the enlarged open areas have moved angularly away from one another (e.g. along the Z axis). In some implementations, the cutting element has two sectioning elements and the distal loops defining the enlarged open areas of the two sectioning elements splay apart a distance in the Z axis. One region of the enlarged open area of each distal loop (i.e. a region aligned with the longitudinal axis of the lumen of the shaft 2412) can remain generally compressed against a neighboring distal loop while another region of the enlarged open area (i.e. a region below the longitudinal axis of the lumen of the shaft 2412) can splay apart from the neighboring distal loop. This region of the loop that rotated and is thus splayed apart can be positioned at an angle relative to a plane of the longitudinal axis of the shaft. The angle can vary, for example, between about 15 degrees relative to the plane up to about 45 degrees relative to the plane.

One or more of the sectioning elements 2416 can have a fixed, first end 2418 and a movable, second end 2420. For example, the movable, second ends 2420 of sectioning elements 2416a, 2416c are capable of movement along the longitudinal axis A of the device 2440 such that they may be deployed into the second, expanded configuration (see FIGS. 26B-26C). The movable, second ends 2420a, 2420c of the outer two sectioning elements 2416a, 2416c are additionally capable of angular movement with respect to the longitudinal axis A. The second end 2420b of the intermediate sectioning element 2416b (shown in FIG. 24D) may be fixed such that it does not rotate or move angularly relative to the longitudinal axis A. For example, the fixed, first end 2418a of a first sectioning element 2416a may be fixed such that it remains stationary during actuation and the movable, second end 2420a of the first sectioning element 2416a may be configured to be moved relative to the longitudinal axis A of the device 2440 along at least two planes. Similarly, the fixed, first end 2418c of a second sectioning element 2416c may be fixed such that it remains stationary during actuation and the movable, second end 2420c of the second sectioning element 2416c may be configured to be moved relative to the longitudinal axis A of the device 2440 along at least two planes. The fixed, first end 2418b of the intermediate sectioning element 2416b may be fixed such that it remains stationary during actuation and the moveable, second end 2420b of the intermediate sectioning element 2416b may be configured to be moved relative to the longitudinal axis A of the device 2440. However, the intermediate sectioning element 2416b may be configured to move along a single plane and may not be capable of rotational or angular movement relative to the longitudinal axis A. As such, all three sectioning elements 2416a, 2416b, 2416c can be configured to expand upon actuation of the slider 2444, for example, by movement of their respective movable, second ends 2420a, 2420b, 2420c along the longitudinal axis A of the device 2440. The outer two sectioning elements 2416a, 2416c may have movable, second ends 2420a, 2420c additionally capable of angular rotation relative to the longitudinal axis A. The movable, second end 2420b of the intermediate sectioning element 2416b can be fixed such that it does not move. It should be appreciated that the relative splaying movements of the plurality of sectioning elements 2416 can vary and this is an example of how splay may occur. Each of the plurality of sectioning elements 2416 can have an end capable of translation along the longitudinal axis A of the device as well as rotational and/or angular movements relative to the longitudinal axis A.

With respect to FIGS. 26B-26E, the rotational movement of the loop carriers 2476 around their respective axes of rotation $R_1$, $R_2$ provides the rotational angular displacement that causes the outer sectioning elements 2416a, 2416c to splay apart from the intermediate sectioning element 2416b. One or more of the sectioning elements may not be shown in the figures for clarity. In an implementation, the fixed, first ends 2418a, 2418b, 2418c of each of the three sectioning elements 2416a, 2416b, 2416c can be coupled to a region of the housing 2442 or other non-moving component of the device 2440. The movable, second ends 2420a, 2420c of the outer two sectioning elements 2416a, 2416c can be coupled to distal-facing surfaces of their respective loop carriers 2476. For example, a first of the loop carriers 2476a can couple to the movable, second end 2420a of the first sectioning element 2416a and the second of the loop carrier 2476c can couple to the movable, second end 2420c of the second sectioning element 2416c (see FIG. 26C). As the loop carriers 2476a, 2476c rotate around their rotational axes $R_1$, $R_2$, the ends 2420a, 2420c translate along with them around the rotational axes $R_1$, $R_2$ towards the third, splayed configuration. FIG. 26C illustrates the third, splayed configuration in which the first loop carrier 2476a has rotated clockwise (arrow C) such that the arm 2482a splays to the left away from vertical and the second loop carrier 2476c has rotated counter-clockwise (arrow CC) such that the arm 2482c splays to the right away from vertical. The movable ends 2420a, 2420c of the sectioning elements 2416a, 2416c travel along with the loop carriers 2476a, 2476c towards the longitudinal axis A of the device 2440 causing the loops to splay outward away from the longitudinal axis A. The movable, second end 2420b of the intermediate sectioning element 2416b (not shown in FIG. 26C) can be coupled to the sled 2472 such that movements of the loop carriers 2476 do not impact its position relative to the longitudinal axis A.

Figure 24E:
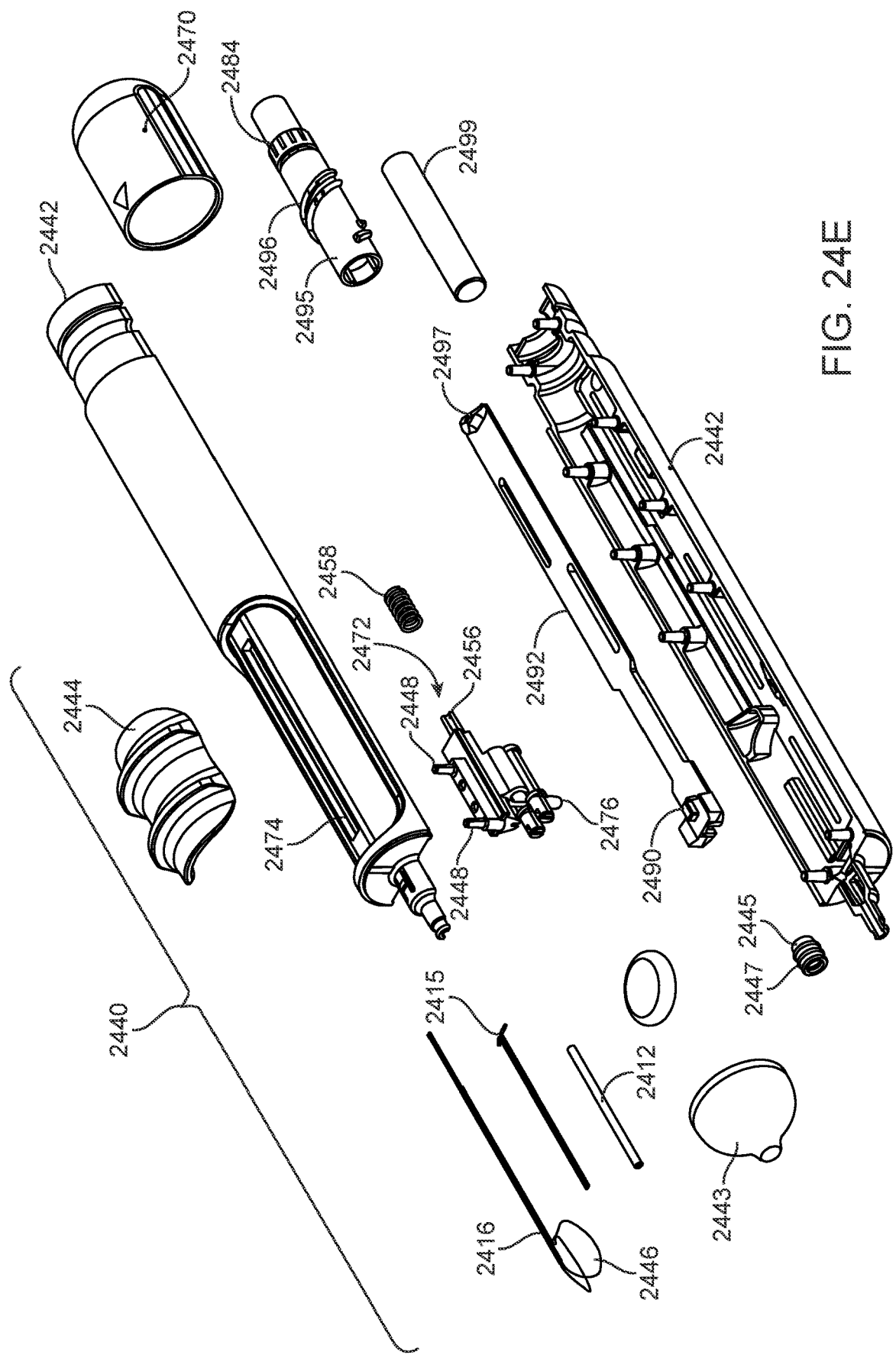
FIG. 24E is an exploded view of another implementation of the device of FIG. 24A having two sectioning elements.

In some implementations, the device 2440 can further include a small diameter, thin-walled sleeve 2415 that is configured to move relative to the longitudinal axis of the device (see FIG. 24E). At least a portion of the plurality of sectioning elements 2416 can extend through the sleeve 2415. When the sleeve 2415 is advanced distally over a greater length of the sectioning elements 2416, the sleeve 2415 prevents the sectioning elements 2416 from splaying away from one another and/or away from the longitudinal axis A of the device 2440 even when their loops are expanded. When the sleeve 2415 is retracted towards a proximal end of the device 2440, the sectioning elements 2416 are free to splay. The retraction of the sleeve 2415 can be performed manually by a user. Alternatively, the retraction of the sleeve 2415 can occur automatically during the phases of deployment of the sectioning elements 2416. The sectioning elements 2416 are configured to expand from the first, retracted configuration to a second, expanded configuration. The sleeve 2415 can be positioned around a length of the sectioning elements 2416 in a manner that allows for their respective loops to achieve the enlarged state, but prevents splaying or angular movement of the sectioning elements 2416 relative to the longitudinal axis. Actuation of the sectioning elements 2416 from the second, expanded configuration towards the third, splayed configuration can also retract the sleeve 2415. Retraction of the sleeve 2415 can occur in a step-wise manner (retract, then splay) such that splay of the sectioning elements 2416 relative to the longitudinal axis is possible. Each sectioning element 2416 may be rigidly coupled to its respective sleeve 2415. Where the device includes a single sectioning element 2416, a single sleeve 2415 may be incorporated. Where the device includes two sectioning elements 2416, two sleeves 2415 may be incorporated, one for each sectioning element 2416 and so on. Each sleeve 2415 allows for longitudinal, lateral, and rotational motion of its sectioning element 2416. Longitudinal motion allows for extension and expansion of the distal loops beyond the distal opening 2405 of the shaft 2412. Lateral and rotational motion allows for splay or fanning of the distal loops. The sleeves 2415 for each sectioning element 2416 aid in preventing "wind up" of the wires when the sectioning elements 2416 are manipulated and provide sufficient torsional stiffness for extension and splay.

Figure 26F:
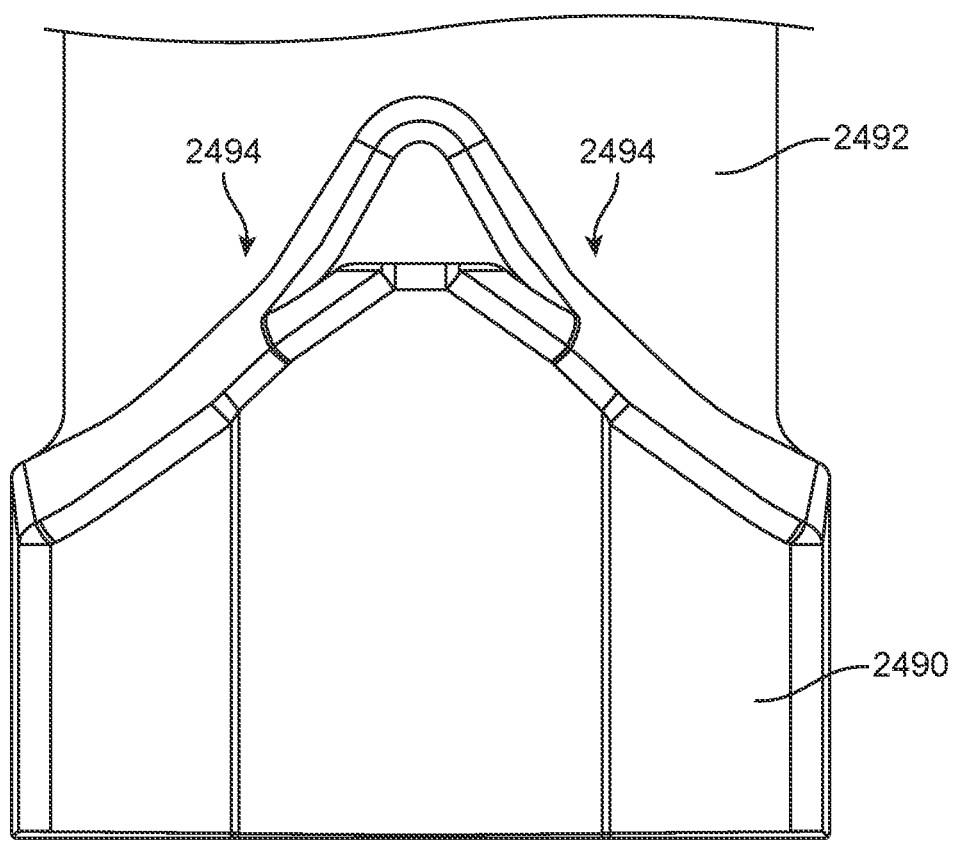
FIG. 26F is a top plan view of the wedge of the device of FIG. 24A.
Figure 26I:
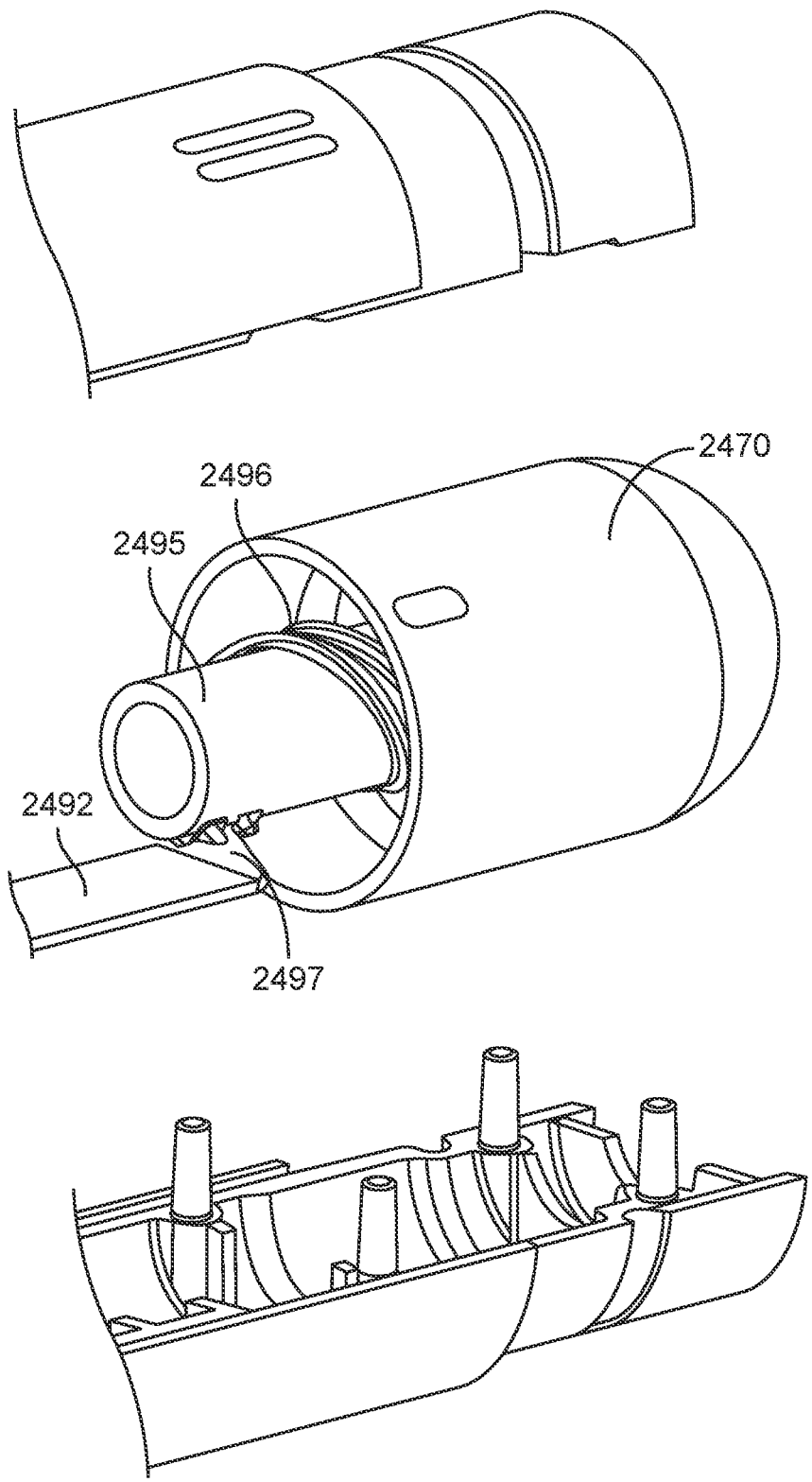
FIGS. 26I-26L are various views of the expansion adjustment mechanism.
Figure 26J:
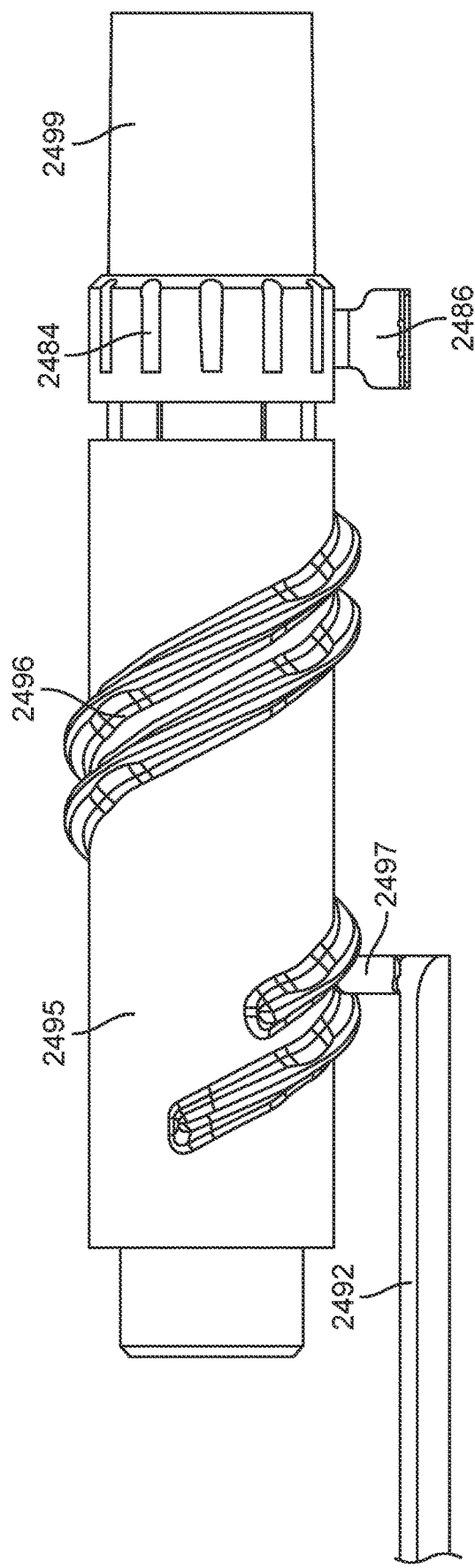
Figure 26K:
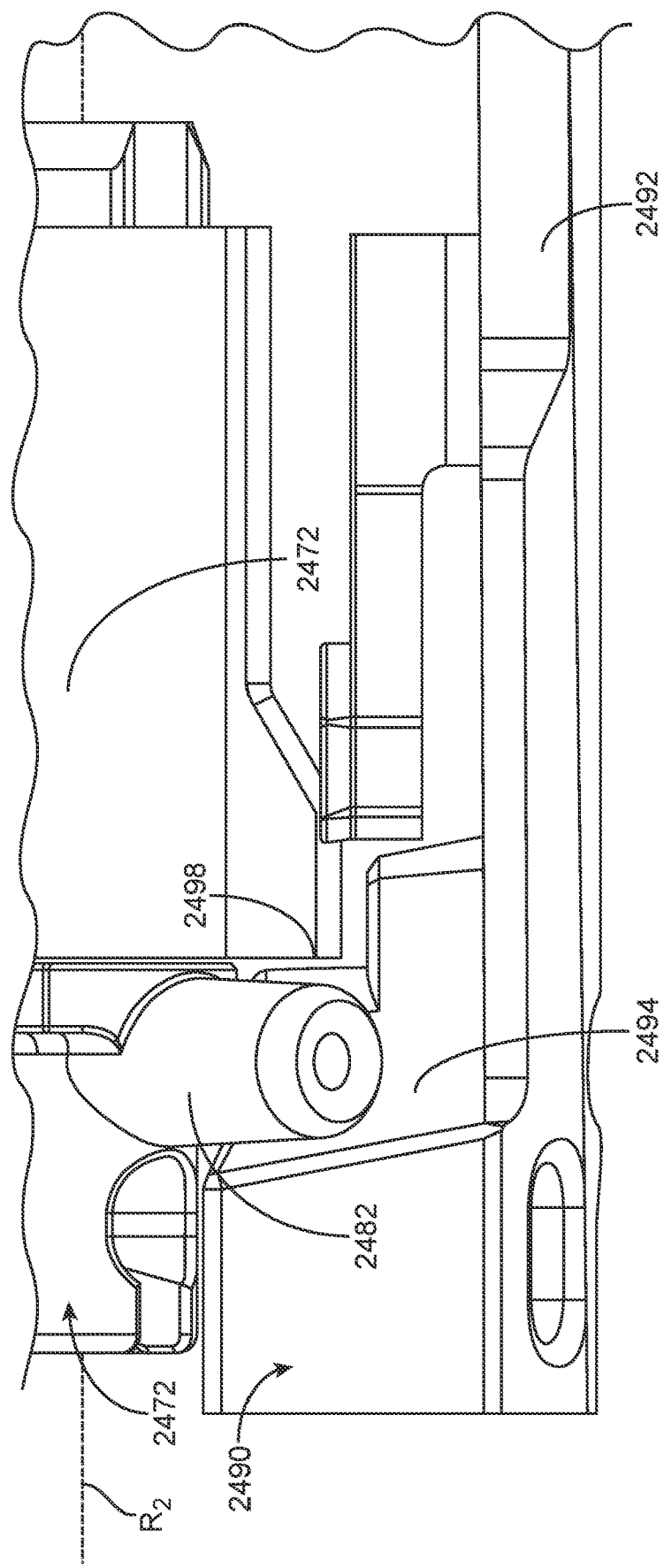
Figure 26L:
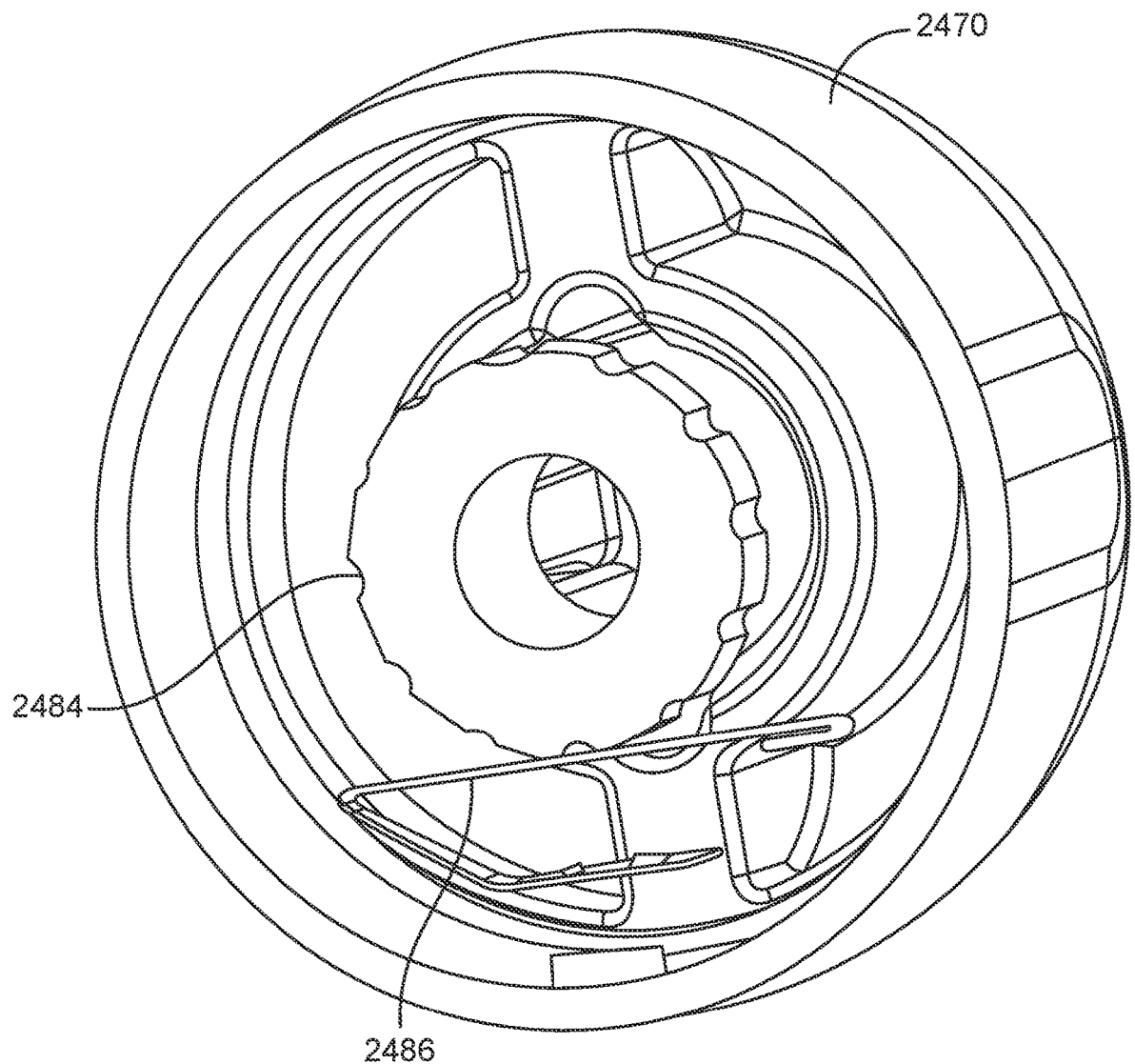

The arms 2482 of the loop carriers 2476 can be urged into the splayed configuration by a wedge 2490 positioned on a wedge sled 2492. The wedge 2490 can be positioned in a distal end region of the housing and have a ramped surface 2494 facing towards a proximal end of the device 2440. Movement of the arms 2482 against the wedge 2490 causes the arms 2482 to be urged away from one another and splay outward (see FIGS. 26D-26F). As discussed above, the loop carriers 2476 can be coupled to the sled 2472 that can slide along the longitudinal axis A of the device 2440 with the slider 2444. Distal movement of the sled 2472 can force the arms 2482 of the loop carriers 2476 to abut against the wedge 2490 and slide along the ramped surface 2494. The arms 2482 can rotate around their respective rotational axes such that they splay away from one another as they slide along the ramped surface 2494 in a distal direction towards the thicker portion of the wedge 2490. In some implementations, the wedge 2490 is movable in a proximal direction and can be moved against the sled 2472 to play the arms 2482 of the loop carriers 2476.

The deployment can be a step-wise deployment including an expansion step followed by a splay step. The deployment can also be a step-wise deployment including an expansion step followed by a rotation step followed by a splay step. If the device includes the retractable sleeve 2415 controlling splay of the sectioning elements, the step-wise deployment can further include a sleeve retraction step prior to or in combination with the splay step. Sliding movement of the slider 2444 relative to the housing 2442 moves the sled 2472 a first distance to achieve expansion of the loops from the first, retracted configuration towards the second, expansion configuration. Sliding movement of the slider 2444 relative to the housing 2442 moves the sled 2472 a second distance beyond the first distance to achieve splay of the loops (i.e. the third, splayed configuration). Rotation of the expanded loops is described elsewhere herein as involving a mechanical element within the device itself or performed can be performed by a user.

Figure 26M:
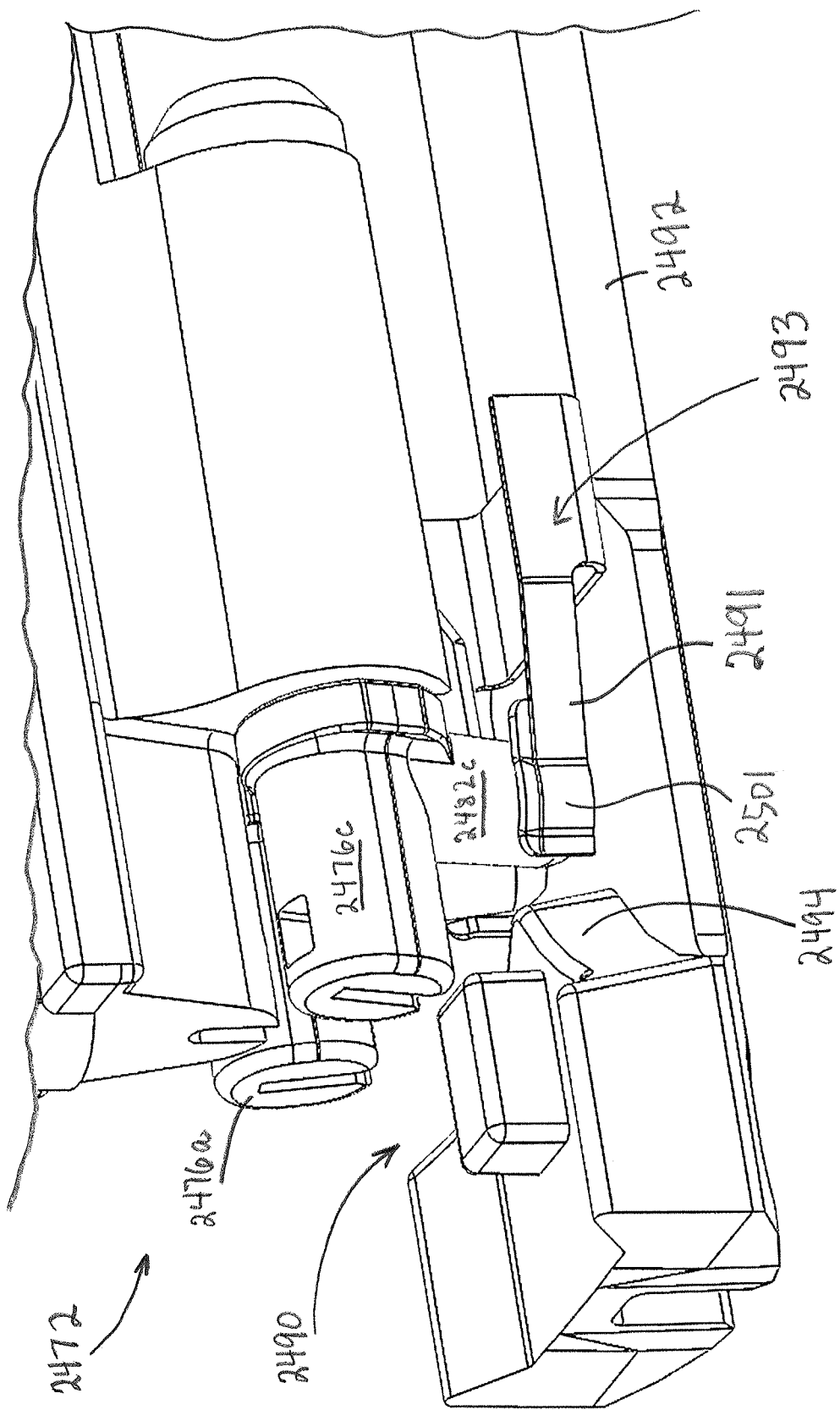
FIG. 26M is a partial, perspective view illustrating the loop carrier of the device of FIG. 24A prior to splay illustrating an implementation of a user feedback element.
Figure 26N:
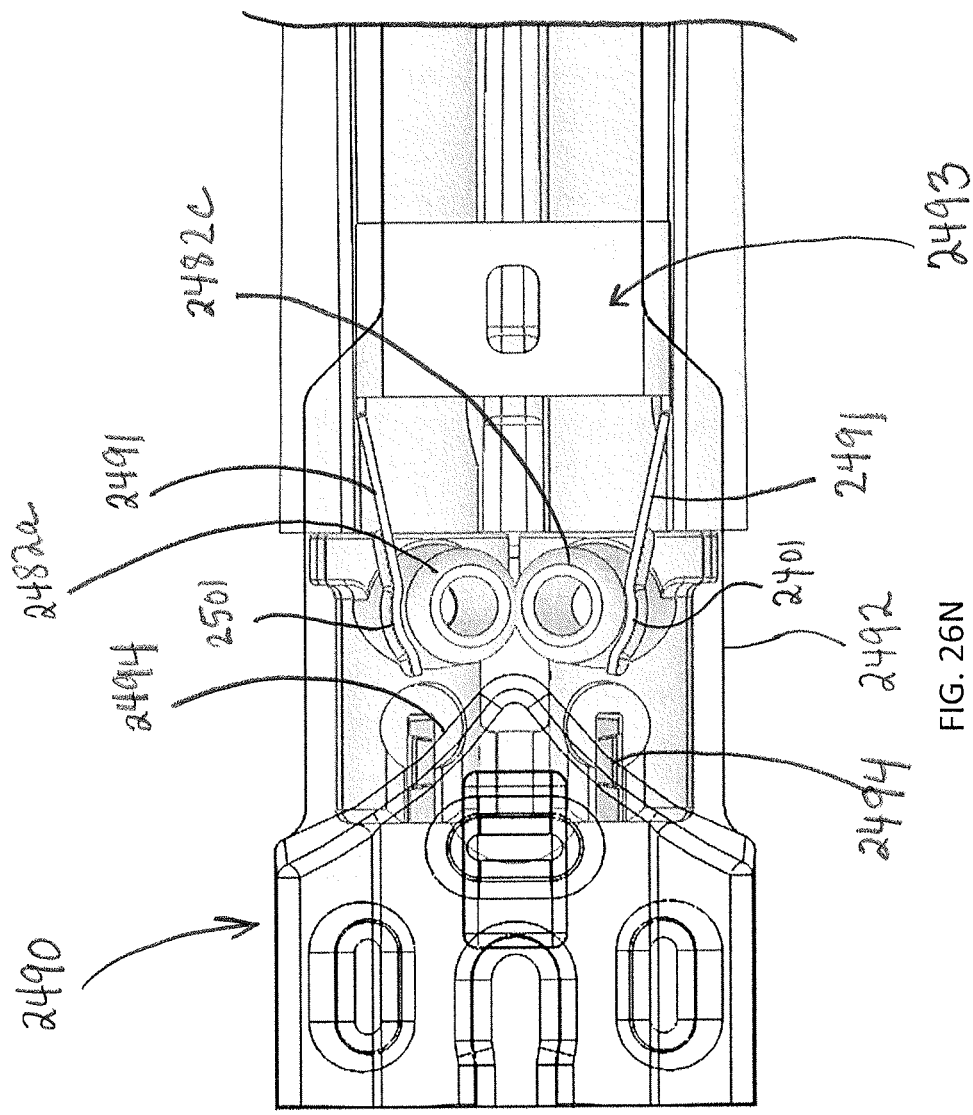
FIG. 26N is a top plan view of the user feedback element of FIG. 26M.

The splay mechanism can further include an element configured to provide user feedback regarding where in the first deployment phase the slider 2444 is positioned. For example, as best shown in FIGS. 26M and 26N, the user feedback element 2493 can be a splay detent spring configured to contact the loop carriers 2476 immediately before the arms 2482 start to splay. The user feedback element 2493 can be coupled near the distal end region of the housing 2442 just proximal to the ramped surface 2494 facing towards the proximal end of the device 2440. The user feedback element 2493 can include two springs 2491 biased towards a centerline of the wedge sled 2492, the distal ends of the springs 2491 located just proximal to the ramped surface 2494 of the wedge 2490. As the slider sled 2472 moves axially in a distal direction relative to the wedge sled 2492, the arms 2482 of the slider sled 2472 slide between the springs 2491. The distal ends of the springs 2491 may be positioned closer to one another than the proximal ends of the springs 2491 such that the springs 2491 flex away from the centerline of the wedge sled 2492 and from each other as the arms 2482 past between them in a distal direction. Each spring 2491 may include a detent 2501 near an inner surface of its distal end region. The detent 2501 forms a concavity sized and shaped to receive an outer diameter of its respective arm 2482. Upon reaching the location of the detent 2501, the arms 2482 snap into its detent 2501 providing tactile and/or audible feedback that indicates to a user that the arms 2482 are about to contact the ramped surfaces 2494 of the wedge 2490 if the slider 2444 is extended further distally. Upon further distal extension of the slider 2444, the arms 2482 pass beyond the detents 2501 of the springs 2491 and abut against the proximally facing ramped surfaces 2494 of the wedge 2490 to begin their rotation In some configurations, an initial, long distally-directed movement of the slider 2444 achieves the second, expanded configuration and a final, short distally-directed movement of the slider 2444 beyond this achieves the third, splayed configuration. This step-wise deployment can expand the loops upon a first actuation (i.e. sliding the slider 2444 a first distance) and can splay the loops upon a second actuation (i.e. sliding the slider 2444 a second distance beyond the first distance). In some configurations, the third, splayed configuration is achieved by proximally-directed movement of the wedge 2490 towards the arms 2482. In this configuration, the relative position of the slider sled 2472 and thus, the arms 2482 of the loop carriers 2476 can remain fixed along the longitudinal axis A and the wedge 2490 on the wedge sled 2492 can be moved in a proximal direction towards the arms 2482. For example, the loops or open areas 2446 can be expanded upon a first actuation (i.e. sliding the slider 2444 a first distance in the distal direction) and the loops or open areas 2446 can be splayed upon a second actuation (i.e. withdrawing the wedge 2490 in the proximal direction). It should be appreciated that the second actuation can be performed using the slider 2444 or an actuator independent of the slider 2444, as will be described in more detail below. This allows for the splayed configuration to be achieved regardless of the overall expansion of the loops while still providing the step-wise, two phase deployment. As such, even when the size of expansion is limited to a size smaller than a maximum expansion, the individual loops of the sectioning elements 2416 may still be splayed from one another. Thus, the distal loops of the sectioning elements are configured to splay angularly away from each other transitioning the cutting element into the third, splayed configuration independent of the size of the enlarged open areas.

The device 2440 allows for a user to fully adjust and select at what point during wire extension the loops will begin to separate angularly from one another. As described elsewhere herein, the second, expanded configuration of the sectioning elements 2416 can be generally oval in shape with a maximum width of about 4.0 mm to about 20 mm, and a height of about 1.0 mm to about 15 mm. In some implementations, the second, expanded configuration of the sectioning elements 2416 can be manually adjustable by a user such that the size of the open area 2446 that can be achieved upon full deployment is less than a maximum size of the open area 2446 when the sectioning element 2416 is unconstrained. The second, expanded configuration of the sectioning elements 2416 may be limited to an intentionally smaller size than the lens 8 at certain areas or along the entire profile. This may improve the ability of the sectioning elements 2416 to remain close to the lens 8 and reduce interaction with the capsular bag 6. Limiting the size of the open area 2446 of the sectioning elements 2416 to one that is less than a maximum dimension allows for the sectioning elements 2416 to also be used as tissue manipulators to capture small fragments of lens material to remove them from the capsular bag. This may eliminate the need for a second removal device to be used.

The maximum size of open space 2446 achievable from the sectioning elements 2416 upon actuation of the slider 2444 and prior to splay can be manually adjusted by a user. FIGS. 26G-26L illustrate an expansion adjustment mechanism including an adjustor 2470 positioned on the housing 2442. In some implementations, the adjustor 2470 can be a rotatable knob, push button, switch, slider, or other feature configured to be actuated by a user. It should be appreciated, use of the terms "knob" or "slider" are not intended to be limiting and that any of a variety of user inputs are considered herein that can be actuated by a user to achieve extension and/or splay of the sectioning elements 2416. The size of the enlarged open areas of the sectioning elements prior to splay may be selectable by a user, for example, by using an adjustor configured to change a relative distance between the wedge and the sled. A shorter relative distance between the wedge and the sled can result in a smaller open area of the sectioning elements when urged into the second, expanded configuration prior to splay and a longer relative distance between the wedge and the sled can result in a larger open area of the sectioning elements when urged into the second, expanded configuration prior to splay.

In an implementation, the adjustor 2470 is rotatably coupled to a proximal end of a cam 2495 such that rotation of the adjustor 2470 causes the cam 2495 to rotate. The adjustor 2470 can be coupled directly to the proximal end of the cam 2495 or to a dowel 2499 extending through the cam 2495 (see FIG. 26J). The proximal end of the cam 2495 can include a mechanism that provides a step-wise rotation providing a series of tactile or audible clicks providing user feedback as to the degree of rotation achieved. In some implementations, the mechanism can include a plurality of detents 2484 positioned near a proximal end of the cam 2495 arranged to interface with a spring 2486, such as a leaf spring. The spring 2486 can have an end configured to flex upward away from the longitudinal axis such that it slides over the proximal end of the rotating cam 2495 and the flex downward to insert within each detent 2484. The spring 2486 can provide a detent force as a user turns the thread. The cam 2495 can have a helical cam path 2496 on an outer surface that is configured to engage with a cam post 2497 located at a proximal end of the wedge sled 2492. As the adjustor 2470 is rotated a first direction the cam post 2497 of the wedge sled 2492 travels along the helical cam path 2496 around the cam 2495 thereby sliding the wedge sled 2492 along the longitudinal axis A of the device 2440. The wedge 2490 at a distal end of the wedge sled 2492 is moved towards the proximal end of the device 2440. As the wedge 2490 is withdrawn in a more proximal location along the longitudinal axis A of the device, the loops or open areas 2446 of the sectioning elements 2416 will splay earlier in the expansion stroke. Meaning, the open area 2446 of the respective sectioning elements 2416 will be smaller at the time of splay. The opposite movement can occur as the adjustor 2470 is rotated a second, opposite direction. The wedge 2490 can be advanced to a more distal location along the longitudinal axis A of the device such that the loops of the sectioning elements 2416 will splay later in the expansion stroke resulting in a larger open area 2446 at the time of splay. The slider sled 2472 can additionally include an expansion stop 2498 configured to abut the wedge 2490 thereby preventing further relative sliding movement between the sled 2472 and the wedge 2490 (see FIG. 26K). Thus, the position of the wedge 2490 can ultimately limit the total expansion achieved because it is incapable of moving beyond the expansion stop 2498.

As described above, one or more retractable sleeves 2415 (see FIG. 24E) can be incorporated that maintain the sectioning elements 2416 in a constrained configuration such that they do not splay away from the longitudinal axis of the device before a user desires splay to occur. A retractable sleeve 2415 may be rigidly coupled to each sectioning element 2416 as discussed elsewhere herein and aid in the longitudinal and rotational motion of the elements 2416. The retractable sleeve 2415 in this way prevents the multiple wires from creating unnecessary drag on the lens during positioning. The retractable sleeve 2415 can be used in conjunction with a separate spreading element (e.g. the wedge 2490) to provide adjustability of the degree of splay, as described in more detail above. Alternatively, the retractable sleeve 2415 can be used in conjunction with a plurality of sectioning elements 2416 that are pre-shaped to splay upon withdrawal of the sleeve 2415 and release of the constraining force. In this implementation, no separate spreading element (e.g. the wedge 2490) is incorporated. Each of the plurality of sectioning elements 2416 can be pre-shaped into the third, splayed configuration. During expansion of the loops towards the second, expanded configuration, the sleeve 2415 can be positioned in a distally extended position in order to keep the plurality of sectioning elements 2416 constrained toward the longitudinal axis A of the device. The sleeve 2415 can then be retracted to allow the plurality of sectioning elements 2416 to automatically splay towards their unbiased splayed configuration.

Figure 33A:
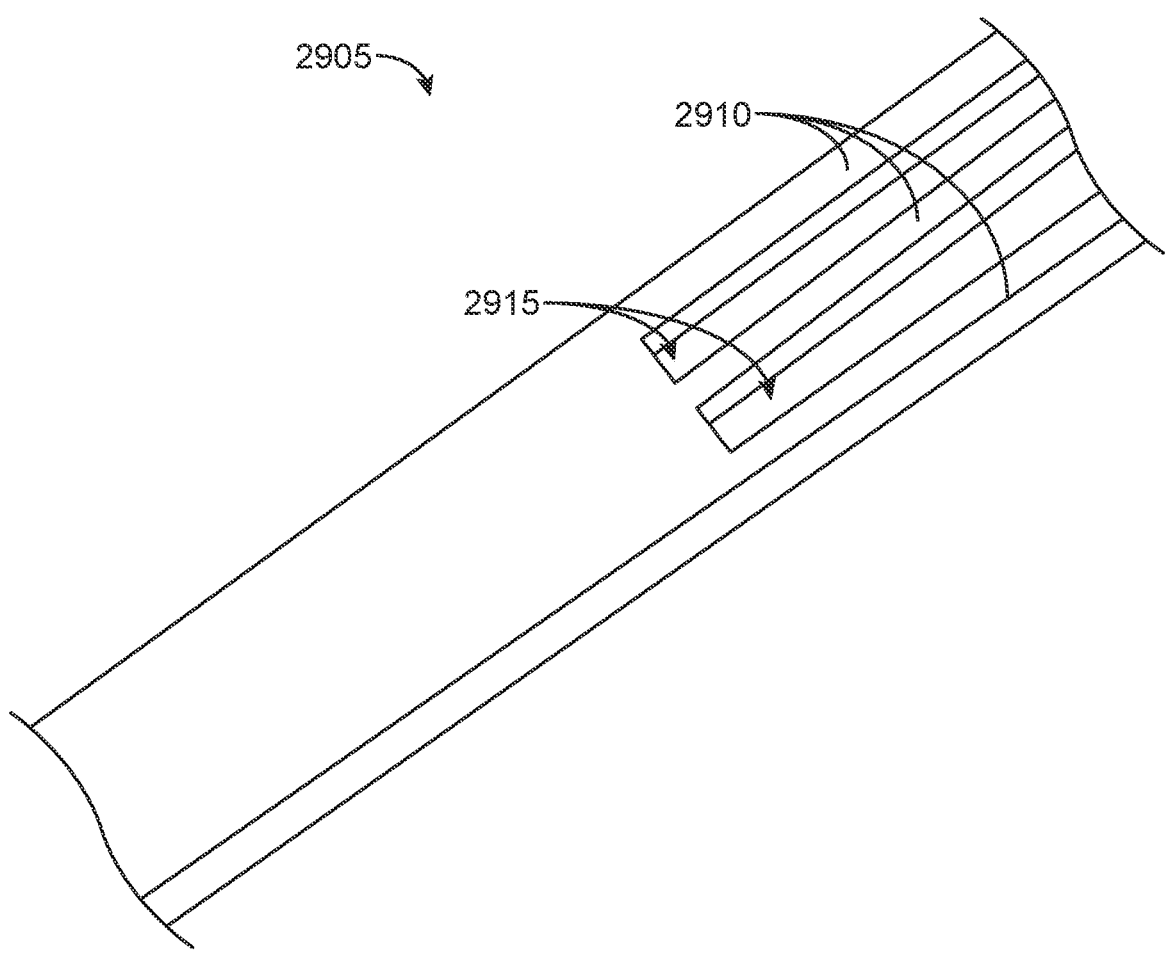
FIGS. 33A-33C illustrate implementations of sectioning elements formed of a long, narrow band of material.
Figure 33B:
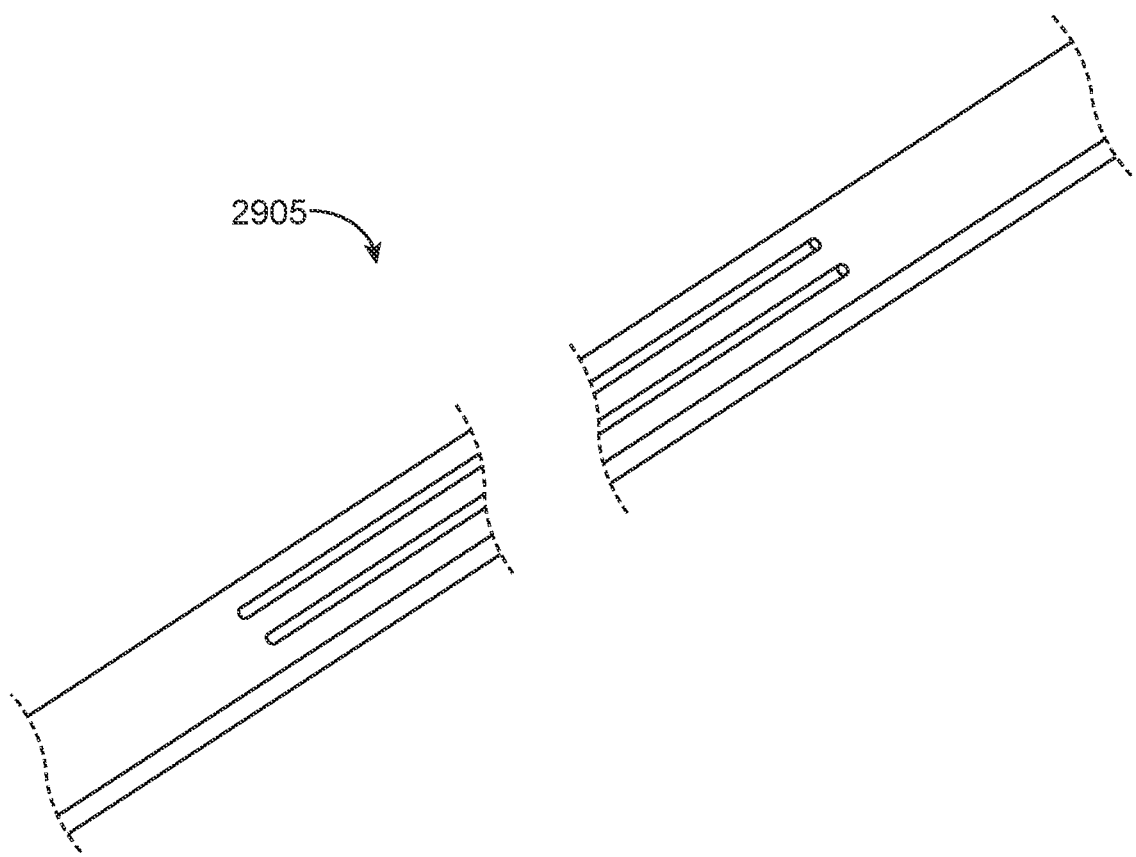
Figure 33C:
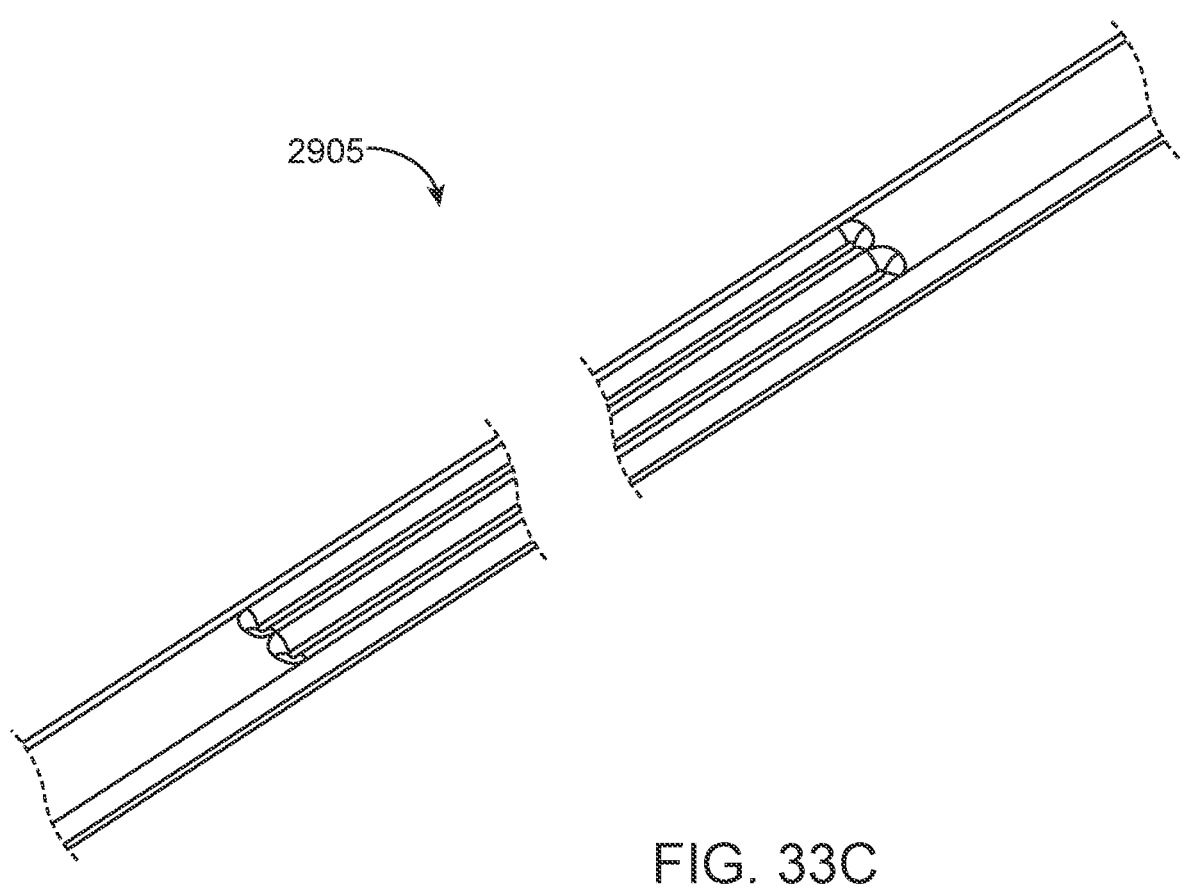

As described elsewhere herein, the sectioning elements 2416 can be a wire having a round or oval cross-section. For example, the device can include a plurality of sectioning elements 2416 formed of three discrete wires (e.g. 0.006" Nitinol wire). The sectioning elements 2416 also can be a strap or long, narrow sheet of material. For example, the device can include a plurality of sectioning elements 2416 formed from a band 2905 of material (see FIGS. 33A-33C). In an implementation as shown in FIG. 33A, the distal end region of the band 2905 can have the plurality of struts 2910 formed into it, each of which are shaped to form a cutting loop when unconstrained, as described elsewhere herein. The proximal end region of the band 2905 can remain as a singular band of material. In another implementation as shown in FIGS. 33B-33C, the plurality of struts 2910 can be formed into a middle region of the band 2905 such that both the proximal end region and the distal end region are flat, contiguous bands of material interspersed by the struts 2810 extend therebetween. The band of material mitigates the discrete wires tangling during deployment movements. The band 2905 can be formed of Nitinol or other biocompatible material capable of shape memory. The implementation of FIGS. 33A-33C, the band 2905 has two cuts 2915 creating three struts 2910. The band 2905 have a thickness of about 0.006" and can be about 0.022" wide. The band 2905 can be laser cut to form the two cuts 2915 resulting in the three struts 2910. The two cuts 2915 can be about 0.002" leaving three struts 2910 that are each about 0.006" wide. The three struts 2910 can then be electro polished to remove corners reshaping the struts 2910 into the plurality of sectioning elements 2416. The cutting and electro polishing can transform the 0.006"×0.006" struts 2910 into 0.006" sectioning elements 2416 that approximate a 0.006" diameter Nitinol wire. It should be appreciated that the number of struts 2910 created can vary as can their dimensions depending on the number of sectioning elements 2416 ultimately desired for the device. For example, the width of the band 2905 can depend on the number of sectioning elements 2416 to be formed. In some implementations, the band 2905 can be formed into two, three, four, or more struts 2910. It should also be appreciated that the width and thickness of the band 2905 can, but need not be uniform and can vary over its length.

Again with respect to FIGS. 25A-25C and also FIGS. 26A-26D, once the sectioning elements 2416 have been extended to the second, expanded configuration (which as described above can be a fully expanded maximum open space dimension or a dimension that is less than maximum), rotated and/or splayed to the third, splayed configuration within the capsular bag 6 in which the sectioning elements 2416 surround at least a portion of the lens 8, the sectioning elements 2416 are then used to cut the lens 8 by tensioning the movable ends 2420 of the sectioning elements 2416. The ends 2420 can be retracted through the lumen of the shaft 2412 in the opposite manner as set forth above for expanding the sectioning elements 2416 from the second, expanded configuration back toward the first configuration in order to compress and cut the lens 8. As the sectioning elements 2416 are tensioned, they exert an inward force on the lens 8 and begin cutting and/or fragmenting it due to the force applied to the lens 8 across the small surface are of the thin diameter sectioning elements 2416. The tensioning may be provided by movement of the slider 2444 proximally, thereby pulling the movable ends of each sectioning element 2416 proximally and tensioning it. Tensioning may also be provided at least in part by the user providing additional force as described elsewhere herein.

Figure 25A:
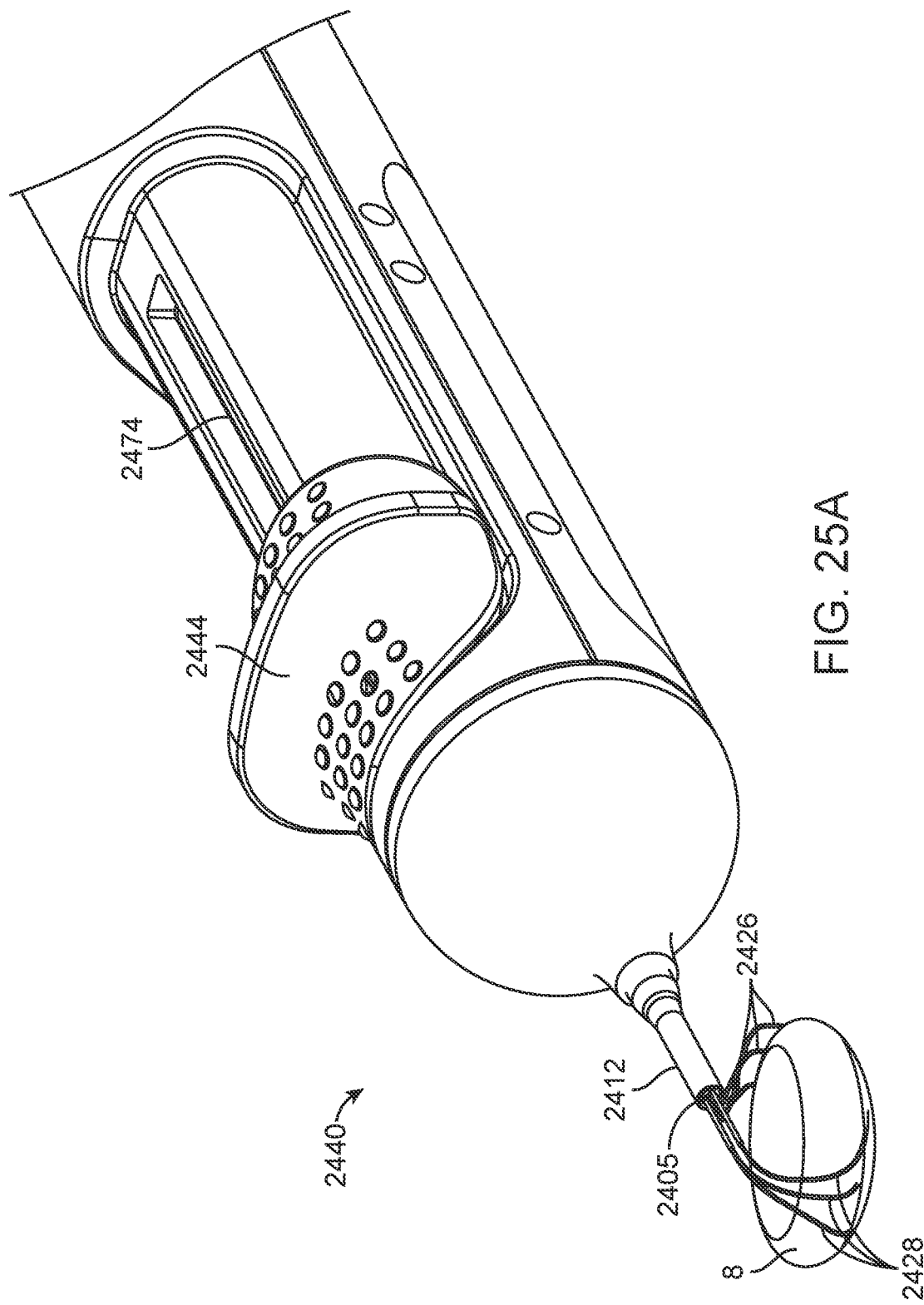
FIG. 25A is a perspective, detail view of the device of FIG. 24A surrounding a lens.
Figure 25B:
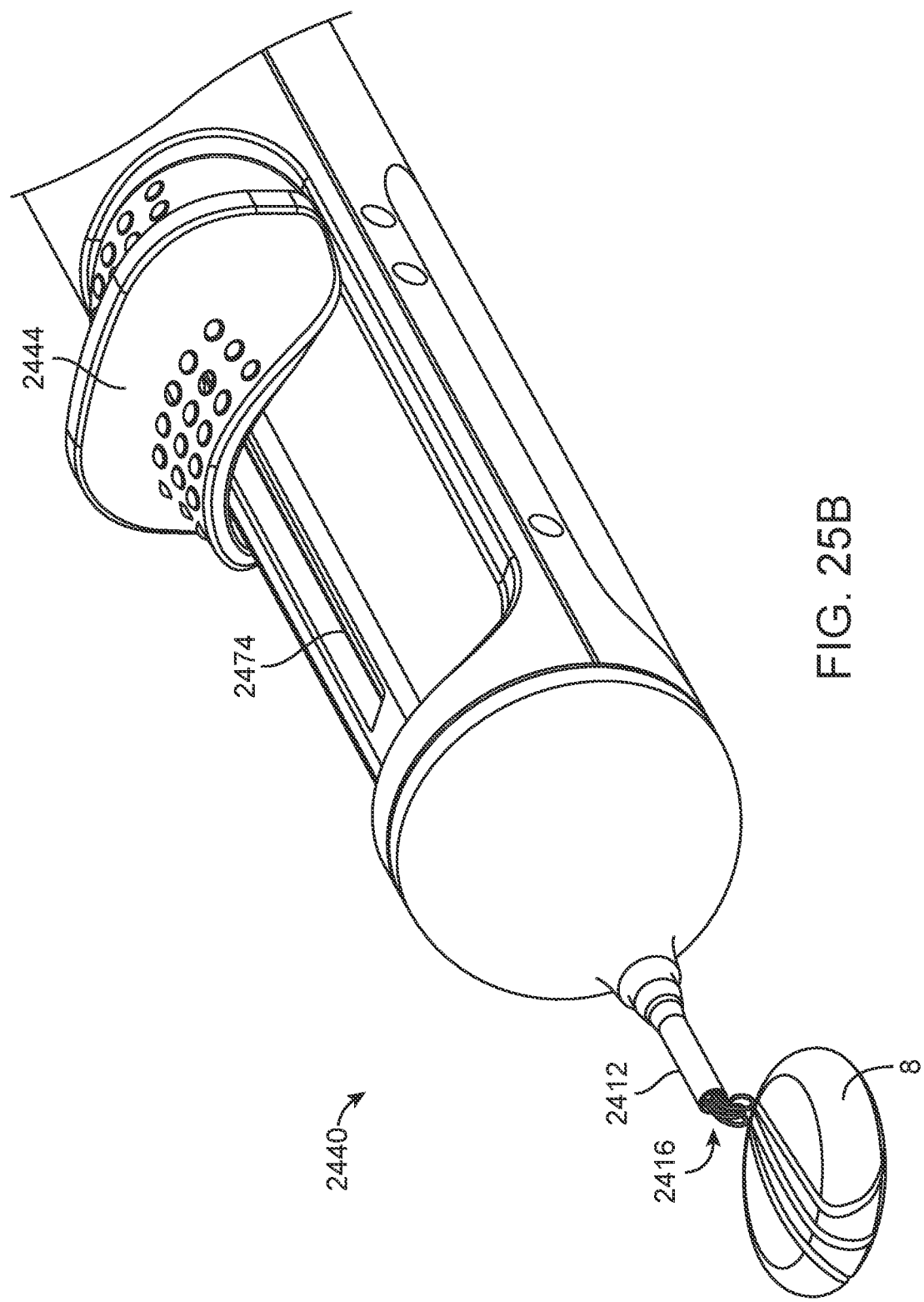
FIGS. 25B-25C are perspective, detail views of the device of FIG. 25A after tensioning and cutting through the lens.
Figure 25C:
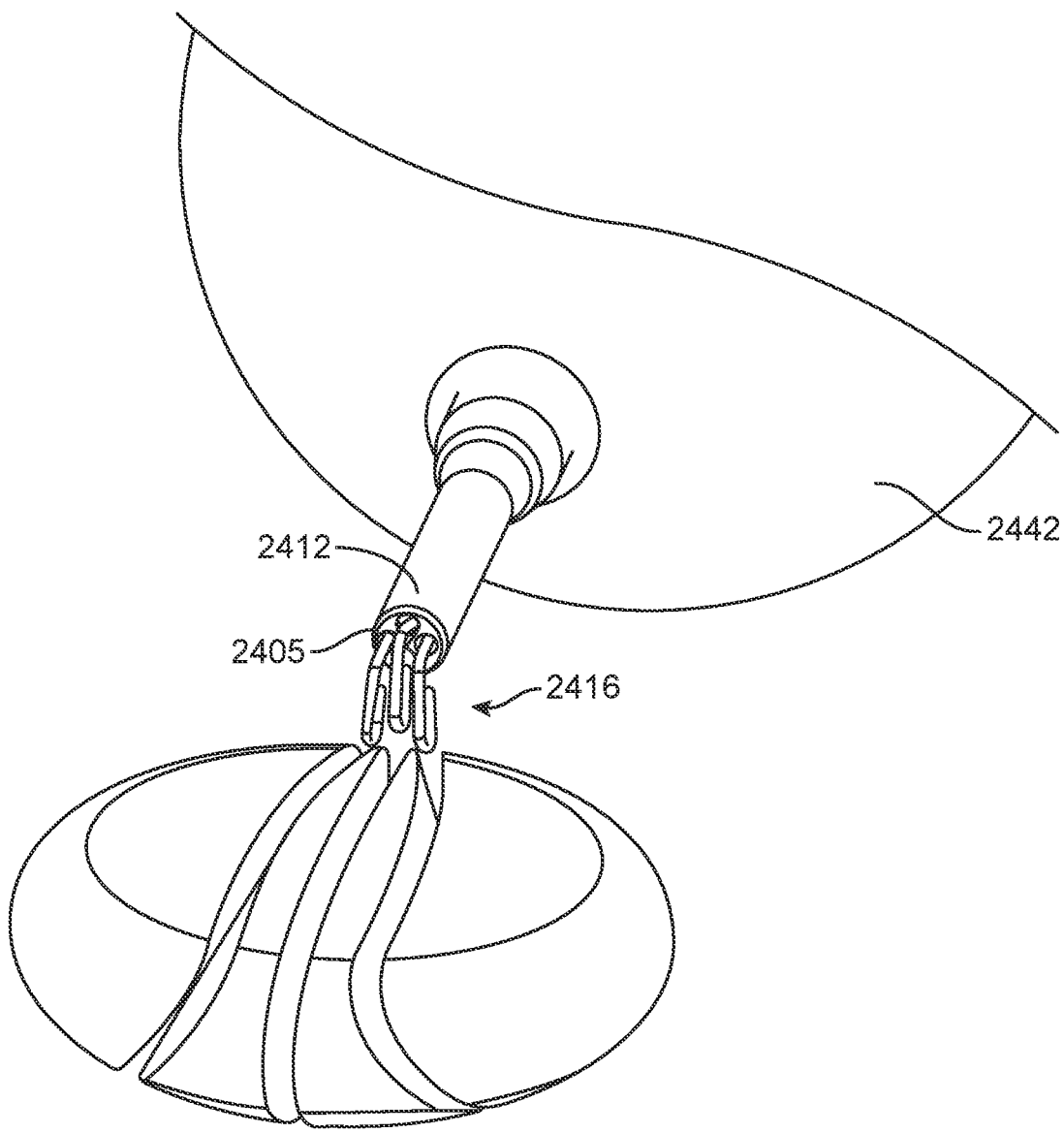

With a single tensioning procedure, the lens 8 can be divided into two, three, or more fragments depending on the number of sectioning elements 2416 incorporated. The process can be repeated along a different rotational angle (i.e. 90 degrees to create a crisscross pattern relative to the first fragmentation) and expansion and tensioning performed again to fragment the lens 8 into even smaller fragments (e.g. four, six, or more). The section plane is shown in FIG. 25C as primarily vertical, but it should be appreciated that any number of angles and orientations may exist for the cutting path of the sectioning elements 2416. The process may be repeated for as many times as necessary to create any number of lens fragments of any desired size. The final desired size of the lens fragments may depend on method of extraction from the eye 1. In some embodiments, phacoemulsification additionally may be used in the capsular bag 6 to remove the lens fragments. This may be particularly useful in difficult or hard cataracts, where full lens fragmentation increases the surface area and decreases the size of fragments that are to be emulsified by phacoemulsification. In other embodiments, the lens fragments may be extracted as described herein. In some embodiments, the lens fragments by be extracted as described in U.S. Publication No. 2018/0318132, entitled "Devices and Methods for Ocular Surgery," published Nov. 8, 2018, which is incorporated by reference herein.

Upon proximal movement of the slider 2444, the sled can be returned to the original position for safe removal of the sectioning elements 2416 from the eye. The sectioning elements 2416 can be rotated back to their original plane of insertion, and then retracted into the shaft 2412. When the slider 2444 is fully withdrawn in a proximal direction, the sectioning elements 2416 can be placed in an over-strained position that over time can be detrimental to the shape memory properties of the sectioning elements 2416. The device can include a spring 2458 that, when the loops of the sectioning elements 2416 are retracted back into the lumen of the shaft 2412, causes the loops to not be retracted to such a small size that the shape memory of the Nitinol is affected. For example, a spring 2458 (see FIG. 24D) can be placed over a proximally-facing nose 2456 and extend proximally from the sled 2472 such that the slider 2444 and sled 2472 are urged into a slightly more distal position relative to the housing 2442 upon release of the slider 2444 (see FIG. 26A-26B). If the user retracts the sectioning elements 2416 too far using the slider 2444, the spring 2458 can urge the sled 2472 a short distance in the distal direction after the slider 2444 is released by the user. This allows the loops of the sectioning elements 2416 to extend slightly out the distal end 2405 of the shaft 2412 and maintain a slightly enlarged open area 2446 when in a resting state compared to the fully retracted state (see FIG. 24A). The size of the distal end 2405 of the shaft 2412 and the slightly enlarged open areas 2446 positioned outside the distal end 2405 of the shaft 2412 may be small enough to be inserted through a clear corneal incision (i.e. maximum outer diameter being less than about 3.5 mm) such that the distal loops of the sectioning elements 2416 need not ever be fully retracted inside the lumen of the shaft 2412 in order to be inserted into the anterior chamber of the eye.

Slider actuation can be restricted such that the device is prevented from being used more than for a single medical procedure. For example, one-way latches, levers, ratchets, pawls, racks, and other mechanical elements can be incorporated within the housing to engage with the slider preventing extension of the cutting element via distal movements of the slider and sled attached to the slider. The stroke counting mechanisms described herein may limit the device to being a single-use device or limited-use device. "Single-use" or "limited-use" as referred to herein means the devices described herein are intended to be used in a single patient and not intended to be re-sterilized and used on another patient. The stroke counting mechanisms described herein may provide a low-cost method for limiting the use of the device, which can be manufactured as a low-cost, disposable device. It should be appreciated the stroke counting mechanisms configured to track distal extensions and/or proximal extensions of the slider can be used with a device having any number of sectioning elements, including 1, 2, 3, or more sectioning elements.

Even with a single-use device, it is preferable to allow the slider 2444 (or other extension/retraction mechanism) to be actuated more than a single back-and-forth stroke. For example, a user may want to slide the slider 2444 back and forth a few times to get the feel for the device prior to using it on a patient. In some implementations, the device 2440 can incorporate a stroke counting mechanism that allows for multiple actuations or distal extensions/proximal extensions of the slider (or other input configured to extend and retract the sectioning elements 2416) a discrete number of times prior to preventing extension of the slider 2444, sled 2472 and/or sectioning elements 2416. The stroke counting mechanism thereby may limit the utility of the device after clinical use in a single patient. The stroke counting mechanism can track distal extensions and/or proximal extensions of the slider and cause a lock-out event that prevents further distal extensions of the slider after the lock-out event occurs. It should be appreciated that use of the term "slider" is not intended to be limited and other types of inputs configured to extend/retract the sectioning elements 2416 are considered herein.

Figure 27B:
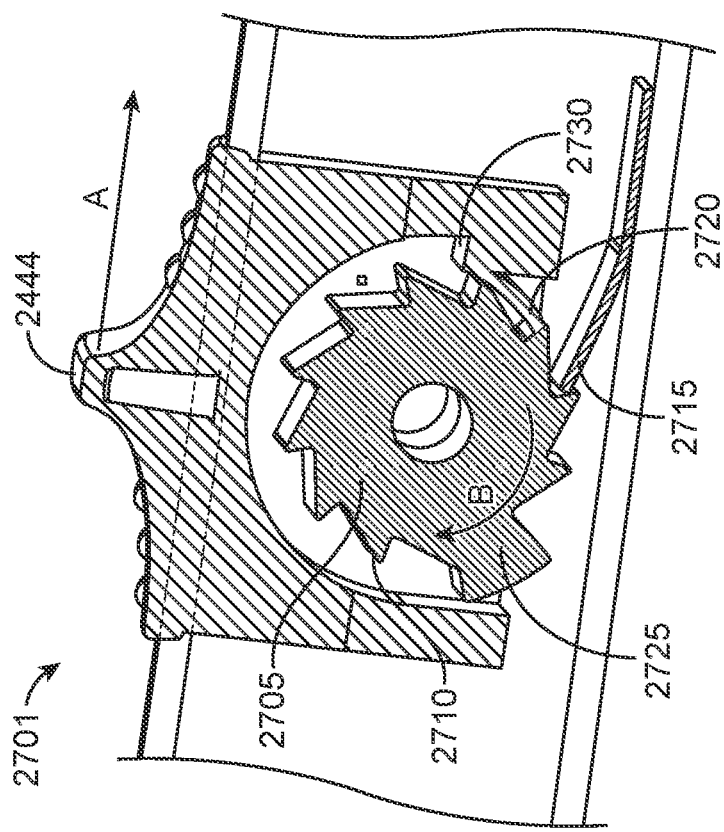
Figure 27A:
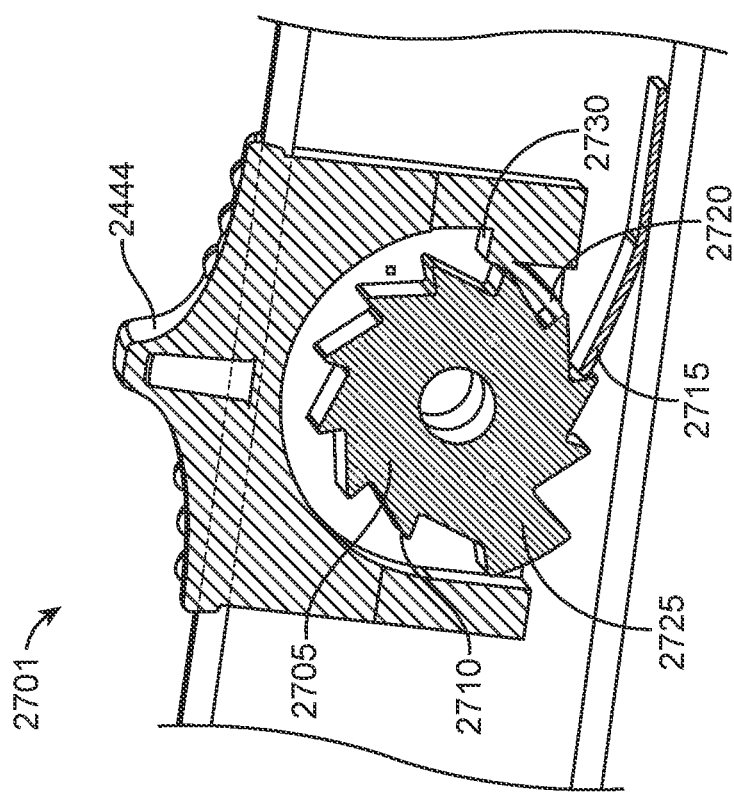

In some implementations, the slider 2444 can be coupled to a stroke counting mechanism 2701. FIGS. 27A-27C shows a stroke counting mechanism 2701 that can incorporate a counting pawl system. A ratchet or cogwheel 2705 positioned within the handle 2442 can have a plurality of teeth 2710 in operable engagement with a main sprag 2715 and a secondary sprag 2720. The main sprag 2715 can be coupled to an inner region of the housing 2442 and the secondary sprag 2720 can be coupled to the slider 2444. During forward movement of the slider 2444 (i.e. towards a distal end of the housing 2442 along the direction of arrow A), a tooth 2710 of the cogwheel 2705 is urged against the main sprag 2715 causing the cogwheel 2705 to rotate forward one tooth 2710 around arrow B. On the backstroke as the slider 2444 is moved towards a proximal end of the housing 2442, the secondary sprag 2720 prevents the cogwheel 2705 from back-driving in the opposite direction as the teeth 2710 slide back over the main sprag 2715. The cogwheel 2705 also includes a stop tooth 2725 configured to lock against a stop 2730. After the cogwheel 2705 has been advanced through a number of strokes, which can be defined by the number of teeth 2710 on the cogwheel 2705, the stop tooth 2725 locks against the stop 2730 preventing further turning of the cogwheel 2705 in either direction (see FIG. 27C). This prevents the slider 2444 from entering the distal end of its travel and thereby prevents the sectioning elements 2416 from being fully expanded. Movement of the sectioning elements 2416 is prevented by the lockout rendering the device 2440 unusable after a certain number of extensions. The number of teeth 2710 can vary, including 2, 3, 4, 5, 6, 7, 8, 9, 10, or more teeth. After lockout, the slider 2444 is still able to move freely in the proximal portion of its travel, allowing further constriction of the distal loop and safe removal of the sectioning elements 2416 from the eye. The main sprag 2715 can be formed of sheet metal material having a shape that will bend upwards if a user attempts to over-power the main sprag 2715 by urging the slider forward. Similarly, the secondary sprag 2720 can be formed of a sheet metal material. Alternatively, one or both of the sprags 2715, 2720 can be formed by a flexible piece of molded plastic that can be deflected out of the way when the cogwheel 2705 spins in a direction B, but will not move out of the way when the cogwheel 2705 spins in the opposite direction.

The stroke counting mechanisms described herein can be configured to count the number of distal extensions, proximal extensions (i.e. retractions), or both the distal extensions and proximal extensions of the slider. The stroke counting mechanisms described herein can prevent distal extensions after a certain number of actuations of the slider have been performed. Generally, the stroke counting mechanisms described herein do not prevent proximal movement of the slider such that the device is prevented from being stuck in an extended configuration with the expanded loops trapped outside of the shaft.

Figure 28A:
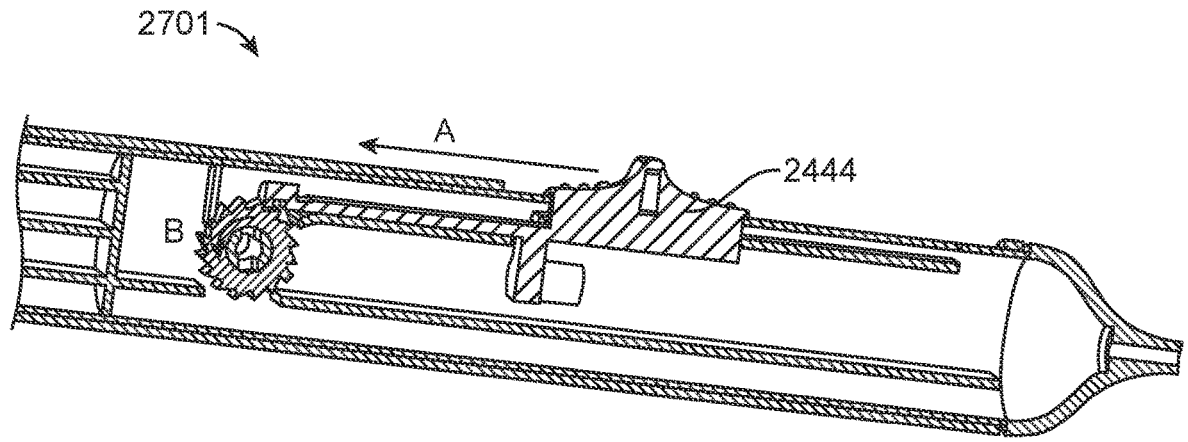
FIGS. 28A-28B illustrate another implementation of a stroke counting mechanism.
Figure 28B:
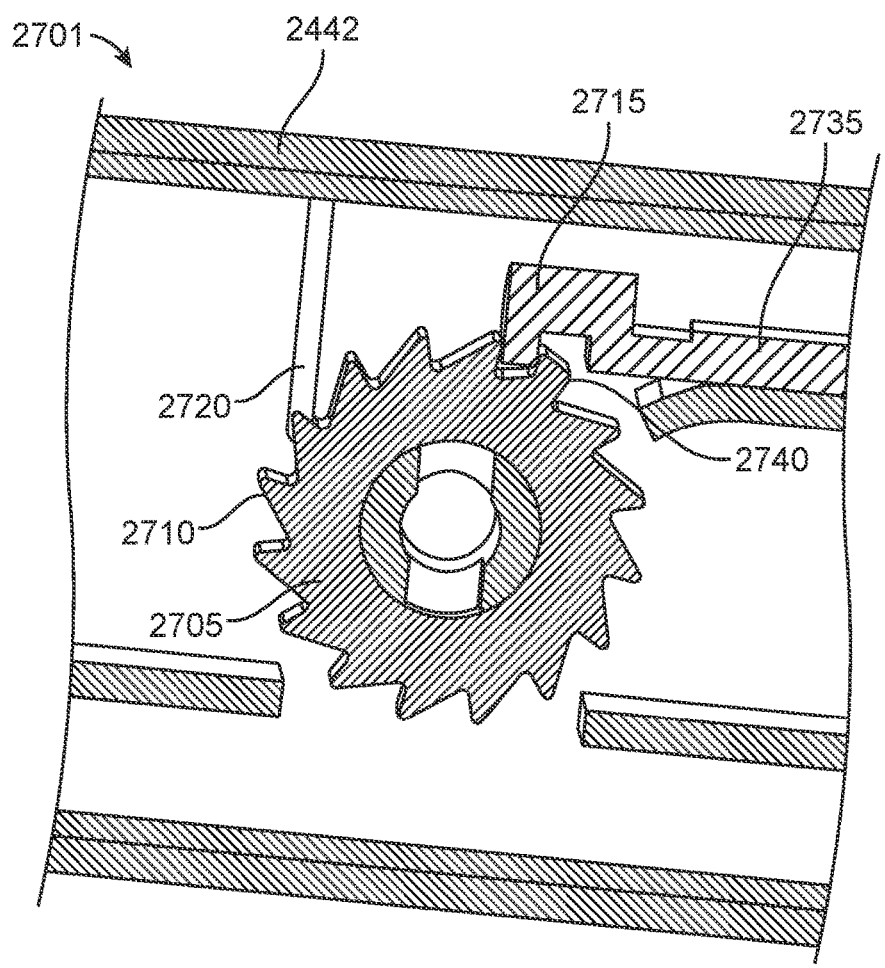

The configuration of the stroke counting mechanism can vary. FIGS. 28A-28B illustrate another implementation of a stroke counting mechanism 2701. The stroke counting mechanism 2701 can incorporate a counting pawl system. A cogwheel 2705 positioned within the handle or housing 2442 can have a plurality of teeth 2710 in operable engagement with a main sprag 2715 and a secondary sprag 2720. In this implementation, the cogwheel 2705 can be attached to the device housing 2442 such that it remains stationary along the longitudinal axis of the device during movement of the slider 2444. The slider 2444 can have a proximally-extending arm 2735 having the main sprag 2715 on its proximal end. In contrast to the implementation of FIGS. 27A-27C in which the cogwheel 2705 is advanced during each forward stroke of the slider 2444, the cogwheel 2705 in this implementation is advanced one tooth 2710 at a proximal end of each backstroke of the slider 2444 (arrow A of FIG. 28A). The main sprag 2715 on the proximal-extending arm 2735 engages with a tooth 2710 of the cogwheel 2705 and rotates the cogwheel 2705 in a backward direction one tooth 2710 (arrow B of FIG. 28A). The cogwheel 2705 is prevented from rotating in the opposite direction due to the presence of the secondary sprag 2720 engaging with a tooth 2710 on the cogwheel 2705. The secondary sprag 2720 can be positioned on an interior of the housing 2442. After the cogwheel 2705 has been advanced through a discrete number of strokes defined by the number of teeth 2710 on the cogwheel 2705, a catch tooth 2740 becomes entrapped with the main sprag 2715 on the arm 2730, which in turn cannot be advanced forward because the cogwheel 2705 is prevented from rotating in the forward direction due to the secondary sprag 2720 (see FIG. 28B). This locks the slider 2444 in the proximal-most position and the sectioning elements 2416 in their most constricted shape. The counting pawl system can have any of a variety of configurations that allow for a limited number of retraction/extension cycles of the slider before mechanical locking occurs.

Figure 29A:
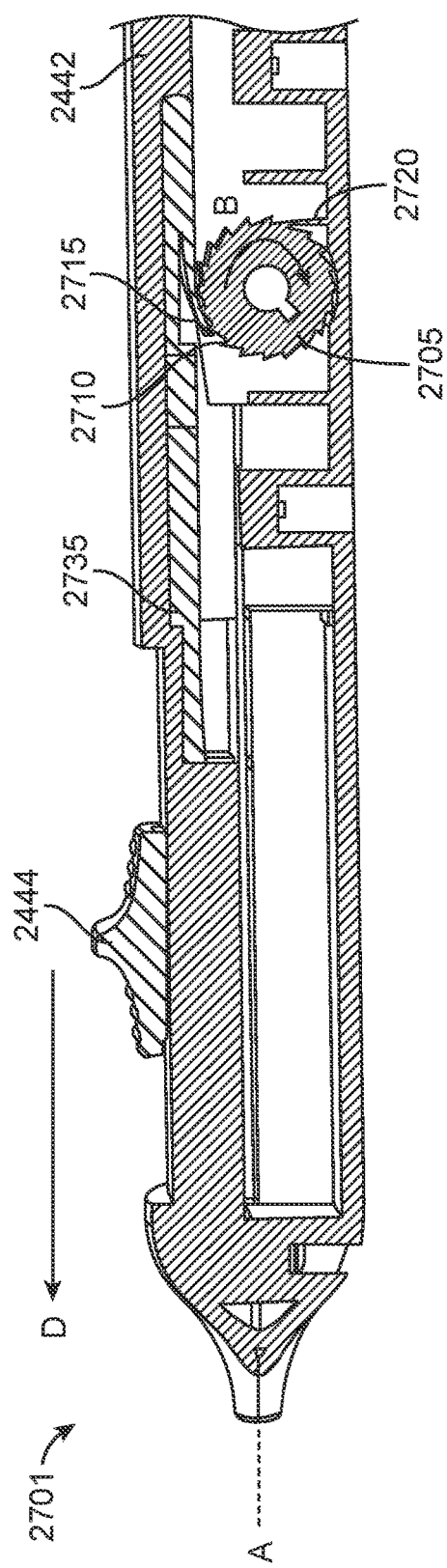
FIGS. 29A-29B illustrate another implementation of a stroke counting mechanism.
Figure 29B:
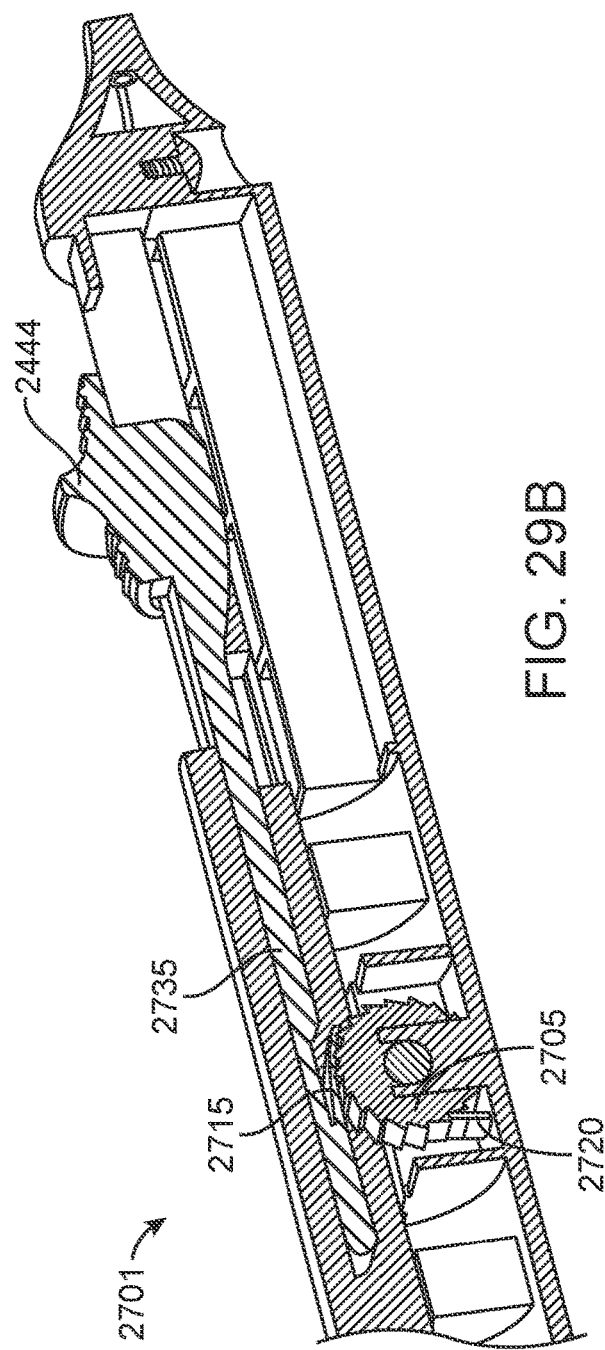
Figure 30C:
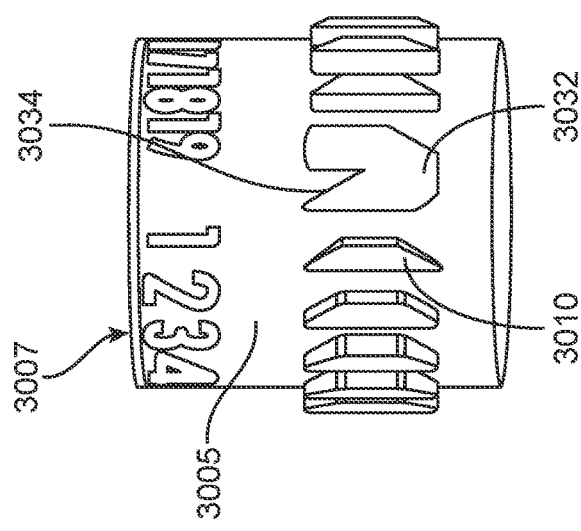
Figure 30D:
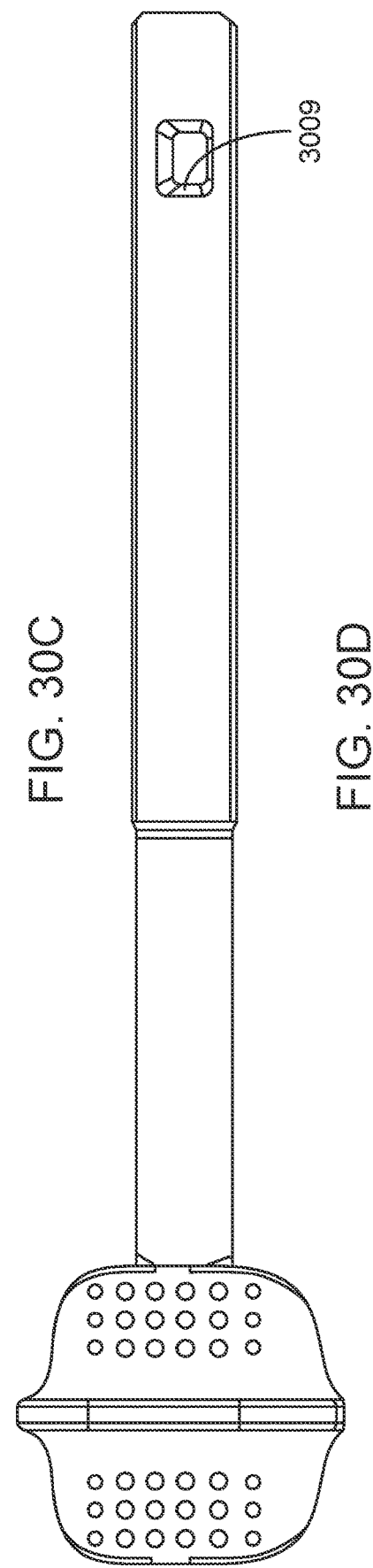
Figure 30E:
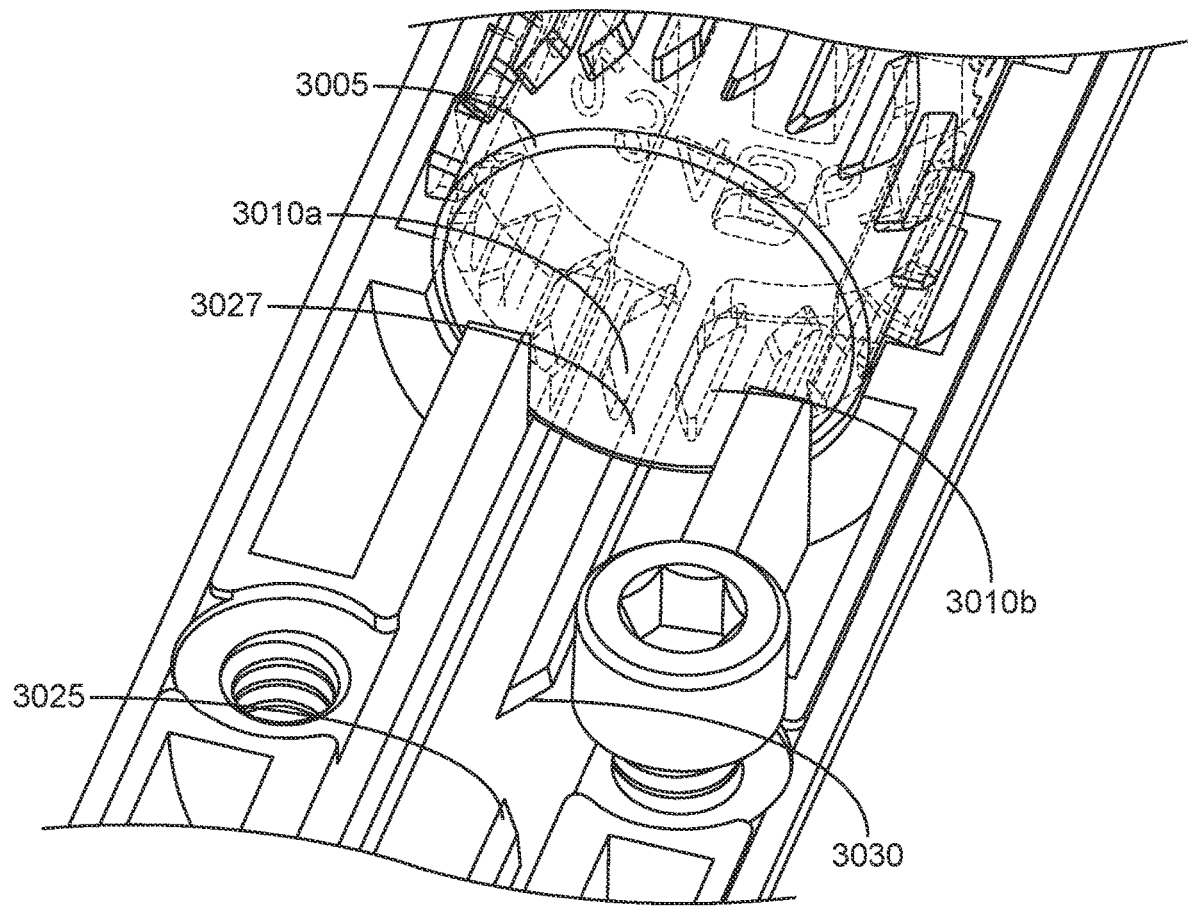

FIGS. 29A-29B illustrate another configuration of a stroke counting mechanism 2701. As with implementations described above, a cogwheel 2705 is positioned within the handle having a plurality of teeth 2710 in operable engagement with a main sprag 2715 and a secondary sprag 2720. The cogwheel 2705 can be attached to an interior of the device housing 2442 and configured to rotate around an axis arranged perpendicular to the longitudinal axis of the housing 2442 extending from distal end to proximal end. The cogwheel 2705 is fixed along the longitudinal axis such that as the slider 2444 extends and retracts axially along the longitudinal axis of the housing 2442, it engages with the teeth 2710 of the cogwheel 2705. The slider 2444 can have a proximally-extending arm 2735 having the main sprag 2715 on its proximal end region. The main sprag 2715 extends from the proximal end region of the arm 2735 such that an end of the main sprag 2715 faces towards a distal end of the housing 2442. The teeth 2710 of the cogwheel 2705 project towards a proximal end of the housing 2442. This relative arrangement of the main sprag 2715 and the teeth 2710 allows for the cogwheel 2705 to be advanced during each forward stroke of the slider 2444 (i.e. towards a distal end of the housing 2442) and to remain stationary during each backward stroke of the slider 2444 (i.e. towards the proximal end of the housing 2442) as the main sprag 2715 passes over the teeth 2710 of the cogwheel 2705. During forward movement of the slider 2444, a tooth 2710 of the cogwheel 2705 is urged against the main sprag 2715 causing the cogwheel 2705 to rotate forward one tooth 2710 around arrow B. On the backward stroke as the slider 2444 is moved towards the proximal end of the housing 2442, the secondary sprag 2720 prevents the cogwheel 2705 from back-driving in the opposite direction as the teeth 2710 slide back over the main sprag 2715. The cogwheel 2705 can also include a stop tooth (like 2725 shown in FIG. 27A-27C) configured to lock against a stop as described elsewhere herein.

The implementations of the counting mechanisms described above involve rotation of a cogwheel around an axis that is perpendicular to the longitudinal axis A of the housing 2442. The counting mechanism 2701 can also include an element configured to rotate around the longitudinal axis A of the housing 2442. FIGS. 30A-30D illustrate another implementation of a stroke counting mechanism 2701 including a cylindrical counting barrel 3005 positioned within the housing 2442 such that a central axis of the barrel 3005 is aligned coaxially with the longitudinal axis A of the housing 2442. The counting barrel 3005 can include a plurality of ramp blocks 3010 projecting upward from and arranged radially around its outer surface. An underneath side of the slider 2444 can have a first slider ramp 3025 and a second slider ramp 3030 (see FIG. 30D) shaped and arranged to engage with the ramp blocks 3010 upon retraction and extension of the slider 2444, respectively. The shape of each ramp block 3010 and the shape of the slider ramps 3025, 3030 can vary, but are generally complementary to one another. A complementary shape of the ramp blocks 3010 and the slider ramps 3025, 3030 allows the slider ramps 3025, 3030 to abut and slide past the ramp blocks 3010. The axial movement of the ramps 3025, 3030 along the longitudinal axis A results in rotary motion of the barrel 3005 in a direction around arrow B due to interaction with the ramp blocks 3010 (see FIG. 30A). Each distal extension of the slider can turn the cylindrical counting barrel a fraction of a full revolution of the barrel as will be described in more detail below. The barrel is configured to turn up to a certain number of fractions before the lock-out event occurs. The lock-out event can prevent distal extensions of the slider while allowing proximal retraction of the slider to avoid locking the slider when the cutting element is in the expanded configuration within a patient's eye.

In some implementations, the ramp blocks 3010 can have a polygonal shape with at least two ramped surfaces relative to the longitudinal axis of the barrel 3005, including a front ramp 3015 configured to engage with a complementary ramped surface on the first slider ramp 3025 and a back ramp 3020 configured to engagement with a complementary ramped surface of the second slider ramp 3030. In some implementations, the front ramp 3015 faces towards the distal end of the housing 2442 and the back ramp 3020 faces towards the proximal end of the housing 2442. As such, the first slider ramp 3025 configured to engage with the front ramp 3015 faces towards the proximal end of the housing 2442 and the second slider ramp 3025 configured to engage with the back ramp 3020 faces towards the distal end of the housing 2442 (see FIG. 30B). On the backward stroke (i.e. towards a proximal end of the housing 2442), the first slider ramp 3025 abuts the front ramp 3015 of a first ramp block 3010a of the barrel 3005. The barrel 3005, in turn, is rotated around the longitudinal axis A of the device in a first direction around arrow B. The barrel 3005 rotates a fraction of a complete revolution of the barrel 3005. After the barrel 3005 has completed its fraction of a rotation and the slider 2444 continues to move backwards, the barrel 3005 is prevented from rotating by an extension 3027 of the second slider ramp 3030 (see FIG. 30E). The extension 3027 is positioned between two of the ramp blocks 3010a, 3010b on the barrel 3005 such that the barrel 3005 is prevented from rotating even, for example, if the device is shaken or dropped. The slider 2444 can prevent the barrel 3005 from rotating when the slider ramps are not aligned with the ramp blocks 3010 on the barrel 3005. On the forward stroke of the slider 2444, the second slider ramp 3030 abuts the back ramp 3020 of the next ramp block 3010b and rotates the barrel 3005 around the longitudinal axis A of the housing 2442 another fraction of a complete revolution of the barrel 3005 around arrow B. For example, the barrel 3005 can rotate ¹⁄₂₄ of a complete revolution on the backward stroke and another ¹⁄₂₄ of a complete revolution on the forward stroke. Thus, for every forward and backward cycle of the slider 2444, the barrel 3005 can rotate ¹⁄₁₂ of a complete revolution.

The number of ramp blocks 3010 can vary depending on how many cycles of actuation of the slider 2444 is desired (e.g. 3, 4, 5, 6, up to about 19, 20, or more). The slider can extend distally about 3 to about 30 strokes before the lock-out event occurs and the slider is locked in the rearward position. Each barrel 3005 can additionally include a stop block 3032 (see FIG. 30C). The stop block 3032 can be positioned on the outer surface of the barrel 3005 after than last ramp block 3010. The stop block 3032 may include a front ramp 3015. However, the stop block 3032 may have no back ramp 3020. Instead, the stop block 3032 may include a groove 3034 arranged to prevent forward or distal translation of the slider 2444 (see FIG. 30C). The stop block 3032 can limit the barrel 3005 to a certain number of turns. The stop block 3032 can be positioned such that it engages with the slider ramps when the slider 2444 is moving forward or when the slider 2444 is moving backward.

The position of the slider 2444 when it engages with the stop block 3032 can be anywhere along its range of motion. For example, the slider 2444 can engage with the stop block 3032 when the slider 2444 is in the most forward position, the most backward position, or at any point between the two. In some implementations, the slider 2444 engages with the stop block 3032 about mid-way through its range of motion on a forward stroke. There are several potential advantages to this configuration related to the shape of the sectioning element 2416 at the front of the device. For example, the sectioning element 2416 is able to be transitioned into its smallest configuration even if the stroke counting mechanism has reached its limit and a lock-out event has occurred. This is useful so that the device can always be removed from the eye through the corneal incision by retracting the slider fully.

Figure 31A:
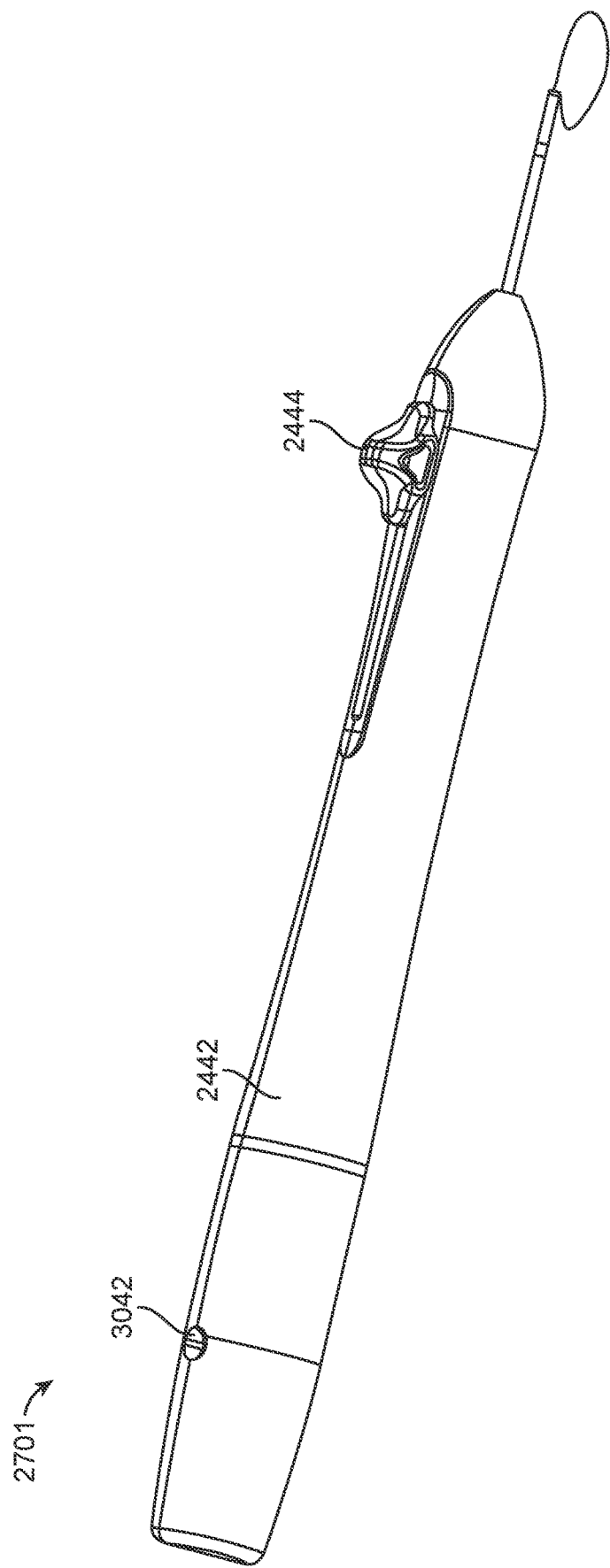
FIG. 31A is perspective view of another implementation of a device including a stroke counting mechanism.
Figure 31B:
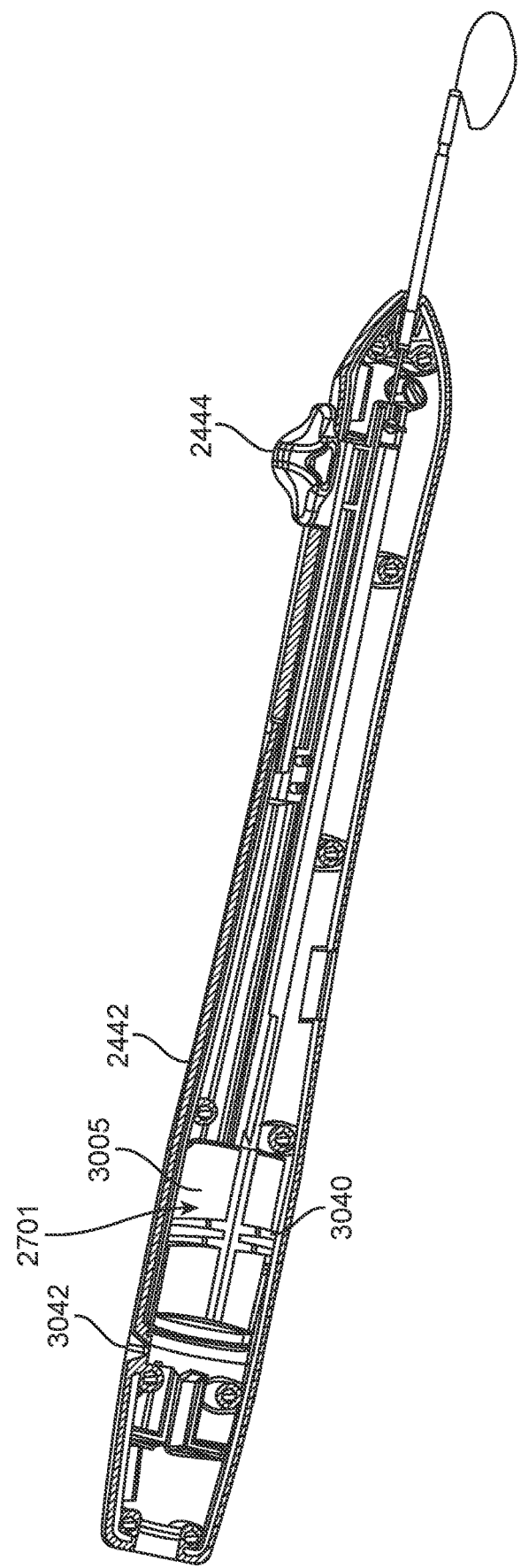
FIG. 31B is a partial cut-away view of the device of FIG. 31A.
Figure 31E:
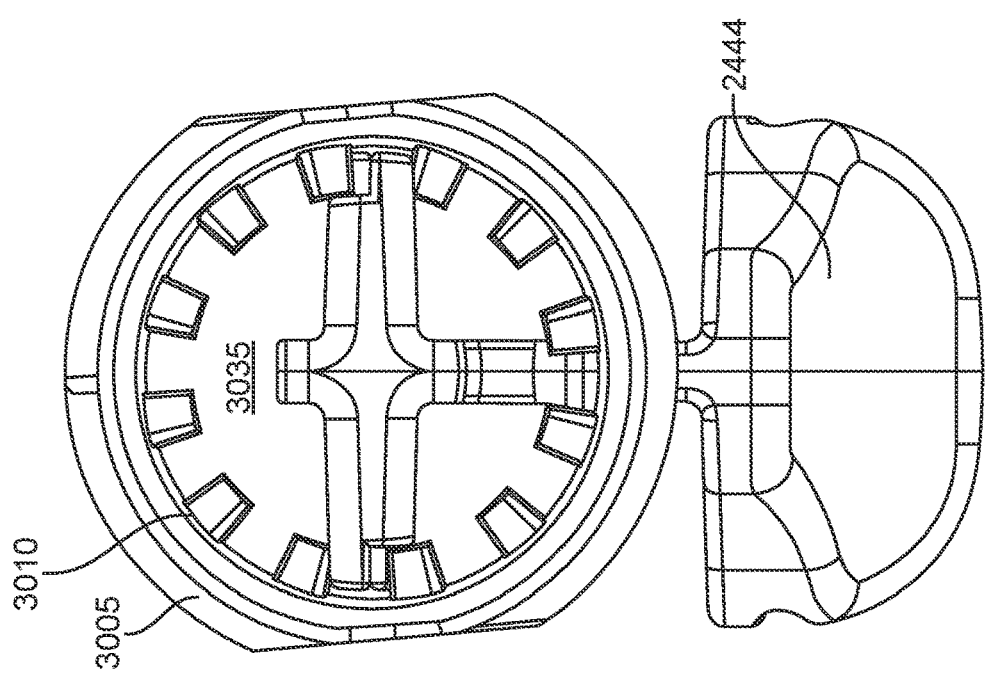
FIG. 31E illustrates the counter barrel of FIG. 31C relative to the slider.
Figure 31C:
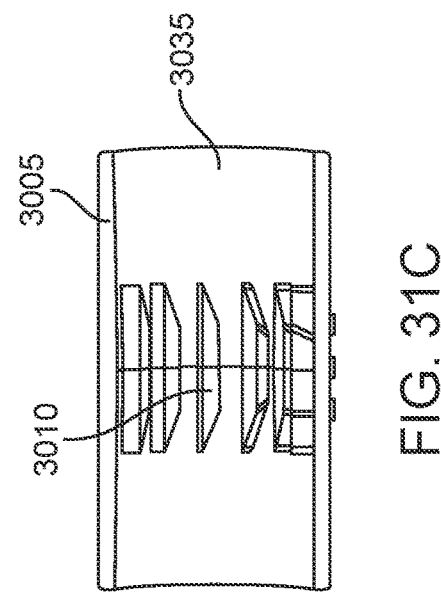
FIG. 31C is an implementation of a counter barrel.
Figure 31D:
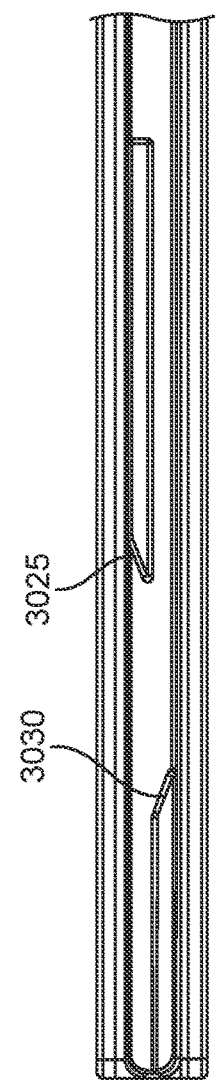
FIG. 31D illustrates slider ramps configured to engage with the counter barrel of FIG. 31C.

In some implementations, the counting barrel 3005 includes a plurality of ramp blocks 3010 within an internal passage 3035 (shown in FIGS. 31C and 31E). The plurality of ramp blocks 3010 may be arranged radially around the inner surface of the internal passage 3035. As with the implementation described above, each ramp block 3010 can include a front ramp 3015 and a back ramp 3020 configured to be placed in operable engagement with a first slider ramp 3025 and a second slider ramp 3030 upon retraction and extension of the slider 2444. In this implementation, a proximal end region of the slider 2444 can extend through the internal passage 3035 of the counting barrel 3005 such that the slider ramps 3025, 3030 can come into engagement with the ramp blocks 3010. The outer surface of the barrel 3005 can include a helical thread 3040 (visible in FIG. 31B) configured to engage a corresponding female thread on an inner surface of the housing 2442. As the barrel 3005 turns, the barrel 3005 threads down a length of the housing 2442 in an axial direction. Eventually, the barrel 3005 reaches a hard-stop that prevents the barrel 3005 from moving any further in an axial direction and the device is locked out. Thus, the barrel 3005 can go through multiple revolutions before a lock-out event occurs and it reaches the hard-stop. The hard-stop can include a termination of the female thread on the inner surface of the housing 2442. The helical thread 3040 can limit the barrel 3005 to a certain number of turns, for example, 2.5 turns of travel. The barrel 3005 can rotate through 2.5 turns×12 strokes/turn or a total of 30 strokes before hitting the hard-stop. At the hard-stop, the slider 2444 can get trapped in the rearward part of the travel and the device is prevented from being used again.

Figure 31F:
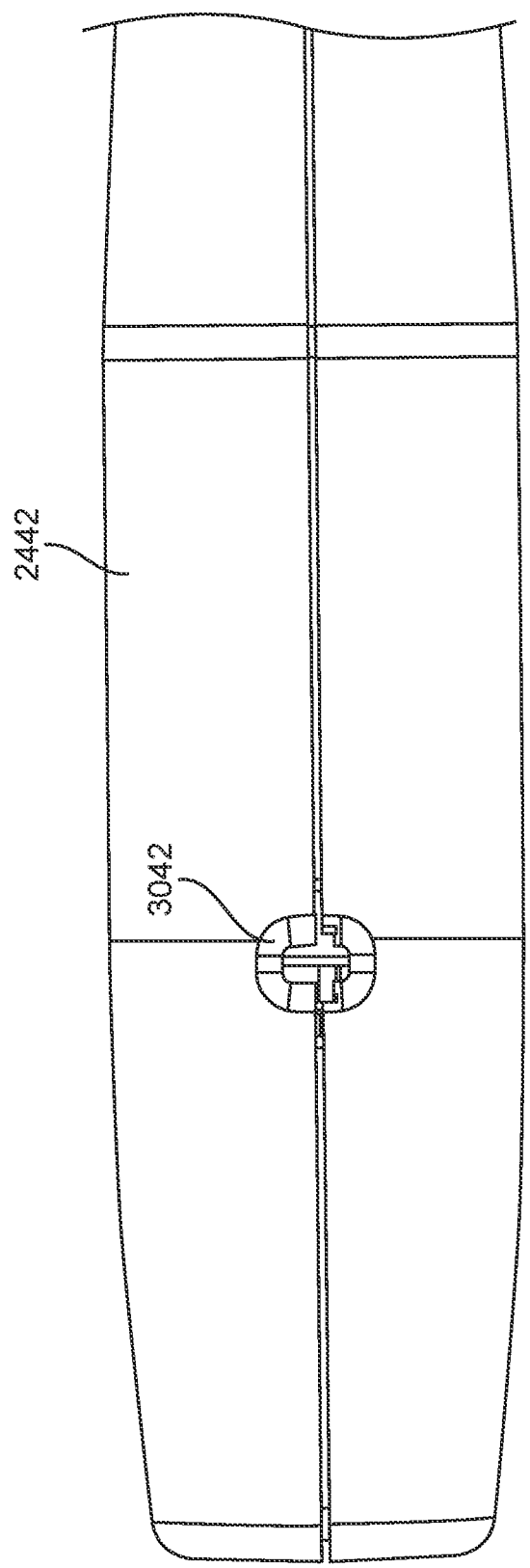
FIG. 31F illustrates an implementation of a lock-out warning for the device of FIG. 31A.

In some implementations, the device can include mechanism to provide a warning before lock-out of actuation occurs (see FIG. 31F). The lock-out warning feature can be mechanical, for example, a window 3042 extending through the housing 2442 providing a visible sign or indication of the position of the barrel 3005 within the housing 2442, for example, relative to the hard-stop. The window 3042 can be arranged near where a user can easily view it during use (e.g. on the top of the device near where a user might be holding the device). The window 3042 allows a user to see a contrasting color as the indexing barrel 3005 translates rearward. When the barrel 3005 is positioned near the window 3042 of the housing 2442, the color of the barrel 3005 may be visible through the window 3042 providing an indication of the number of distal extensions still available before a lock-out event occurs. For example, the outer surface of the barrel 3005 can be viewed through the window 3042 during use. When the barrel 3005 is in a more distal position within the housing 2442 and still has quite a few strokes available, the barrel 3005 can be positioned distal to the window 3042 such that it is not visible through the window 3042 and the window 3042 appears dark or a first color. The barrel 3005 can remain distal to the window 3042 for a number of strokes until the barrel 3005 approaches the stop (e.g. the stop block 3032 or other stop as described elsewhere herein). At this stage when only a few more strokes are available, the outer surface of the barrel 3005 can be visible through the window 3042. The color of the outer surface of the barrel 3005 can be easily identifiable through the window 3042. The barrel 3005 may be a distinct color that is readily identifiable compared to a color of the handle 2442 (e.g. orange or red where the handle 2442 is white or gray) alerting the user to the position of the barrel 3005 before lock-out occurs. Alternatively, the outer surface of the barrel 3005 can be visible through the window 3042 prior to and during use. The outer surface of the barrel 3005 can have at least two contrasting colors that notifies the user where the barrel 3005 is in its travel. For example, a proximal end region of the barrel 3005 can be viewed through the window 3042 prior to use. The outer surface of the proximal end region of the barrel 3005 can be a first color (e.g. black or blue). With each translation cycle of the slider 2444, the barrel 3005 is urged in a proximal direction within the housing 2442 until a distal end region of the outer surface of the barrel 3005 is visible through the window 3042. The outer surface of the distal end region of the barrel 3005 can be a different color (e.g. orange or red). Thus, as the barrel 3005 approaches its stop within the housing 2442, the different color can be visible through the window 3042 alerting the user the barrel 3005 is near the end of its life.

In some implementations, the barrel 3005 has a series of markings 3007 on its outer surface. For example, FIG. 30A-30E shows the barrel 3005 has the numbers '1' through '20' marked on the outer surface. The markings 3007 can line up with the window 3042 in the top housing such that the markings 3007 on the barrel 3005 aligned with the window 3042 are visible to the user. The markings 3007 may be numbers corresponding to the number of cycles remaining, the number of cycles used, etc. such that the user is made aware of the status of the stroke counting mechanism. Further, the slider 2444 may also have a window 3009 along its length (see FIG. 30D). The window 3009 of the slider 2444 may line up with the window 3042 through the top housing 2442 such that the marking(s) 3007 on the barrel 3005 at a particular position of the slider 2444 aligns with the windows 3009, 3042 and is visible to the user. For example, when the slider 2444 is advanced fully distally forward and the sectioning element 2416 of the device is fully open, then the window 3009 of the slider 2444 may line up with the window 3042 of the top housing so that the user can see the corresponding number at this time. As the slider 2444 is retracted proximally, the window 3009 of the slider 2444 moves and the slider 2444 blocks the view of the markings 3007 on the barrel 3005 through the top housing 2442. In this way, the slider 2444 can act like a shutter that is only open at a given slider position. This may be beneficial in some embodiments of the device to prevent users from tampering with the barrel 3005 or trying to rotate it backwards to 'reset' the stroke counting mechanism 2701. Such a shutter mechanism can be incorporated into any of the implementations described herein and any number of other shutter designs are contemplated.

Figure 32A:
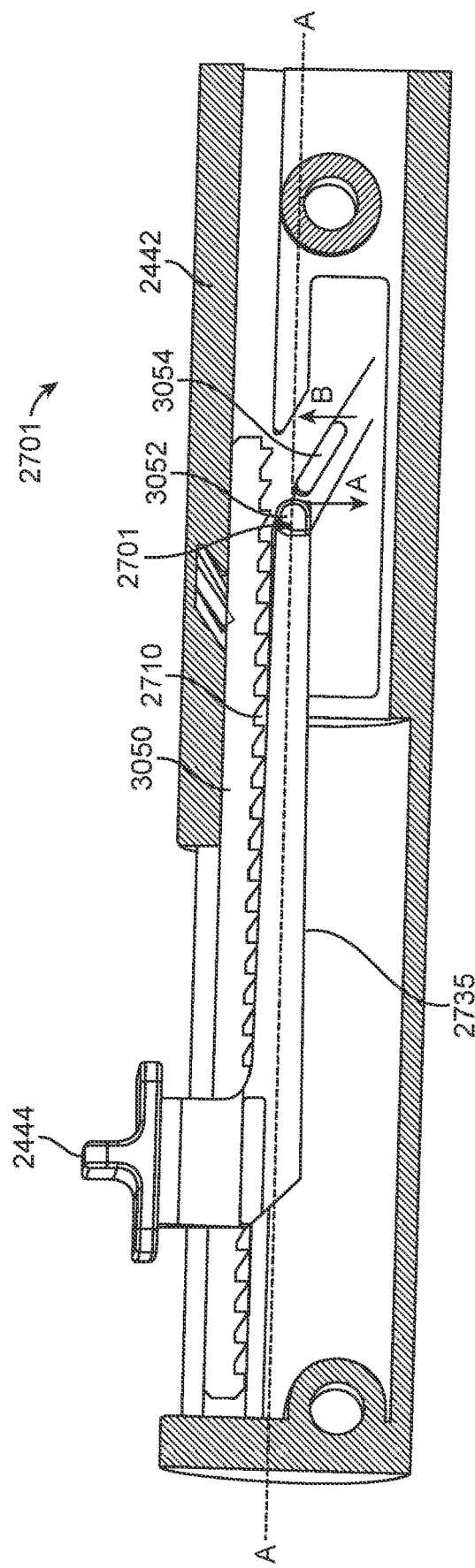
FIGS. 32A-32B illustrate another implementation of a stroke counting mechanism.
Figure 32B:
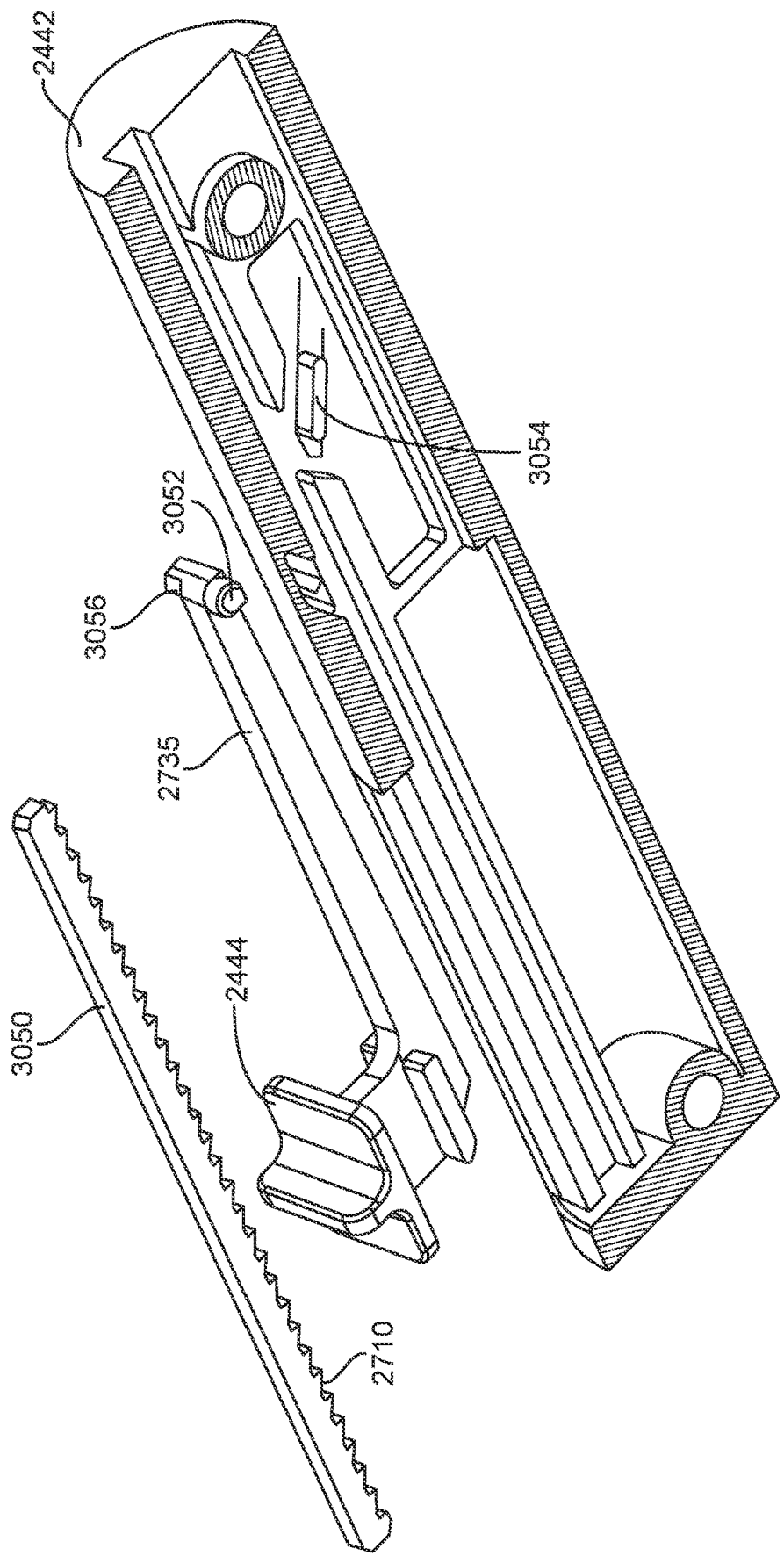

In still further implementations, the counting mechanism 2701 need not involve rotation of a barrel or cogwheel as in the implementations described above and can instead involve linear actuators. FIGS. 32A-32B illustrate an implementation of a counting mechanism 2701 that includes an axially sliding rack 3050. The rack 3050 can include a plurality of teeth 2710 configured to engage with a corresponding element such as camming bumps 3052 on a proximally-extending arm 2735 of the slider 2444. The proximally-extending arm 2735 is configured such that it is generally not in contact with the rack 3050 for the majority of its stroke. As best shown in FIG. 32A, the proximally-extending arm 2735 in an unstressed, straight position can be aligned with longitudinal axis A. As the slider 2444 is retracted proximally, the proximally-extending arm 2735 can flex away from the longitudinal axis A in a downward direction away from the teeth 2710 of the rack 3050. As the slider 2444 is advanced distally, the proximally-extending arm 2735 can relax back toward the longitudinal axis A in an upward direction toward the teeth 2710 of the rack 3050. The one or more camming bumps 3052 on a proximal-most end of the arm 2735 are configured to engage with one or more camming profiles 3054 on the interior of housing 2442 as the slider 2444 is moved proximally and distally. As the slider 2444 is retracted proximally, the camming bumps 3052 on the proximally-extending arm 2735 engage with the camming profile 3054 on the housing 2442 causing the proximally-extending arm 2735 to be urged downward (see arrow A of FIG. 32A). The proximally-extending arm 2735 elastically flexes downward relative to the slider 2444 and the housing 2442. Once the camming bumps 3054 slide proximally past the camming profile 3054, the proximally-extending arm 2735 can return upward back to its unstressed, straight position aligned with longitudinal axis A. As the slider 2444 is advanced distally, for example, to extend the sectioning element once again, the camming bumps 3052 engage with the camming profile 3054 on the housing 2442. The proximally-extending arm 2735 is urged upward and flexes toward the rack 3050 away from the longitudinal axis A. A feature 3056 on the slider 2444 engages with the teeth 2710 on the rack 3050 causing the rack 3050 to advance forward with the slider 2444 while the proximally-extending arm 2735 is flexed upward. Once the camming bumps 3052 advance distally past the camming profile 3054, the proximally-extending arm 2735 relaxes downward away from the teeth 2710 and to its neutral unstressed state aligned with longitudinal axis A. With each cycle backward and forward of the slider 2444, the camming bumps 3052 move around the camming profiles 3054 and the rack 3050 is advanced a given distance. During proximal travel of the slider 2444, the camming bumps 3052 travel down below the camming profile 3054 and the feature 3056 moved away from the teeth 2710 of the rack 3050. During distal travel of the of the slider 2444, the camming bumps 3052 travel back up above the camming profile 3054 and the feature 3056 is urged against the teeth 2710 of the rack 3050 thereby causing the rack 3050 to travel a distance forward. After a given number of cycles, the rack 3050 is configured to engage with a hard-stop on the housing such that it cannot be advanced any further. In this state, the slider 2444 is prevented from moving forward.

The devices and methods may be described in relation to preferred embodiments and it is understood that numerous modifications could be made to the preferred embodiments. For example, the tissue manipulators may have additional filaments or cross-filaments without departing from numerous aspects described.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A surgical device for cutting a lens within a capsular bag of an eye, the device comprising:

a housing comprising a distal nose cone;

a shaft extending from the distal nose cone of the housing along a longitudinal axis of the device, the shaft having at least one lumen and a distal end;

a cylindrical element positioned around a proximal end region of the shaft, the cylindrical element configured to engage and seal with an outer surface of the eye upon insertion of the shaft through a corneal incision in the eye, wherein the cylindrical element limits depth of insertion of the shaft into the eye;

a cutting element movable through the lumen of the shaft, the cutting element comprising:

at least a first sectioning element having a first end, a second end, and a distal loop formed between the first and second ends; and an actuator operatively coupled to the cutting element, wherein the cutting element is configured to transition from a first, retracted configuration towards a second, expanded configuration upon a first activation of the actuator, and wherein, when in the second, expanded configuration, the distal loop of the first sectioning element defines an enlarged open area located outside the distal end of the shaft, the enlarged open area having a first leg advanced distally relative to the distal end of the shaft and a second leg positioned proximally to the distal end of the shaft.

2. The device of claim 1, wherein the cylindrical element provides a visual indication of depth of penetration of the shaft.

3. The device of claim 1, wherein the cylindrical element is elastomeric and comprises a plurality of grooves on an outer surface allowing for the cylindrical element to compress along the longitudinal axis of the shaft upon an application of a force and to expand along the longitudinal axis of the shaft upon release of the force.

4. The device of claim 1, wherein the cutting element further comprises a second sectioning element, wherein the second sectioning element has a first end, a second end, and a distal loop formed between the first and second ends.

5. The device of claim 4, further comprising a sled positioned within the housing having a first loop carrier coupled to the first sectioning element and a second loop carrier coupled to the second sectioning element.

6. The device of claim 5, wherein the actuator is a slider movable along the longitudinal axis of the housing, wherein the sled is coupled to move with the slider relative to the housing.

7. The device of claim 6, wherein movement of the slider a first distance in a distal direction relative to the housing translates the sled distally causing the distal loops of the first and second sectioning elements to define the enlarged open areas and transition the cutting element towards the second, expanded configuration.

8. The device of claim 7, wherein, when the cutting element is in the second, expanded configuration, the distal loops defining the enlarged open areas of each of the first and second sectioning elements are aligned generally within a plane parallel to one another.

9. The device of claim 8, wherein a second activation of the actuator or a second, different actuator causes the distal loop defining the enlarged open area of one of the first and second sectioning elements to move angularly relative to the plane transitioning the cutting element into a third, splayed configuration.

10. The device of claim 9, wherein a size of the enlarged open areas of the first and second sectioning elements prior to splay is selectable using an adjustor.

11. The device of claim 10, wherein the adjustor is configured to change a relative distance between the sled and a wedge positioned within the housing, wherein a shorter relative distance achieves a smaller open area of the first and second sectioning elements in the second, expanded configuration prior to splay, and wherein a longer relative distance achieves a larger open area of the first and second sectioning elements prior to splay.

12. The device of claim 1, wherein the actuator is a slider and the device further comprises a stroke counting mechanism coupled to the slider and contained within the housing, wherein the stroke counting mechanism is configured to track distal extensions and/or proximal extensions of the slider.

13. The device of claim 12, wherein the stroke counting mechanism is configured to cause a lock-out event that prevents distal extension of the slider after the lock-out event.

14. The device of claim 13, wherein the stroke counting mechanism comprises:

a cylindrical counting barrel having a plurality of ramp blocks;
a hard stop; and
a pair of slider ramps shaped and arranged to engage with the plurality of ramp blocks on the counting barrel causing the counting barrel to rotate around the longitudinal axis.

15. The device of claim 14, wherein each distal extension of the slider turns the cylindrical counting barrel a fraction of a full revolution around the longitudinal axis.

16. The device of claim 15, wherein the cylindrical counting barrel is configured to turn up to about 24 fractions before the lock-out event occurs.

17. The device of claim 16, wherein the lock-out event prevents distal extension of the slider and allows proximal retraction of the slider.

18. The device of claim 17, wherein the slider is configured to extend about 3 to about 30 strokes in a distal direction before the lock-out event occurs and the slider is locked in a rearward position.

19. The device of claim 12, wherein the device is a single-use, disposable device.

* * * * *